United States Patent [19]

Corenman et al.

[11] Patent Number: 4,934,372
[45] Date of Patent: Jun. 19, 1990

[54] METHOD AND APPARATUS FOR DETECTING OPTICAL PULSES

[75] Inventors: James E. Corenman, Oakland; Robert T. Stone, Sunnyvale; Andras Boross, Fremont; Deborah A. Briggs, San Ramon; David E. Goodman, San Francisco, all of Calif.

[73] Assignee: Nellcor Incorporated, Hayward, Calif.

[21] Appl. No.: 334,694

[22] Filed: Apr. 5, 1989

Related U.S. Application Data

[60] Division of Ser. No. 175,152, Mar. 30, 1988, which is a continuation-in-part of Ser. No. 742,720, Jun. 7, 1985, Pat. No. 4,802,486, which is a continuation of Ser. No. 718,525, Apr. 1, 1985, abandoned.

[51] Int. Cl.$^5$ .............................................. A61B 5/02
[52] U.S. Cl. .................................. 128/633; 128/666; 128/687
[58] Field of Search ............................... 128/664–667, 128/632–633, 687–690; 356/39–41

[56] References Cited

U.S. PATENT DOCUMENTS

| | | | |
|---|---|---|---|
| Re. 27,042 | 1/1971 | Jorgensen et al. | 128/700 |
| 2,827,040 | 3/1958 | Gilford . | |
| 2,933,081 | 4/1960 | Passannante . | |
| 3,315,303 | 5/1967 | Hammacher | 128/687 X |
| 3,412,729 | 11/1968 | Smith, Jr. . | |
| 3,520,295 | 7/1970 | Kelly . | |
| 3,590,811 | 7/1971 | Harris . | |
| 3,608,545 | 9/1971 | Novack et al. | 128/700 |
| 3,618,592 | 11/1971 | Stewart . | |
| 3,651,806 | 3/1972 | Hirshberg . | |
| 3,658,060 | 4/1972 | Eklof . | |
| 3,704,706 | 12/1972 | Herczfeld et al. . | |
| 3,734,086 | 5/1973 | Phelps, Sr. . | |
| 3,742,938 | 7/1973 | Stern | 128/657 |
| 3,773,033 | 11/1973 | Rodbard et al. . | |
| 3,948,248 | 4/1976 | Zuckerman et al. . | |
| 3,994,284 | 11/1976 | Voelker . | |
| 3,994,285 | 11/1976 | Doll . | |

(List continued on next page.)

FOREIGN PATENT DOCUMENTS

| | | |
|---|---|---|
| 102816 | 3/1984 | European Pat. Off. . |
| 104771 | 4/1984 | European Pat. Off. . |
| 104772 | 4/1984 | European Pat. Off. . |
| 2089999 | 6/1982 | United Kingdom . |

OTHER PUBLICATIONS

Schotz et al., "The Ear Oximeter as a Circulating Monitor," Anesthesiology, vol. 19, p. 386, (1958).
Cohen et al., "Self-Balancing System for Medical and Physiological Instrumentation," *IEEE Trans. Bio–Med. Eng.*, vol. BME-18, p. 66, (1971).

(List continued on next page.)

*Primary Examiner*—Angela D. Sykes
*Attorney, Agent, or Firm*—Robert M. Isackson

[57] ABSTRACT

A method and apparatus for improving the calculation of oxygen saturation and other blood constituents by non-invasive pulse oximeters. The method and apparatus permit more accurate determination of blood flow by collecting time-measures of the absorption signal at two or more wavelengths and processing the collected time-measure to obtain composite pulsatile flow data from which artifacts have been filtered. The processing may occur in the time domain or in the frequency domain. In the preferred time domain embodiment, successive portions of periodic information are weighted and added together in synchrony to obtain the composite pulse information. In the preferred frequency domain embodiment, the time-measure in Fourier transformed into its spectral components to form the composite information. A new method and apparatus for correlating the heartbeat and optical pulse is provided whereby a product of the ECG R-wave and optical pulse signals corresponding to the same heartbeat is obtained, and one signal is time shifted relative to the other until a maximum waveform product corresponding to the heartbeat is determined.

37 Claims, 19 Drawing Sheets

U.S. PATENT DOCUMENTS

| | | |
|---|---|---|
| 3,998,550 | 12/1976 | Konishi et al. . |
| 4,000,461 | 12/1976 | Barber et al. . |
| 4,023,563 | 5/1977 | Reynolds et al. . |
| 4,023,564 | 5/1977 | Valiguette et al. . |
| 4,030,485 | 6/1977 | Warner . |
| 4,036,211 | 7/1977 | Veth et al. . |
| 4,053,911 | 10/1977 | Hudspeth et al. . |
| 4,063,551 | 12/1977 | Sweeney . |
| 4,086,915 | 5/1978 | Kofsky . |
| 4,154,230 | 5/1979 | Lee .................. 128/661 |
| 4,181,134 | 1/1980 | Mason et al. ............ 128/689 |
| 4,216,779 | 8/1980 | Squires et al. ........... 128/682 |
| 4,266,554 | 5/1981 | Hamaguri ............... 128/633 |
| 4,325,384 | 4/1982 | Blaser et al. ............ 128/696 |
| 4,353,998 | 10/1982 | Sawa ..................... 128/633 |
| 4,402,325 | 6/1983 | Sawa ..................... 128/666 |
| 4,406,658 | 9/1983 | Lattin et al. ........... 128/802 X |
| 4,407,290 | 10/1983 | Wilber .................. 128/633 |
| 4,422,458 | 12/1983 | Kravath ................. 128/671 |
| 4,425,921 | 1/1984 | Fujisaki et al. .......... 128/700 |
| 4,425,922 | 1/1984 | Conti et al. ............. 128/691 |
| 4,440,176 | 4/1984 | Miodownik .............. 128/708 |
| 4,446,868 | 5/1984 | Aronson ................. 128/708 |
| 4,446,871 | 5/1984 | Imura ................... 128/664 X |
| 4,450,838 | 5/1984 | Miodownik .............. 128/204.23 |
| 4,545,387 | 10/1985 | Balione ................. 128/666 X |
| 4,573,478 | 3/1986 | Arnold et al. ........... 128/670 |
| 4,577,639 | 3/1986 | Simon et al. ............ 128/709 |
| 4,586,513 | 6/1986 | Hamaguri ............... 128/633 |
| 4,589,420 | 5/1986 | Adams et al. ............ 128/702 |
| 4,617,937 | 10/1986 | Peel et al. .............. 128/686 |
| 4,653,498 | 3/1987 | New, Jr. et al. .......... 128/666 X |
| 4,802,486 | 2/1989 | Goodman et al. .......... 128/666 X |
| 4,824,242 | 4/1989 | Frick et al. ............. 128/666 X |

OTHER PUBLICATIONS

Goodlin, "Interpartum Fetal Heart Rate Responses and Plethysmographic Pulse", *Amer. J. Obstet. Gynec.*, vol. 110, p. 210, (1971).

Goodlin et al., "Systolic Time Intervals in the Fetus and Neonate" *Obstetrics and Gynecology*, vol. 34, p. 295, (Feb. 1972).

Goodlin, *Care for the Fetus*, p. 101, (Masson 1979).

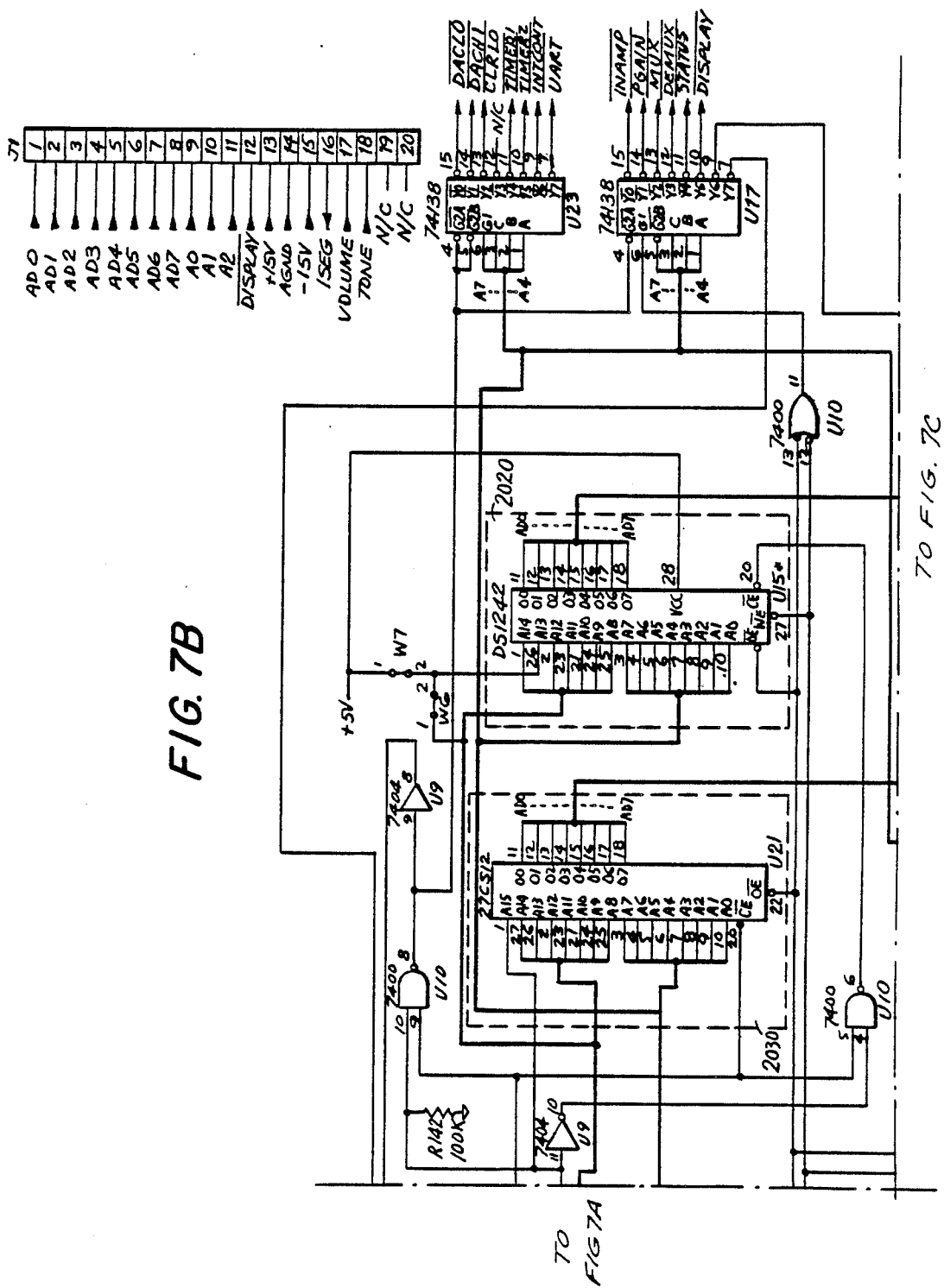

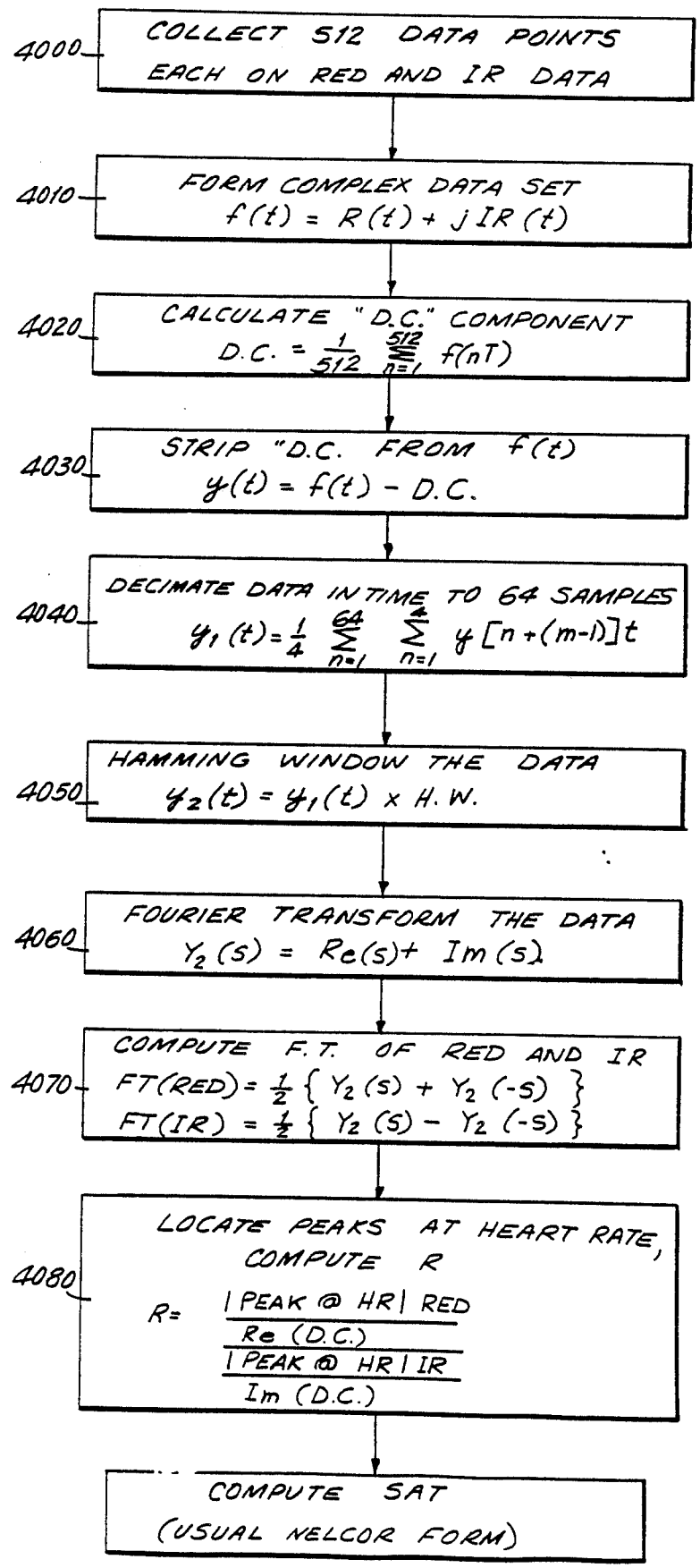
FIG. 10 — FOURIER OXIMETER FLOWCHART

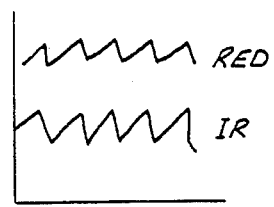
FIG. 10a
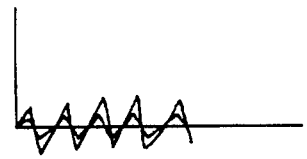
FIG. 10b
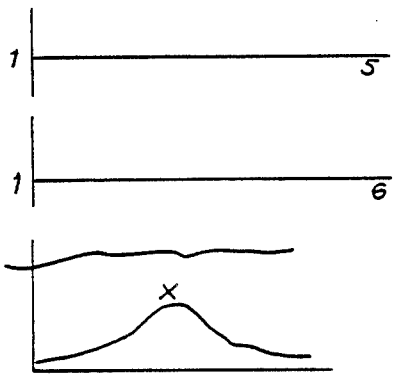
FIG. 10c
FIG. 10d
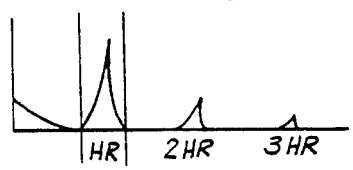
FIG. 10e

METHOD AND APPARATUS FOR DETECTING OPTICAL PULSES

CROSS REFERENCE TO RELATED APPLICATIONS

This is a division of application Ser. No. 07/175,152, filed Mar. 30, 1988, entitled IMPROVED METHOD AND APPARATUS FOR DETECTING OPTICAL PULSES in the names of Robert T. Stone, Andrash Boross, Deborah A. Briggs, James E. Corenman and David E. Goodman, now allowed, which is a continuation-in-part application of copending and commonly assigned U.S. application Ser. No. 742,720, entitled Improved Method and Apparatus For Detecting Optical Pulses, filed June 7, 1985 in the names of James E. Corenman and David E. Goodman, now U.S. Pat. No. 4,802,486, which is a continuation of U.S. application Ser. No. 718,525, entitled Improved Method and Apparatus For Detecting Optical Pulses, filed Apr. 1, 1985 in the names of James E. Corenman and David E. Goodman, now abandoned.

This invention relates to non-invasive pulse oximetry and specifically to an improvement on the method and apparatus for photoelectric determination of blood constituents disclosed in U.S. application Ser. Nos. 742,720 and 718,525. This specification is accompanied by software appendices A and B.

BACKGROUND OF THE INVENTION

Non-invasive photoelectric pulse oximetry has been previously described in U.S. Pat. No. 4,407,290, U.S. Pat. No. 4,266,554, U.S. Pat. No. 4,086,915, U.S. Pat. No. 3,998,550, U.S. Pat. No. 3,704,706, European Patent Application No. 102,816 published Mar. 13, 1984, European Patent Application No. 104,772 published Apr. 4, 1984, and European Patent Application No. 104,771 published Apr. 4, 1984. Pulse oximeters are commercially available from Nellcor Incorporated, Hayward, Calif., U.S.A., and are known as, for example, Pulse Oximeter Model N-100 (herein "N-100 oximeter").

Pulse oximeters typically measure and display various blood flow characteristics including but not limited to blood oxygen saturation of hemoglobin in arterial blood, volume of individual blood pulsations supplying the flesh, and the rate of blood pulsations corresponding to each heartbeat of the patient. The oximeters pass light through human or animal body tissue where blood perfuses the tissue such as a finger, an ear, the nasal septum or the scalp, and photoelectrically sense the absorption of light in the tissue. The amount of light absorbed is then used to calculate the amount of blood constituent being measured.

The light passed through the tissue is selected to be of one or more wavelengths that is absorbed by the blood in an amount representative of the amount of the blood constituent present in the blood. The amount of transmitted light passed through the tissue will vary in accordance with the changing amount of blood constituent in the tissue and the related light absorption.

For example, the N-100 oximeter is a microprocessor controlled device that measures oxygen saturation of hemoglobin using light from two light emitting diodes ("LED's"), one having a discrete frequency of about 660 nanometers in the red light range and the other having a discrete frequency of about 925 nanometers in the infrared range. The N-100 oximeter microprocessor uses a four-state clock to provide a bipolar drive current for the two LED's so that a positive current pulse drives the infrared LED and a negative current pulse drives the red LED to illuminate alternately the two LED's so that the incident light will pass through, e.g., a fingertip, and the detected or transmitted light will be detected by a single photodetector. The clock uses a high strobing rate, e.g., one thousand five hundred cycles per second, to be easily distinguished from other light sources. The photodetector current changes in response to the red and infrared light transmitted in sequence and is converted to a voltage signal, amplified, and separated by a two-channel synchronous detector—one channel for processing the red light waveform and the other channel for processing the infrared light waveform. The separated signals are filtered to remove the strobing frequency, electrical noise, and ambient noise and then digitized by an analog to digital converter ("ADC"). As used herein, incident light and transmitted light refers to light generated by the LED or other light source, as distinguished from ambient or environmental light.

The light source intensity may be adjusted to accomodate variations among patient's skin color, flesh thickness, hair, blood, and other variants. The light transmitted is thus modulated by the absorption of light in the variants, particularly the arterial blood pulse or pulsatile component, and is referred to as the plethysmograph waveform, or the optical signal. The digital representation of the optical signal is referred to as the digital optical signal. The portion of the digital optical signal that refers to the pulsatile component is labeled the optical pulse.

The detected digital optical signal is processed by the microprocessor of the N-100 oximeter to analyze and identify arterial pulses and to develop a history as to pulse periodicity, pulse shape, and determined oxygen saturation. The N-100 oximeter microprocessor decides whether or not to accept a detected pulse as corresponding to an arterial pulse by comparing the detected pulse against the pulse history. To be accepted, a detected pulse must meet certain predetermined criteria, for example, the expected size of the pulse, when the pulse is expected to occur, and the expected ratio of the red light to infrared light of the detected optical pulse in accordance with a desired degree of confidence. Identified individual optical pulses accepted for processing are used to compute the oxygen saturation from the ratio of maximum and minimum pulse levels as seen by the red wavelength compared to the maximum and minimum pulse levels as seen by the infrared wavelength.

Several alternate methods of processing and interpreting optical signal data have been disclosed in the patents and references cited above.

A problem with non-invasive pulse oximeters is that the plethysmograph signal and the optically derived pulse rate may be subject to irregular variants in the blood flow, including but not limited to motion artifact, that interfere with the detection of the blood flow characteristics. Motion artifact is caused by the patient's muscle movement proximate to the oximeter sensor, for example, the patient's finger, ear or other body part to which the oximeter sensor is attached, and may cause spurious pulses that are similar to pulses caused by arterial blood flow. These spurious pulses, in turn, may cause the oximeter to process the artifact waveform and provide erroneous data. This problem is particularly significant with infants, fetuses, or patients that do not remain still during monitoring.

A second problem exists in circumstances where the patient is in poor condition and the pulse strength is very weak. In continuously processing the optical data, it can be difficult to separate the true pulsatile component from artifact pulses and noise because of a low signal to noise ratio. Inability to reliably detect the pulsatile component in the optical signal may result in a lack of the information needed to calculate blood constituents.

It is well known that electrical heart activity occurs simultaneously with the heartbeat and can be monitored externally and characterized by the electrocardiogram ("ECG") waveform. The ECG waveform, as is known to one skilled in the art, comprises a complex waveform having several components that correspond to electrical heart activity. The QRS component relates to ventricular heart contraction. The R wave portion of the QRS component is typically the steepest wave therein, having the largest amplitude and slope, and may be used for indicating the onset of cardiovascular activity. The arterial blood pulse flows mechanically and its appearance in any part of the body typically follows the R wave of the electrical heart activity by a determinable period of time that remains essentially constant for a given patient. See, e.g., Goodlin et al., "Systolic Time Intervals in the Fetus and Neonate", *Obstetrics and Gynecology*, Vol. 39, No. 2, February 1972, where it is shown that the scalp pulse of fetuses lag behind the ECG "R" wave by 0.03–0.04 second, and U.S. Pat. No. 3,734,086.

In prior U.S. application Ser. No. 742,720, copending and commonly assigned, the disclosure (including the software appendix) of which is hereby expressly incorporated by reference, and in corresponding International PCT Application publication No. WO 86/05674 published Oct. 9, 1986, also commonly assigned, there is disclosed an invention for measuring the patient's heart activity and correlating it with the patient's detected blood flow signals to calculate more accurately the patient's oxygen saturation and pulse rate. The correlation includes auto- and cross correlation techniques to enhance the periodic information contained in each individual waveform as well as determine the time relationship of one waveform to another.

Correlating the occurrence of cardiovascular activity with the detection of arterial pulses occurs by measuring an ECG signal, detecting the occurrence of the R-wave portion of the ECG signal, determining the time delay by which an optical pulse in the detected optical signal follows the R-wave, and using the determined time delay between an R-wave and the following optical pulse so as to evaluate arterial blood flow only when it is likely to present a true blood pulse for waveform analysis. The measured time delay is used to determine a time window when, following the occurrence of an R-wave, the probability of finding an optical pulse corresponding to a true arterial pulse is high. The time window provides an additional criterion to be used in accepting or rejecting a detected pulse as an optical pulse. Any spurious pulses caused by motion artifact or noise occurring outside of that time window are typically rejected and are not used to calculate the amount of blood constituent. Correlating the ECG with the detected optical pulses thereby provided for more reliable measurement of oxygen saturation.

That application and publication refers to a modified N-100 oximeter (the "enhanced N-100 oximeter") whereby the device is provided with an additional heart activity parameter in the form of a detected R-wave from the patient's ECG waveform, in addition to the N-100 pulse oximeter functions, and the microprocessor is modified to include software and memory for controlling and processing the optical signal and heart activity information.

The additional heart activity parameter is independent of the detection of peripheral arterial pulses, e.g., ECG signals, ultrasound, ballistocardiogram, and maybe, accelerometers, nuclear magnetic resonators, electrical impedance techniques, and the like, and provides an identifiable and detectable signal in response to each heartbeat for use by the signal processing of the oximeter.

It is an object of this invention to provide for improved processing of the detected optical signal containing periodic information corresponding to arterial pulsatile blood flow and aperiodic information corresponding to noise, spurious signals, and motion artifact unrelated to the beating heart and arterial pulsatile blood flow, to improve further the reliability and accuracy of the determination of blood constituent, particularly oxygen saturation of hemoglobin by a non-invasive oximeter device.

It is another object of this invention to provide an improved method and apparatus for collecting successive portions of detected optical signals encompassing periodic information for more than one heartbeat and processing the collected portions to attenuate and filter therefrom aperiodic signal waveforms to provide enhanced periodic information from which the patient's blood constituent can be accurately determined.

It is another object to maintain the enhanced periodic information updated by continuing to add new portions of detected optical signals as they are obtained.

It is another object of this invention to create enhanced periodic information by collecting and processing successive portions of detected optical signals wherein the periodic information corresponding to the optical pulses have been added together in phase, synchronized to the occurrence of the patient's ECG and preferably the R-wave signal.

It is another object of this invention to add synchronized periodic information in a weighted fashion so that the most recent portion of detected optical signal is accorded a greater weight in the collected sum than any one prior portion of periodic information data.

It is another object of this invention to create the enhanced periodic information by adding together a predetermined number of the most recent successive portions of detected optical signal, whereby each portion corresponds to a heartbeat event and is given a weight according to its relative age so as to emphasise the newest information in the resultant weighted collective sum.

It is another object of this invention to correlate the periodic information with the ECG R-wave by using a waveform product technique to identify the occurrence of the heartbeat and the optical pulse corresponding to that heartbeat.

It is another object of this invention to evaluate the collected periodic information for a predetermined number of successive portions of the detected optical signal corresponding to a predetermined number of heartbeats in the frequency domain to obtain enhanced periodic information.

It is another object of this invention to Fourier transform a time-measure of detected optical signals including periodic information for N heartbeats to determine the relative maxima at the fundamental frequency N and the minima at the zero frequency for use in determining the light modulation ratio for the amount of blood constituents.

It is another object of this invention to correlate the Fourier Transform of the time-measure of detected optical signals with the Fourier Transform of a time-measure of the ECG signal, and more particularly the R-wave events of the ECG signal, to determine the maxima at the fundamental heart frequency.

It is another object of this invention to correlate the periodic information in a time-measure of the detected optical signal with a time-measure of the detected heart activity, preferably in the form of the ECG signal and more preferably in the form of the R-wave of the ECG signal, to define a predetermined number of samples in a data set and use frequency domain analysis techniques to evaluate the collected predetermined number of sample data sets to determine the relative maxima at the fundamental frequency.

SUMMARY OF THE INVENTION

This invention provides enhanced periodic information with improved rejection of noise, spurious pulses, motion artifact, and other undesired aperiodic waveforms and thereby improves the ability of oximeters to accurately determine amounts of blood constituents.

The present invention provides methods and apparatus for collecting a time-measure of the detected optical signal waveform containing a plurality of periodic information corresponding to arterial pulses caused by the patient's heartbeat and aperiodic information unrelated to pulsatile flow, and processing the collected time-measure of information to obtain enhanced periodic information that is closely related to the most recent arterial pulsatile blood flow. The time-measure may comprise a continuous portion of detected optical signals including a plurality of periodic information from successive heartbeats, or a plurality of discrete portions of detected optical signals including a corresponding plurality of periodic information.

By updating the time-measure of information to include the most recently detected periodic information, and processing the updated measure collectively, an updated enhanced periodic information is obtained (including the new and historical data) from which aperiodic information (including any new aperiodic information) is attenuated. In some embodiments, the updating process includes substracting detected signals older than a certain relative time from the collected time-measure. Applicants have discovered that by collectively processing a time-measure including successive periodic information to obtain the enhanced periodic information, and using the enhanced periodic information as the basis for making oxygen saturation calculations, the accuracy and reliability of oxygen saturation determinations can be significantly increased. Applicants also have discovered that the time-measures may be collectively processed in either the time domain or the frequency domain.

The amount of a blood constituent, for example, oxygen saturation, can be then determined from this enhanced periodic information (also referred to as composite signal information) by determining the relative maxima and minima in the enhanced periodic information for the respective wavelengths for use in determining the modulation ratios of the known Lambert-Beers equations.

In the preferred embodiment, the detected optical signals are conventionally obtained by passing red (660 namometers) and infrared (910 namometers) light through a patient's blood perfused tissue, detecting the transmitted light which is modulated by the blood flow, and providing red and infrared detected optical signals that are preferably separately processed and optionally converted from analog to digital signals, for example, as described above for the Nellcor N-100 oximeter. Portions of the corresponding red and infrared digital signals are then collectively processed in accordance with the present invention and the light modulation ratios are determined based on the resulting enhanced periodic information and used to calculate oxygen saturation.

In the time domain analysis embodiment, the invention provides a method and apparatus for adding together a plurality of successive portions of the detected optical signal waveform whereby one portion of the detected optical signal waveform is added to the following selected portion so that their respective periodic information is added in synchrony, i.e., in phase. The synchronized sum thus forms a composite portion of detected optical signal information having enhanced periodic information. The following portion is then added to the composite portion so that the new periodic information is added to the prior composite periodic information in synchrony, forming an updated composite portion with updated enhanced periodic information. Thereafter, subsequent successive portions of detected optical signal are added to the prior updated composite portion, one at a time, so that the composite and enhanced periodic information are updated with each new portion and corresponding heartbeat event.

Weighting functions are applied to the two portions before they are added each other. This provides a scaled or weighted sum that can be adjusted, by selection of the respective weighting functions, to more closely reflect the patient's current condition, rather than the historical condition. In the preferred embodiment, the weighting functions are fractional multipliers which sum to one to provide a stable filter, and are discussed in greater detail below.

The periodic information (optical pulse) generally has the same pulse shape, height, and duration from heartbeat to heartbeat and, as is described in U.S. Ser. No. 742,720, follows heart activity by a determinable period of time.

Applicants have discovered that by synchronizing the occurrence of successive R-waves, it becomes possible to add the corresponding successive portions of the detected optical signal together so that the periodic information (optical pulses) corresponding to the arterial pulse in each portion will add in phase. The weighted magnitude of the new periodic information is reinforced by the existence of the weighted enhanced periodic information at the same time location in accordance with the degree of synchrony. If the new optical pulse is identical to the composite pulse, then the updated result is a composite optical pulse having the same magnitude. If the magnitudes differ, the additive result will differ according to the relative weights.

As a result of the collected, synchronized additive process, any aperiodic information that may be present in the portions of the detected optical signals also are weighted and added to the weighted composite portion waveform. However, because aperiodic signals differ in pulse shape, duration, height, and relative time of occurrence within each portion, and are not synchronous with heart activity, they do not add in phase. Rather, they add in a cancelling manner whereby their weighted sum is spread across the relative time frame of the composite portion.

Applicants have discovered that by processing portions including the periodic information collectively, aperiodic information is attenuated by the absence of any corresponding historical aperiodic signal in the prior composite portion or any subsequent aperiodic at that relative time following heart activity. Further, because the new information can be given a small weight when compared to the absolute weight given the prior composite (as distinguished from the effective lesser weight given to any single prior portion of optical signals as explained below) new aperiodic information is quickly and effectively attenuated, and thus filtered out of the resultant additive portions.

To the extent that any aperiodic information would overlap and thereby obscure some periodic information in a portion, then that aperiodic information would be reinforced by the existing periodic information in the prior composite portion; but only to the extent there was overlap. Thus, the collective processing does not lose optical pulse information hidden by an artifact. Subsequent periodic information lacking "identical" aperiodic information would attentuate any overlapping aperiodic pulse over time.

The collective additive sum having synchronized periodic information waveforms thus presents enhanced periodic information that is a composite data set that corresponds to a composite optical pulse from which noise, spurious signals, and motion artifact, have been filtered out. By weighting the collective additive process to favor the most recent information and processing this weighted composite portion as it is updated, an accurate estimated optical pulse (enhanced periodic information) that closely reflects the actual conditions is maintained. Basing oxygen saturation determinations on this enhanced optical pulse as it is updated thus provides a more accurate measure than was available by conventional and prior processing techniques.

As discussed in application Ser. No. 742,720, the determinable time period between the R-wave and the optical pulse makes it possible to determine a time window whose time length is long enough to include any likely periodic information, and short enough to exclude detected optical signals that are not of any significant or clinical use in making the determination of the selected blood constituent. A time window can be used in the present invention, following the occurrence of heart activity, to select a portion of detected optical signals for processing in accordance with this invention to reduce the amount of detected optical signal information that must be processed, to improve the rejection of aperiodic signals not proximate to the optical pulse, and to improve the resolution of the oximeter. The timing of the portion can be selected empirically, by considering the time length of the heartbeat pulse and how long it takes for the pulse to travel to the optical detection site so that the window is opened before the optical pulse maximum occurs at the optical detection site. In the preferred embodiment, the portion of signal is a portion that begins 40 ms after the detection of an R-wave event, based on experimentation, and ends after the relative minimum of the optical pulse is detected, which ending time can vary from portion to portion, and may be, for example, about 230 ms after the R-wave event.

The time domain processing of collective weighted portions of the detected optical signal waveforms synchronized by the R-wave of the ECG waveform provides the equivalent of an optimal filter in the frequency domain, whose band-pass elements are those of an ideal heartbeat for the patient under examination. All frequencies which are found in a normal heartbeat are passed with weights of one, and all nonsynchronous frequencies are rejected with attenuation depending on the degree of asynchrony, and the time length of the filter (the effective number of portions processed collectively). As the weight of the periodic information corresponding to the current heartbeat is decreased, greater rejection of low-frequency aperiodic artifacts occurs, but the delay in reporting the most accurate arterial pulsatile flow increases.

The weighting functions also assure that the new periodic information is not absorbed into the time and amplitude average of the old data. Using fractional weights provides scaling of the new and old composite information sum, and when the fractional weights add to one, stable performance of the filter is assured. Repeated multiplication of the old data by weights less than one accomplish the effective removal of older data, thus limiting in effect the number of periods processed collectively.

In the preferred embodiment, the detected optical signal information is processed in digitized form. Because the successive digitized information is weighted and added, the amount of digital computer memory required to contain the historical and updated composite periodic information only need be as long as the time period for a relative typical heartbeat, so that it can contain the entire time for a selected portion including an optical pulse. This simplifies oximeter operation.

In the preferred embodiment, applicants have found that optimal performance occurs when the most recent information is accorded a weight of 1/6 and the historical weight-averaged composite information is accorded a weight of 5/6. Weights which are in powers of 2, e.g., $\frac{1}{2}$, $\frac{1}{4}$, $\frac{1}{8}$, etc., are attractive to use with binary digital computers because they require simpler mathmatical operations, however, they do not necessarily provide the optimal time and noise attenuation tradeoff in selecting weighting functions.

The resultant enhanced periodic information is a weighted composite optical pulse that is evaluated in the same manner that prior oximeters evaluated individual pulses they determined were appropriate optical pulses for determining blood constituents, whether or not the criteria included use of a time window. The relative maxima and minima for each of the red and infrared composite optical pulses are separately determined and used in the modulation ratios for determining amounts of blood constituent, e.g., in the modulation ratio R of the Lambert-Beers equations that are commonly used to determine oxygen saturation of arterial hemoglobins as described below. As additional data sets are taken, the collective set of periodic information is updated. Consequently, the most recent waveform data representing the actual amount of blood constituent is included in the updated composite optical pulse from which the updated oxygen saturation can be determined and displayed. Although the foregoing and following discussions generally discuss only a detected optical signal, it should be understood that both the red and infrared signal are separately obtained and processed by these techniques, except as indicated.

In another embodiment of the time domain embodiment, the time-measure of the detected optical signal is collected in a different manner. The digitized portions of information that are to be weighted, synchronously added together, and processed collectively are accumulated in a memory device having sufficient memory locations for storing separately the raw data for a predetermined number of portions of the detected optical signal. The time of occurrence of the R-wave also may be stored in memory as a pointer for the raw data. This filter embodiment permits assigning a different weighting function to each raw data set corresponding to a different heartbeat in the memory, to improve the attenuation of artifacts and reduce the time needed to estimate the actual arterial pulsatile flow in the detected optical signal.

In this embodiment, for N predetermined heartbeats, the average value of the detected optical signal for those N heartbeats is computed by assigning a weight to each data set and adding the weighted data for each heartbeat synchronously into a buffer with a weight of 1, then dividing by N. After each computation, the data set from the oldest stored heartbeat is subtracted from the buffer. As a new R-wave is detected, the incoming data is added to the buffer, and the result is divided by N for computation of relative amplitudes of the two wavelength (red and infrared) periodic information. Thus, the equivalent delay in determining the arterial oxygen saturation is N/2 times the heartbeat interval. The stored R-wave pointer may be used to correlate the weighting function with the raw data so that the oldest data is given the smallest weight and the most recent data is given the greatest weight, and after each composite heartbeat computation, the oldest data set can be subtracted from the buffer before the following newest data is added.

In an alternate embodiment of the time domain analysis techniques, the ECG and periodic information can be correlated by using a waveform product of the ECG signal and the detected optical signal to determine the location of the optical pulse from which oxygen saturation and heart rate values may be computed. The R-wave of the ECG has the largest slope component within the ECG waveform. In the optical pulse waveform in the portion of detected optical signal, the largest slope is created when the heart contracts to expell blood and thereby produce the arterial pulse. Thus, because of the determinable time interval between the ECG R-wave and the appearance of the optical pulse at the detection site, the detected optical signal can be moved backwards in time, relative to the ECG waveform, an amount equal to the determined time interval so that the portions of maximum slope in the two signals will be aligned, and their product will be at a maximum.

Aperiodic signals, such as motion artifact, having high slopes will not occur synchronously on the ECG and the detected optical signals. Therefore, once the two periodic waveforms are aligned, the largest slope product of the two will occur at the heart rate interval. Detection of the maximum slope product can be used to pinpoint the occurrence of a heartbeat, and the portion of the detected optical signal that is associated with that maximum slope product can be used for calculating oxygen saturation.

In this embodiment, the time interval between the R-wave and the optical pulse can be determined by collecting a predetermined time measure history of optical and ECG waveform data comprising n seconds. The time interval must be long enough for the samples to include at least one R-wave and one pulse respectively, given that the heartbeat may vary from 20–30 beats per minute at the slowest rates. A measure of six seconds is acceptable. The samples are conventionally digitized and stored in memory. An array of sample-to-sample slopes is obtained for each n second sample of the ECG waveform and for the second half of each optical pulse waveform sample. The first half of the optical pulse sample is discarded so that when the first optical pulse in the second half is slid backwards, the first R-wave peak it will come upon will be its corresponding R-wave, and also so that the most recent heartbeat data is detected. An optical pulse in the first half of the sample could miss its R-wave.

The number of slope values in the second half of the optical waveform, i.e. the number of data points minus 1 at the given sampling rate of 57 samples per second (every 17.5 msec), is taken as m, which corresponds to n/2 seconds of data.

A slope product is obtained by multiplying each element of the optical slope array by its corresponding three and one-half points in the ECG slope array (the ECG signal is sampled every 5 msec) and summing the products. This process is repeated for each of the m optical sample points as the optical waveform slope array is moved backwards relative to the ECG slope array, one optical waveform sample at a time. The backwards slide terminates when the first sample of the ECG waveform is aligned with the first sample of the second half of the optical waveform.

The maximum slope product is found to occur after the optical waveform slope array has been slid x optical sample points backwards. This establishes the time interval t between the detection of the ECG R-wave and the detection of the optical pulse produced by the same heart contraction. This time interval t is expressed in terms of a number of waveform samples, and is used in the determination of heartbeat occurrence.

Computation of the aligned waveform slope product will yield a slope product value for each optical waveform sample. A percentage of the maximum slope product produced during the establishment of the time interval component can be used to compute a maximum product threshold. For example, a percentage of 75% of the maximum slope product may be used. Thus, when the ECG and optical signal waveform slope product exceeds the maximum product threshold, it is likely that a true pulse has been located.

The "true" pulse, as it appears in the detected optical signal, can then be validated and processed using known techniques for calculating oxygen saturation from detected optical signals. For example, the slope product could be used to synchronize the R-wave events so that the corresponding periodic information can be added in phase in accordance with the preferred embodiment of this invention, or the slope product could be used as an additional criterion for accepting the corresponding optical pulse as valid, and the oxygen saturation determination could be based only on the corresponding optical pulse. Alternately, the waveform product for the maximum and minimum values for the red and infrared waveforms could be used as the maximum and minimum values in calculating saturation.

Also, one could integrate some portion of the selected waveform product waveform and compare the area of the change to the area of the total signal to obtain the relative transmittance for use in determining saturation. For example, one could integrate the portion above a selected threshold and compare that area to the integral of the entire pulse.

Qualified "true" pulses are then used to update the slope product threshold value so that it will change as the patient's condition changes or as the quality of the received signals changes.

Applicants also have discovered that a time-measure of detected optical signals containing a plurality of periodic information corresponding to successive heartbeats can be collectively processed and analyzed using frequency domain techniques. These frequency domain techniques utilize the synchronous nature of the heartbeat and the asynchronous characteristics of noise, spurious signals, and motion artifacts.

In the frequency domain, the optical signals for a given wavelength corresponding to the pulsatile arterial blood flow have spectral components including a zero frequency at the background intensity level, a fundamental frequency at the frequency of the beating heart, and additional harmonic frequencies at multiples of the fundamental frequency. Noise, spurious signals, and motion artifact that appear in the detected optical signal have frequencies that spread across the spectrum. Transient changes in the average background intensity level have frequencies that appear spread out between the zero frequency and the fundamental frequency.

The frequency domain embodiment of the present invention provides a method and apparatus for collecting a time-measure of detected optical signals including a predetermined number of optical pulses, converting the collected detected optical signals into the frequency domain, and analyzing the spectral components of the frequency spectrum thereby to determine the red and infrared relative maxima intensity at the fundamental frequency, and relative minima at the background intensity zero frequency, for use as maxima and minima in the percentage modulation ratio for calculating oxygen saturation.

Applicants have discovered that if the digitized values of the time domain detected optical signals are stored in memory for a period of N heartbeats, and the stored data set is transformed into the frequency domain using Fourier Transforms, the amplitude of the fundamental heartrate is summed for the N heartbeats and appears in the frequency spectrum at a location of N cycles. In contrast, the amplitude of asynchronous signals is 1/m, where m is the number of data points in the digitized stored data set, and appear spread across the frequency domain spectrum. The average intensity of the detected optical signal background intensity appears at the spectral line corresponding to zero cycles and corresponds to the average background intensity for that wavelength.

If the detected optical signal for the red and infrared signals is considered as a single complex data set, i.e., having real and imaginary components, only a single Fourier transform is required to analyze the spectral contents of the collective time-measure of the two signals. If F(s) represents the Fourier Transform of the complex data set $f(t) = Red(t) + jIR(t)$ (for Red(t) being the red detected optical signal and IR(t) being the infrared detected optical signal), the Fourier Transform of the real component of f(t) is found by $$F\{Re[f(t)]\} = \tfrac{1}{2}\{F(s) + F^*(-s)\}.$$

Similarly, the Fourier transform of the imaginary component of f(t) is found by $$F\{Im[f(t)]\} = \tfrac{1}{2}\{F(s) - F^*(-s)\}.$$

$F^*(-s)$ is the complex conjugate of F(s) with the index s reversed.

The relative amplitudes of the red and infrared fundamentals at the heartrate has been found to be equivalent to the foregoing time domain techniques for computation of arterial oxygen saturation. The amplitude data may be found by searching the frequency spectrum in the region of expected heart rates for a relative maximum and insuring that this is the fundamental by determining the existence of another relative maximum at twice this rate. This provides a technique for obtaining relative modulation data to calculate arterial oxygen saturation without the need to identify the heart rate independently, e.g., by detecting the ECG. Alternately, the amplitude data at the fundamental may be found by the use of independent heart rate determining mechanism such as ECG or phonoplethysmography or the like to determine a heart rate. However, unlike the time domain techniques, the precise time of occurrence of each heartbeat need not be determined and the optical signal and a heart rate parameter need not be correlated to obtain accurate saturation values. Rather, it is sufficient to obtain an approximate indicator of heart rate, which will facilitate identification of the fundamental frequency and improve saturation reliability.

The number of spectral lines computed is preferably optimized to include the expected range of clinically applicable heartbeats (from 20–250 beats per minute), while the length of the data set is selected by the allowable equivalent delay in displaying measured arterial oxygen saturaton. A time-measure of data of, for example, 9–10 seconds represent delays of only 4–5 seconds in the display of computed saturations, and, depending upon the computational speed of the oximeter microprocessor, the time-measure can be updated in a timely fashion every 1 to 2 seconds.

In the preferred embodiment, the optical signal is digitized at 57 samples per second for each red and infrared signal. When 512 data points are accumulated, the data is Fourier transformed, and the red and infrared fundamental maxima are located. The percentage modulation ratio (red/infrared) is computed by dividing the energy at each maxima by the zero cycle background intensity for that wavelength, then dividing the red modulation by the infrared modulation. The resultant ratio, R, is then used in the manner set forth in the Lambert-Beers equations for calculating arterial saturation of hemoglobin. The collective data can be updated so that new data points replace the oldest data points by using a push down stack memory or equivalent so that the transform, evaluation and saturation calculation could be made after each new data set was obtained.

An alternative embodiment of the frequency domain analysis technique includes sampling the real time ECG waveform and the real time detected optical signal at high rates, e.g., 1000 samples per second. By examining the ECG wave, the time of occurrence of each heartbeat and the appropriate sample rate to obtain m samples during that heartbeat could be determined. Thus, the data set for each heartbeat can be selected to contain the same number of m samples, where each sample is a fraction of the heartbeat period, and N heartbeats contains mxN samples. Taking the Fourier transform of this mxN data set and processing the spectral components of the transform in the same manner as described previously, results in a spectral analysis having several additional advantages. First, the fundamental maximum would always occur at the spectral line for N cycles in "heartbeat" space. Second, any signal present in the data set which did not remain synchronous with the heart, including noise, artifact and transient background intensity changes, would be spread over the heartbeat spectrum. Third, the enhancement in signal-to-noise would be the same for all heart rates. Fourth, because only two spectral lines are of interest, the zero spectral line corresponding to the zero frequency background intensity and the N spectral line corresponding to the number of heartbeats for the data set, the Fourier Transform need only be made at the two frequency components and not of the entire spectrum, and the computation efforts required by the microprocessor are significantly diminished.

The apparatus of the present invention can be used for either time domain or frequency domain analyses, and includes inputs for the plethysmographic detected optical signals and ECG signals of a patient, an analog to digital converter for converting the analog plethysmographic signal to the digital optical signals and for converting the analog ECG signals into digital ECG signals (unless the plethysmographic or ECG signals are provided in digital form), and a digital signal processing section for receiving the digital signals and processing the digital detected optical signal in accordance with one of the foregoing analysis techniques of the present invention, including a microprocessor, memory devices, buffers, software for controlling the microprocessor, and display devices.

In its context, the apparatus of the present invention is a part of an oximeter device which has the capability to detect the red and infrared light absorption, and receive an ECG signal from the patient. In the preferred embodiment, the apparatus of this invention is a part of the Nellcor N-200 Pulse Oximeter (herein the "N-200 oximeter"), a commercially available noninvasive pulse oximeter device manufactured and sold by Nellcor, Incorporated, Hayward, Calif. U.S.A.

The N-200 oximeter is an improved version of the enhanced N-100 oximeter described above and in the prior application serial number 742,720. The N-200 includes circuits that perform many of the same functions as in the N-100 device, but includes some changes, for example, to expand the dynamic range of the device over the N-100 device and to include a 16 bit microprocessor manufactured by Intel Corporation, Model No. 8088. The N-100 oximeter uses an 8 bit microprocessor manufactured by Intel Corporation, Model 8085. The N-200 oximeter includes software for controlling the microprocessor to perform the operations of the preferred embodiment of the time domain analysis techniques of present invention in addition to the conventional oximeter functions, and has some structure and processing methods that are unrelated to the present invention, and therefore are not discussed herein. The software could be modified to perform any of the other time domain or frequency domain analysis techniques of the present invention.

BRIEF DESCRIPTION OF THE DRAWINGS

FIGS. 7A, 7B, and 7C are detailed circuit schematics of the digital signal processing section of FIG. 1.

FIG. 10 is a flow chart for the frequency domain optical pulse processing of this invention.

FIGS. 10a, 10b, 10c, 10d, and 10e are graphical representations of of the processing of the optical signals.

DETAILED DESCRIPTION OF THE PREFERRED EMBODIMENT

Figure 1A:
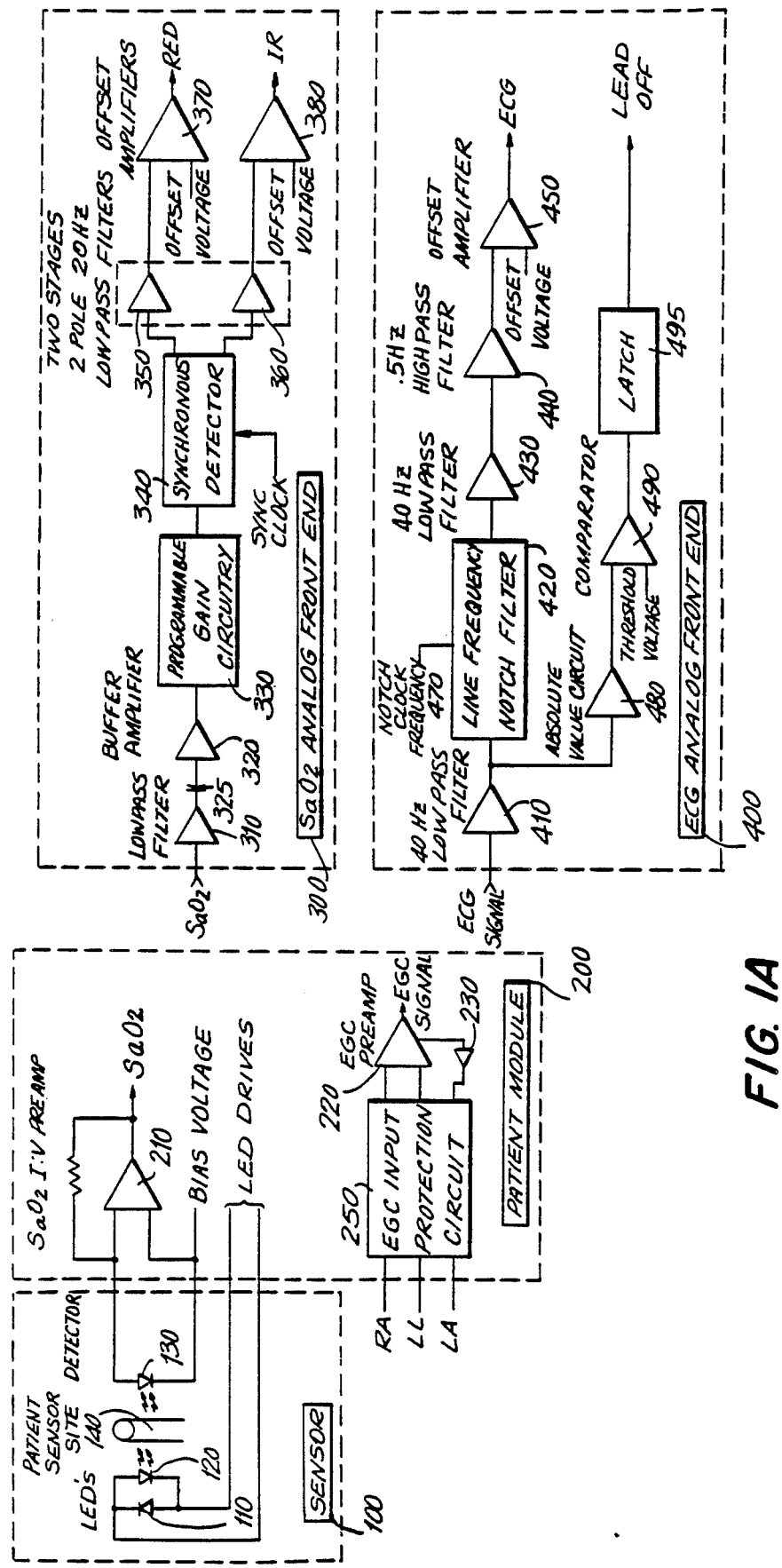
FIGS. 1A and 1B are block diagrams of the apparatus of this invention and the apparatus associated with the present invention.
Figure 1B:
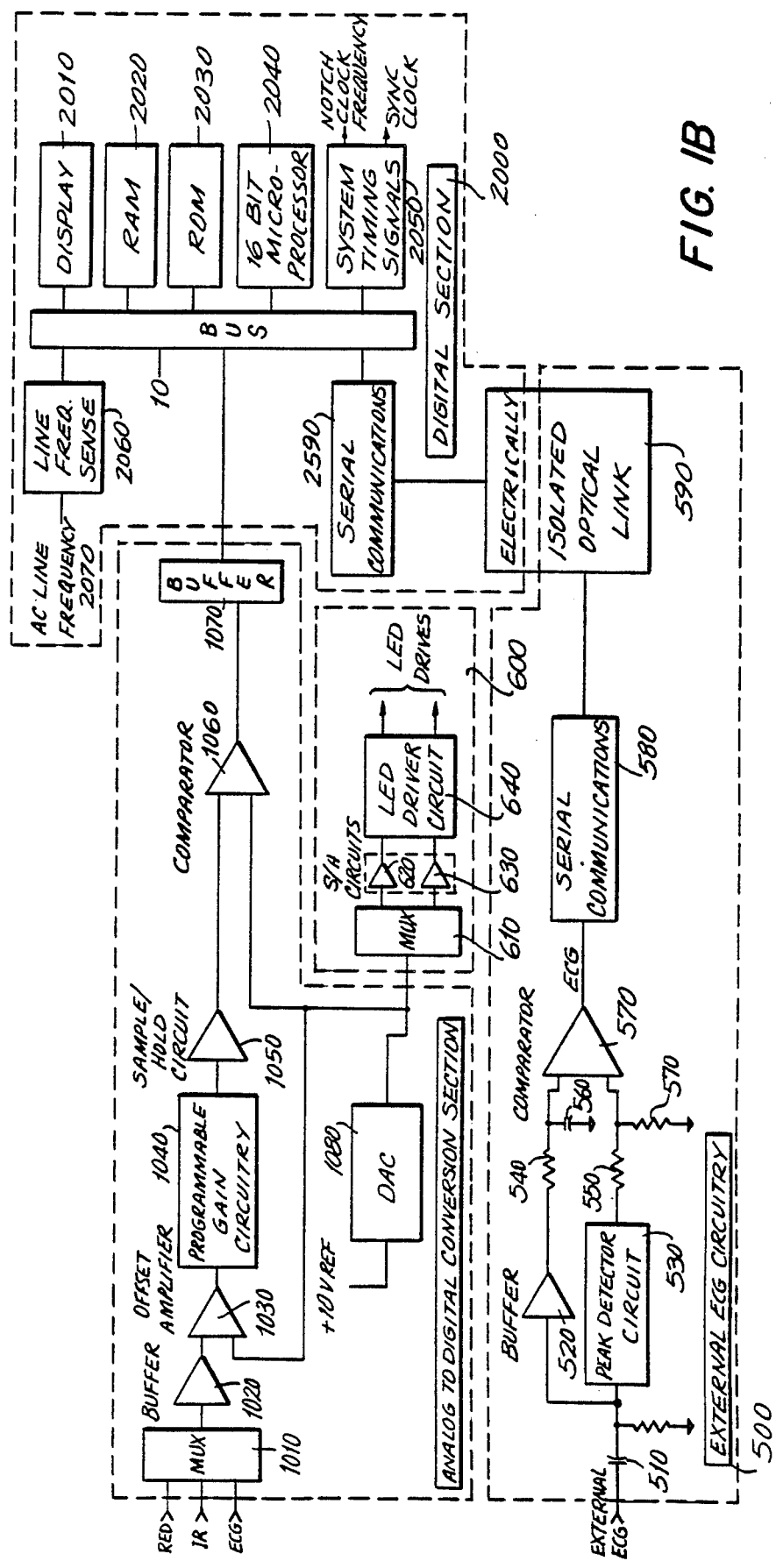

Referring to FIG. 1, the preferred embodiment of the present invention relates to the apparatus for processing the detected analog optical signal and the analog ECG signal and comprises portions of analog to digital conversion section ("ADC converter") 1000 and digital signal processing section ("DSP") 2000, including the software for driving microprocessor 2040, which processes the digitized optical signals and ECG signals to determine the oxygen saturation of hemoglobin in arterial blood. Associated with the invention, but not forming a part of the invention, is the apparatus for obtaining the detected analog optical signals and the analog ECG signals from the patient that is part of or is associated with the commercially available Nellcor N-200 Pulse Oximeter. Such apparatus include plethysmograph sensor 100 for detecting optical signals including periodic optical pulses, patient module 200 for interfacing plethysmograph sensor 100 and the conventional ECG electrodes with saturation analog front end circuit 300 and ECG analog front end circuit 400 respectively, saturation analog circuit 300 for processing the detected optical signals into separate red and infrared channels that can be digitized, and ECG anlog front end circuit 400 for processing the ECG signal so that it can be digitized. The N-200 oximeter also includes external ECG input circuit 500 for receiving an external ECG signal and processing the signal so that it is compatible with the N-200 processing techniques (as explained below), LED drive circuit 600 for strobing the red and infrared LEDs in plethysmograph sensor 100 at the proper intensity to obtain a detected optical signal that is acceptable for processing, and various regulated power supplies (not shown) for driving or biasing the associated circuits, as well as ADC 1000 and DSP 2000, from line current or storage batteries.

The associated elements are straightforward circuits providing specified functions which are within the skill of the ordinary engineer to design and build. The associated elements are briefly described here, and reference is made to the corresponding detailed schematics in the Figures and circuit element tables set forth below, to place the apparatus for using the present invention in its operating context in the preferred embodiment.

In the preferred embodiment, the invention requires three input signals, the two plethysmograph or detected optical signals (e.g., red and infrared) and the ECG signal of the patient. If analog signals are provided, they must be within or be adjusted by, for example, offset amplifiers, to be within the voltage input range for the ADC. In circumstances where the signals have been digitized already, they must be bit compatible with the digital signal processing devices, DSP.

The plethysmograph signal is obtained in a conventional manner for a non-invasive oximeter, typically by illuminating the patients tissue with red and infrared light in an alternating fashion, in the manner described above for the N-100 oximeter. Referring to FIG. 1, sensor circuit 100 has red LED 110 and infrared LED 120 connected in parallel, anode to cathode, so that the LED drive current alternately illuminates one LED and then the other LED. Circuit 100 also includes photodetector 130, preferably a photodiode, which detects the level of light transmitted through the patient's tissue, e.g., finger 140, as a single, analog optical signal containing both the red and infrared light plethysmographic, detected optical signal waveforms.

Figure 2A:
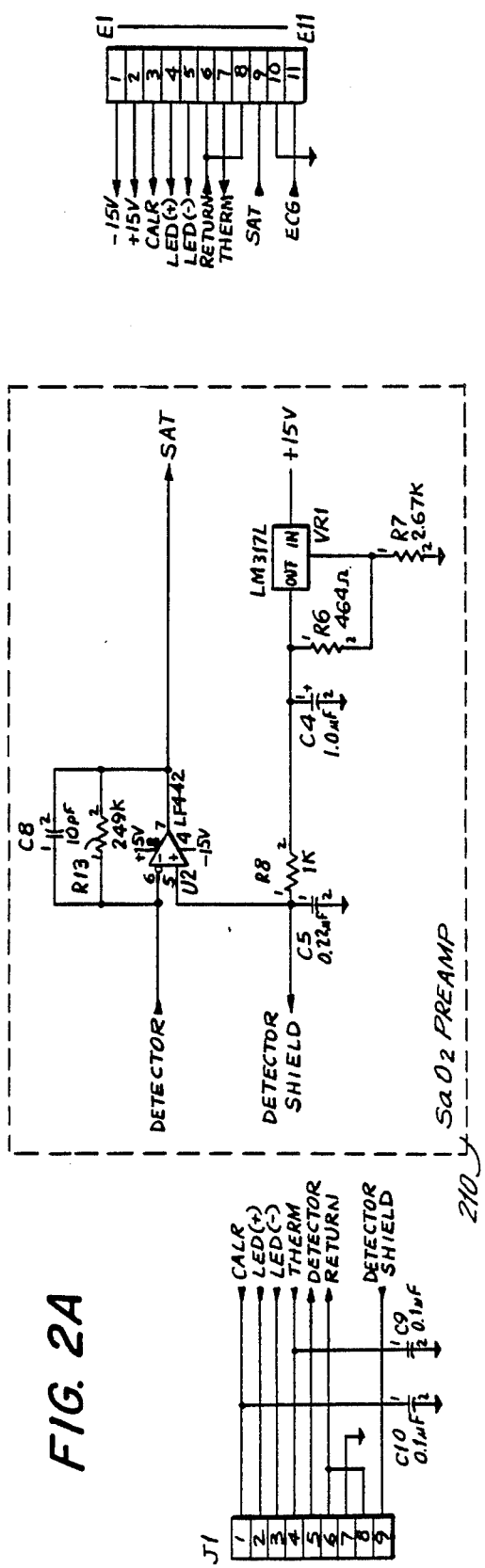
FIG. 2a is a detailed circuit schematic of the saturation preamplifier in the patient module of FIG. 1.
Figure 2B:
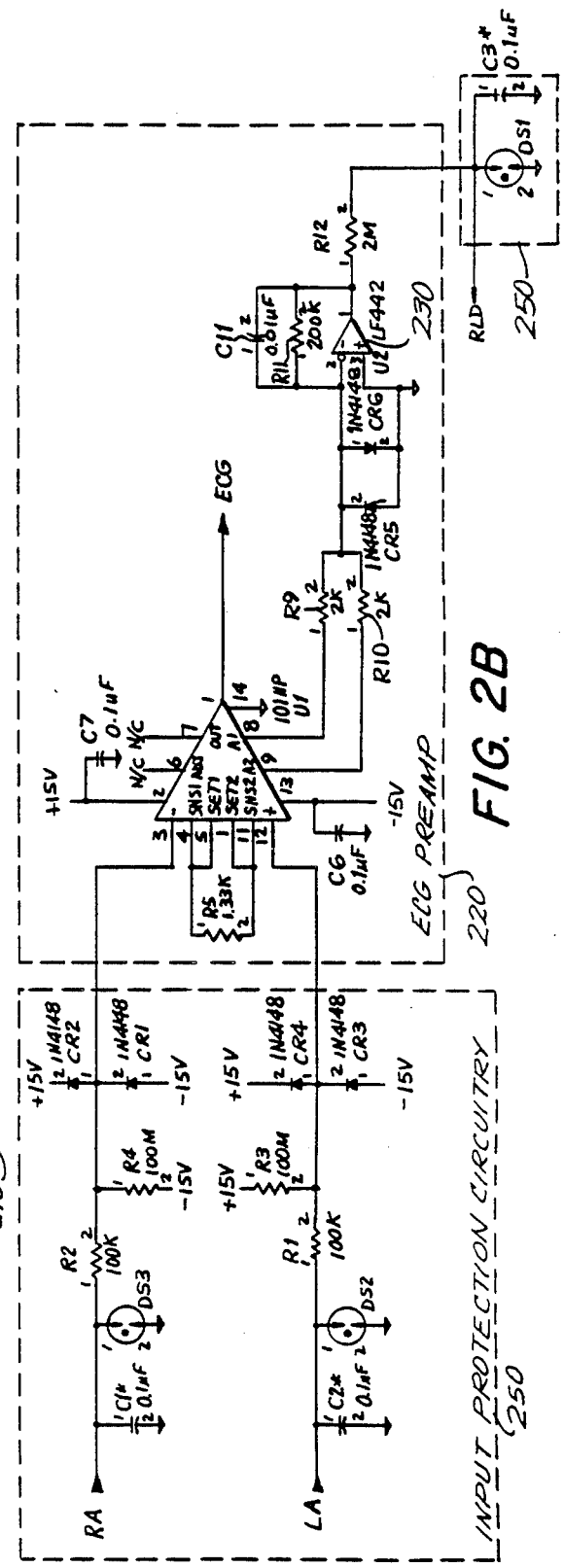
FIG. 2b is a detailed circuit schematic of the ECG preamplifier and input protection circuit in the patient module of FIG. 1.

Referring to FIGS. 1, 2a, and 2b, patient module 200 includes preamplifier 210 for preamplifying the analog detected optical signal of photodetector 130, ECG preamplifier 220 for preamplifying the analog ECG signal detected from the ECG electrodes that would be attached to the patient in a conventional manner, and protection circuitry 250 interposed between instrumentation amplifier 220 and inverter 230 and the three ECG signal leads, to prevent high voltage transients from damaging the ECG preamplifier electronics.

Preamplifier 210 may be an operational amplifier configured as a current to voltage converter, biased by a positive voltage to extend the dynamic range of the system, thereby converting the photocurrent of photodiode 130 into a usable voltage signal. ECG preamplifier 220 is preferably a high quality instrumentation amplifier which amplifies the differential signal present on the two ECG signal electrodes. The common-mode signal present on the two signal electrodes is inverted by inverter 230 and returned to the patient by the third ECG lead, effectively nulling the common-mode signals. A biasing network on the two ECG signal leads is provided to aid in the detection of when an ECG electrode lead becomes disconnected from patient module 200 or the patient. Patient module 200 also includes leads for passing the LED drive voltages to LEDs 110 and 120.

Figure 3A:
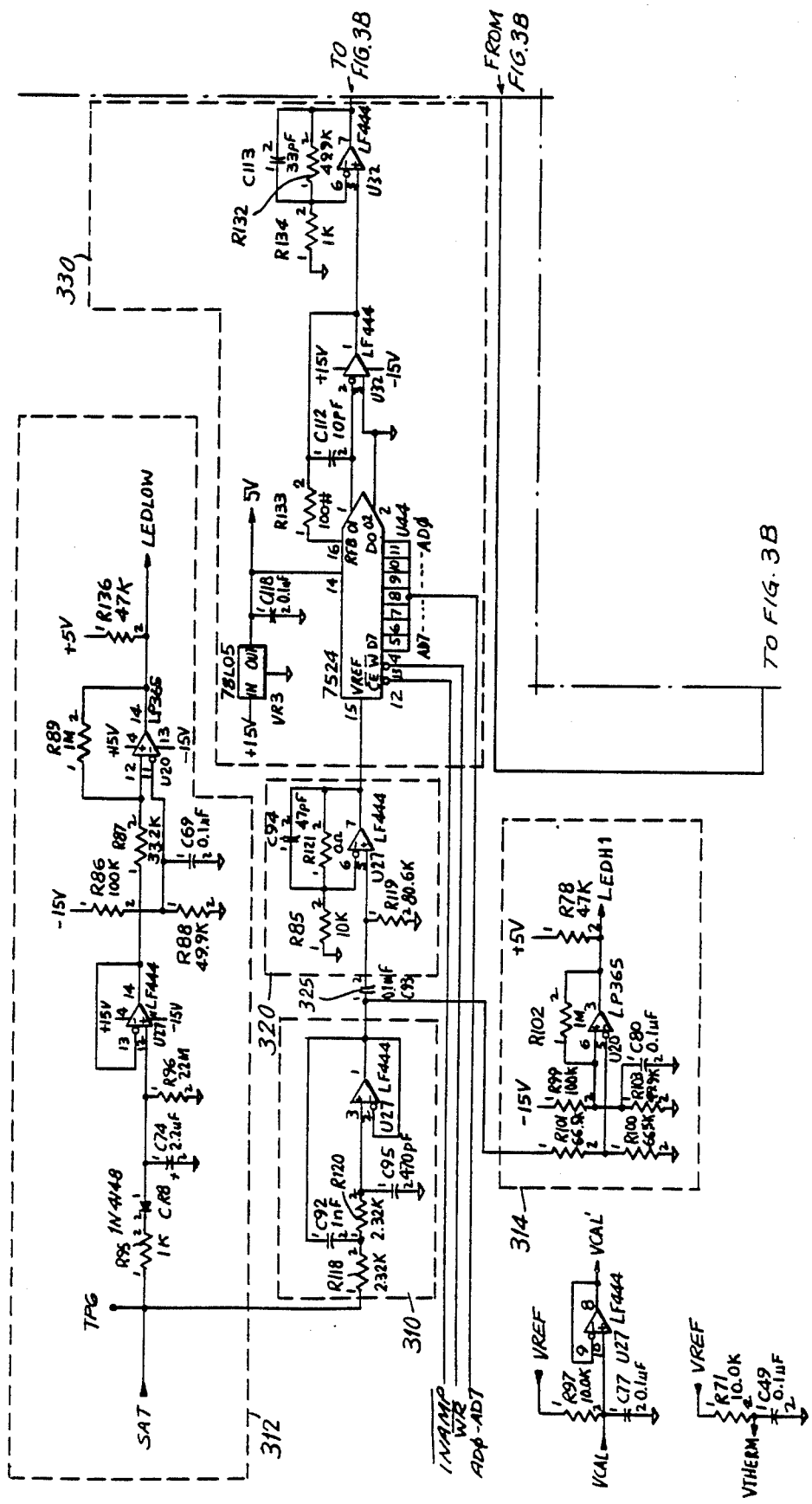
FIGS. 3A and 3B are detailed circuit schematics of the saturation analog front end circuit of FIG. 1.
Figure 3B:
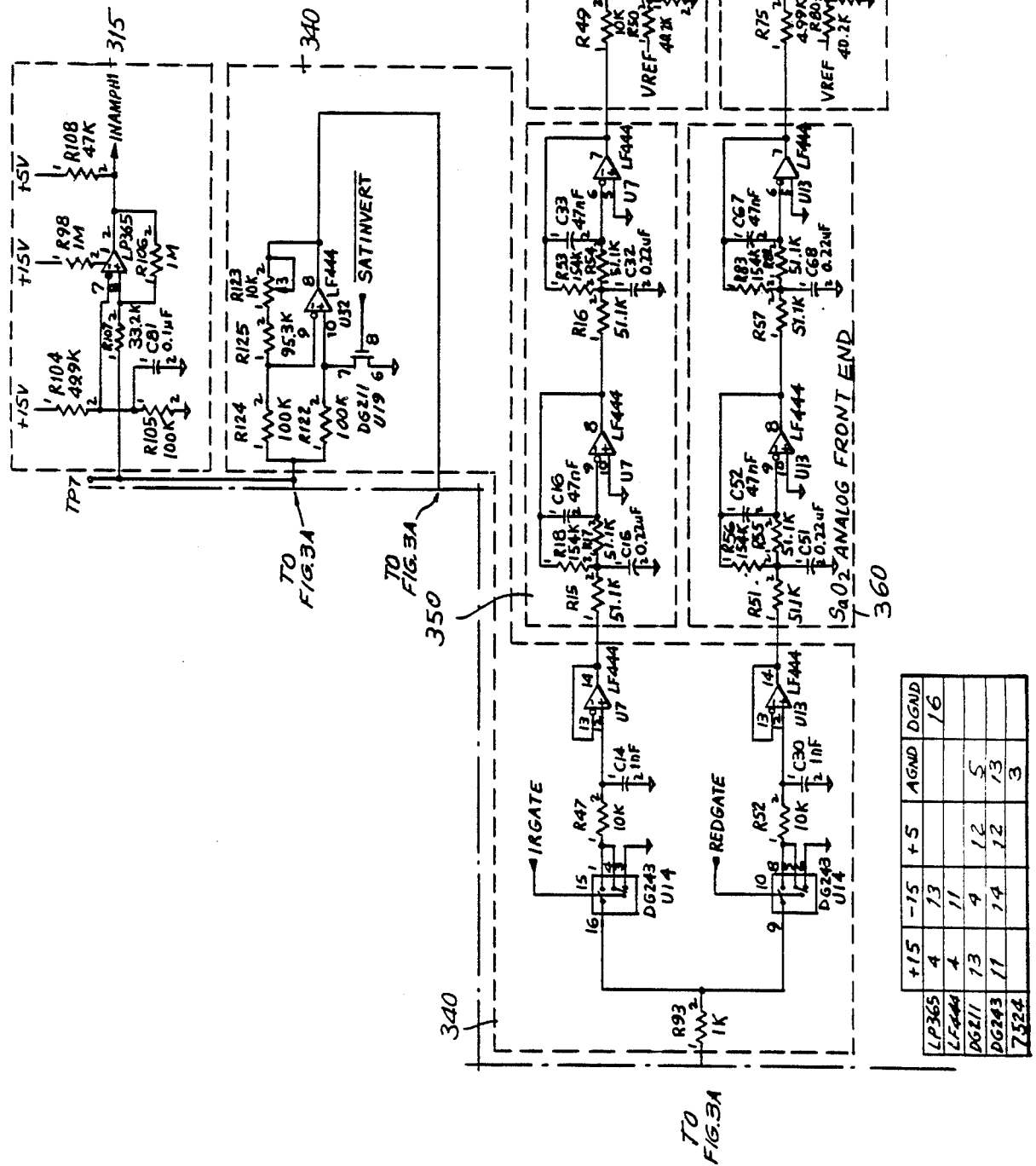

Referring to FIGS. 1 and 3, saturation analog front end circuit 300 receives the analog optical signal from patient module 200 and filters and processes the detected signal to provide separate red and infrared analog voltage signals corresponding to the detected red and infrared optical pulses. The voltage signal is passed through low pass filter 310 to remove unwanted high frequency components above, for example, 100 khz, AC coupled through capacitor 325 to remove the DC component, passed through high pass filter 320 to remove any unwanted low frequencies below, for example, 20 hertz, and passed through programmable gain stage 330 to amplify and optimize the signal level presented to synchronous detector 340.

Synchronous detector 340 removes any common mode signals present and splits the time multiplexed optical signal into two channels, one representing the red voltage signals and the other representing the infrared voltage signals. Each signal is then passed through respective filter chains having two 2-pole 20 hertz low pass filters 350 and 360, and offset amplifier 370 and 380. The filtered voltage signals now contain the signal information corresponding to the red and infrared detected optical signals. Additionally, circuits for use in preventing overdriving the amplifiers in saturation circuit 300 may be applied, for example, level-sensing circuits 312 and 314 (located after low pass filter 310) for indicating unacceptable LED drive current, and level sensing circuit 315 (located after programmable gain amplifier 330) for indicating unacceptable input amplifier gain setting.

Figure 5:
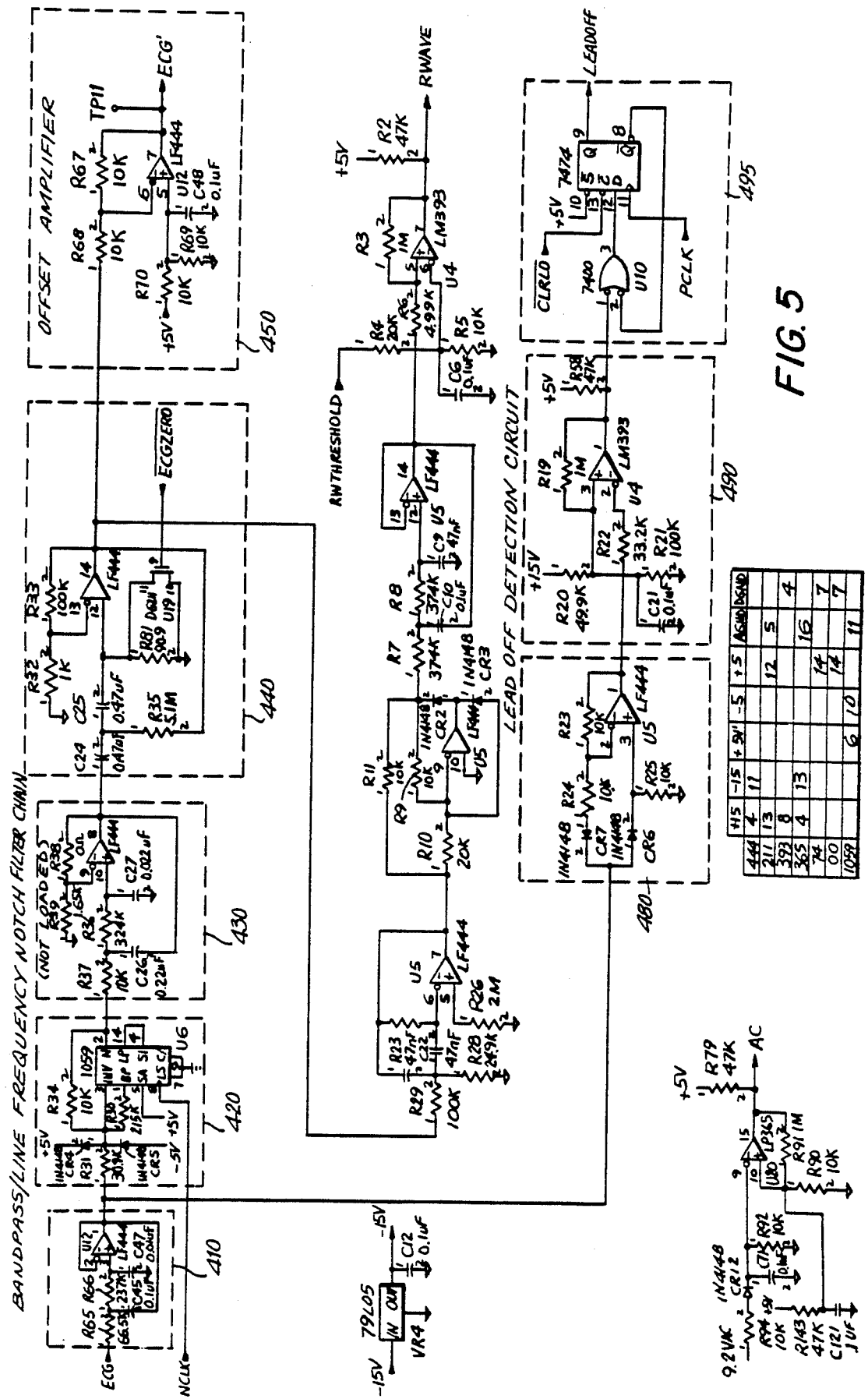
FIG. 5 is a detailed circuit schematic of the ECG analog front end circuit of FIG. 1.

Referring to FIGS. 1 and 5, ECG analog front end circuit 400 receives the preamplified ECG signal from patient module 200 and processes it for use with the present invention. The analog ECG signal is passed through 2-pole 40 hertz low pass filter 410 for removing unwanted frequencies above 40 hertz, and programmable notch filter 420 for removing unwanted line frequency components. Optionally, circuitry may be provided to measure the line frequency and to select an appropriate clock frequency for the notch filter. The ECG signal is then passed through low pass filter 430, preferably configured to remove further unwanted components above about 40 hertz, and in particular any frequency components that may have been generated by notch filter 420. Thereafter, the ECG signal is passed through 2-pole 0.5 hertz high pass filter 440 to remove any low-frequency baseline shifts present in the original ECG signal, and then passed through offset amplifier 450 to add an offset voltage that the voltage is within the input signal specifications of the analog to digital converter device and the complete waveform will be properly digitized.

It also is desirable to pass the signal output from low pass filter 410 into a circuit that detects whether or not the ECG signal is being detected to identify a "leads-off" condition. The signal voltage is passed through absolute value circuit 480 to take the absolute value of the low pass filter output voltage and sends the value to comparator 490. Comparator 490 compares the absolute value voltage to a reference threshold or range and, when the absolute value voltage is not within the acceptable range, comparator 490 changes state which change is input to latch 495, to indicate this condition to, for example, the microprocessor.

Figure 8:
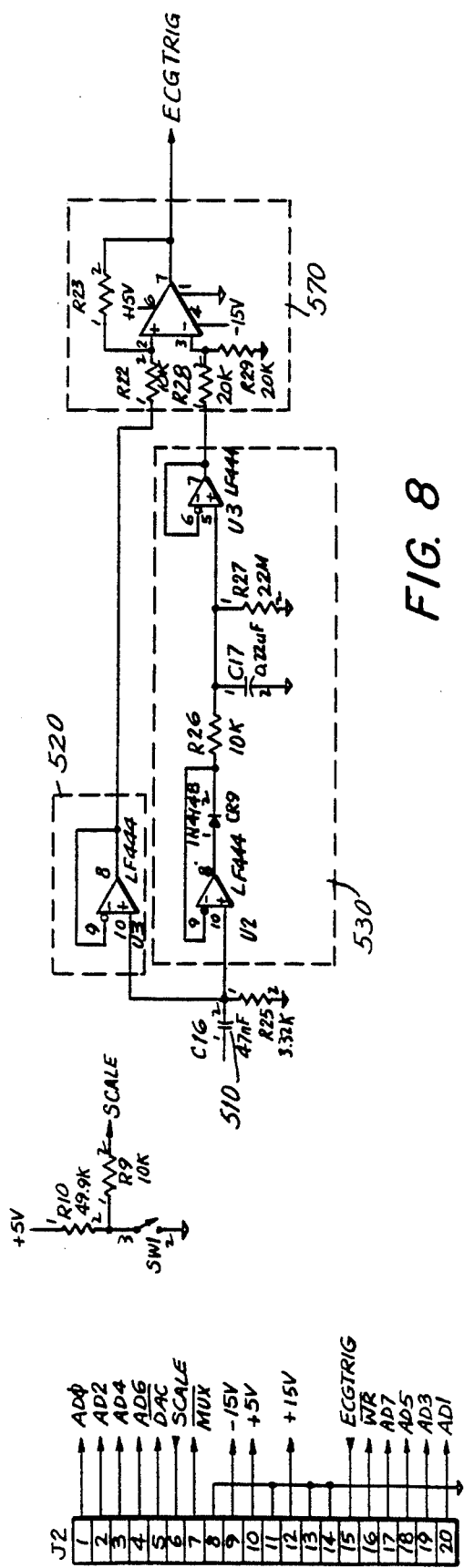
FIG. 8 is a detailed circuit schematic of the external ECG circuitry of FIG. 1.

Referring to FIGS. 1 and 8, the Nellcor N-200 device also is equipped with external ECG circuit 500 for receiving the ECG signal of a stand alone ECG detector device and processing the ECG signal so that it can be used with the N-200 oximeter and the present invention. Circuit 500 receives the external analog ECG signal, passes it across capacitor 510 to remove any DC offset voltage and then passes the signal through peak detection circuit 530. A portion of the AC coupled signal also is passed through buffer amplifier 520 and input to comparator 570. The held peak voltage is used as the reference threshold voltage that is fed to the other input of comparator 570 so that subsequent QRS complexes in the ECG signal that rise above the threshhold generate a trigger signal that is transferred to DPS 2000 by an electrically isolated optical serial communication link comprising serial driving opto-isolator 580, electrically isolated optical link 590, and corresponding serial driving opto-isolator 2590 in DSP 2000.

Figure 6A:
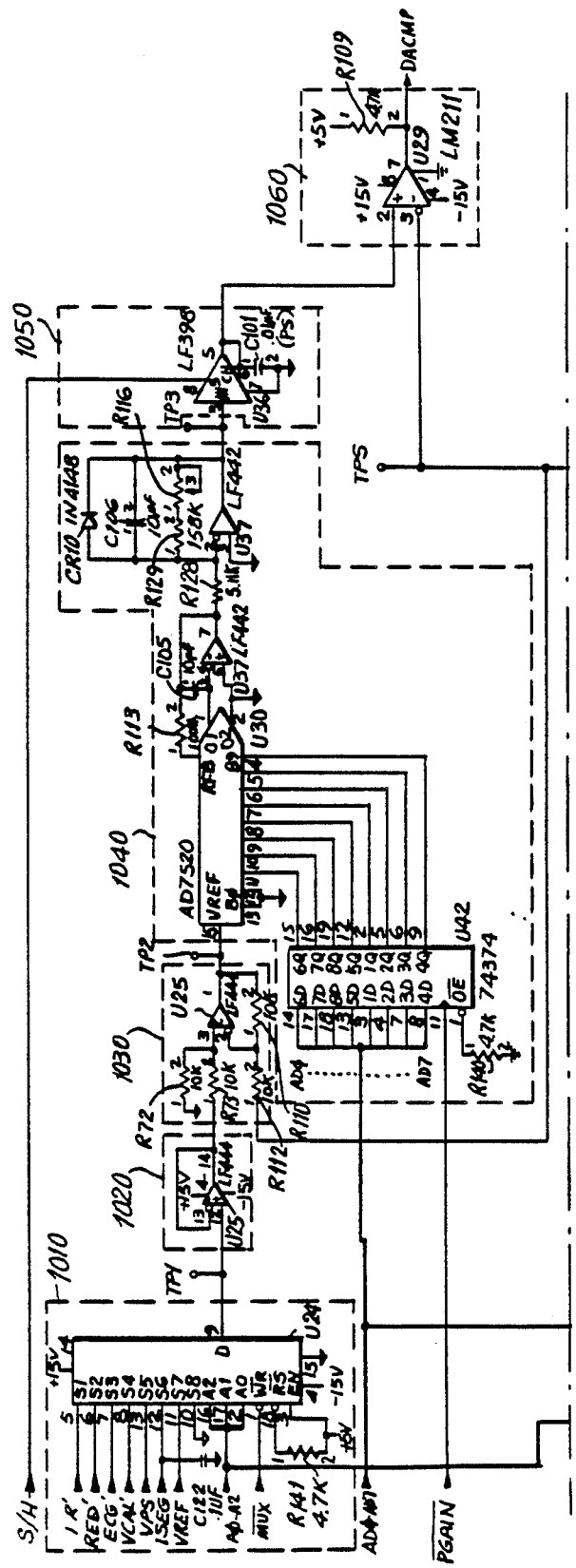
FIGS. 6A and 6B are detailed circuit schematics of the analog to digital converter section of FIG. 1.
Figure 6B:
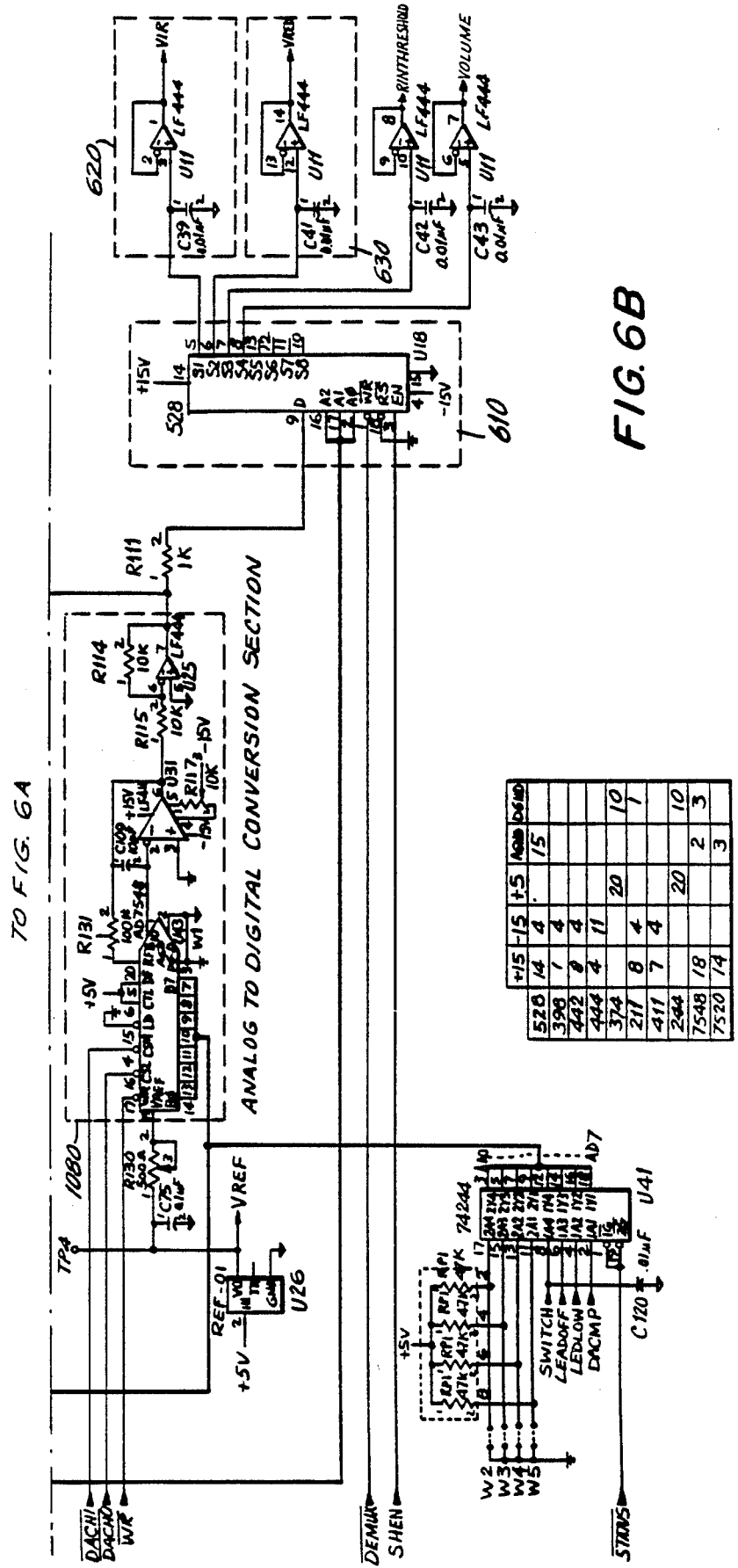

Referring to FIGS. 1 and 6, ADC 1000 provides the analog to digital conversions required by the N-200 oximeter. The aforementioned three voltage signals, the red detected optical signal, the infrared detected optical signal, and the ECG signal (preferably the ECG signal from patient module 200), are input to ADC 1000. These three signals are conventionally multiplexed and digitized by an expanded range 12-bit analog to digital conversion technique, yielding 16-bit resolution. The input signals are passed through multiplexor 1010 and buffer amplifier 1020. The converter stage includes offset amplifier 1030, programmable gain circuitry 1040 which allows a portion of the signal to be removed and the remainder to be further amplified for greater resolution, sample and hold circuit 1050, comparator 1060, and 12-bit digital to analog converter 1080. The buffered signal is passed through offset amplifier 1030 to add a DC bias to the signal wherein a portion of the signal is removed and the balance is amplified by being passed through programmable gain circuitry 1040 to improve the resolution. The amplified signal is then passed through sample and hold circuit 1050, the output of which is fed to one input of comparator 1060. The other input of comparator 1060 is the output of digital to analog ("DAC") converter 1080 so that when the inputs to comparator 1060 are the same, the analog voltage at the sample and hold circuit is given the corresponding digital word in DAC converter 1080 which is then stored in an appropriate memory device as the digitized data for the sample, and the next sample is sent to sample and hold circuit 1050 to be digitized.

Referring to FIGS. 1, 4, 6, and 7, DAC 1080 also generates the sensor LED drive voltages, under the control of microprocessor 2040, using analog multiplexor 610, which separates the incoming analog signal into one of two channels for respectively driving the red and infrared LEDs, having respective sample and hold circuits 620 and 630, and LED driver circuit 640 for converting the respective analog voltage signals into the respective positive and negative bipolar current signals for driving LEDs 110 and 120.

Alternate techniques of converting the analog signals to digital signals could be used, for example, a 16-bit analog to digital converter.

Figure 7A:
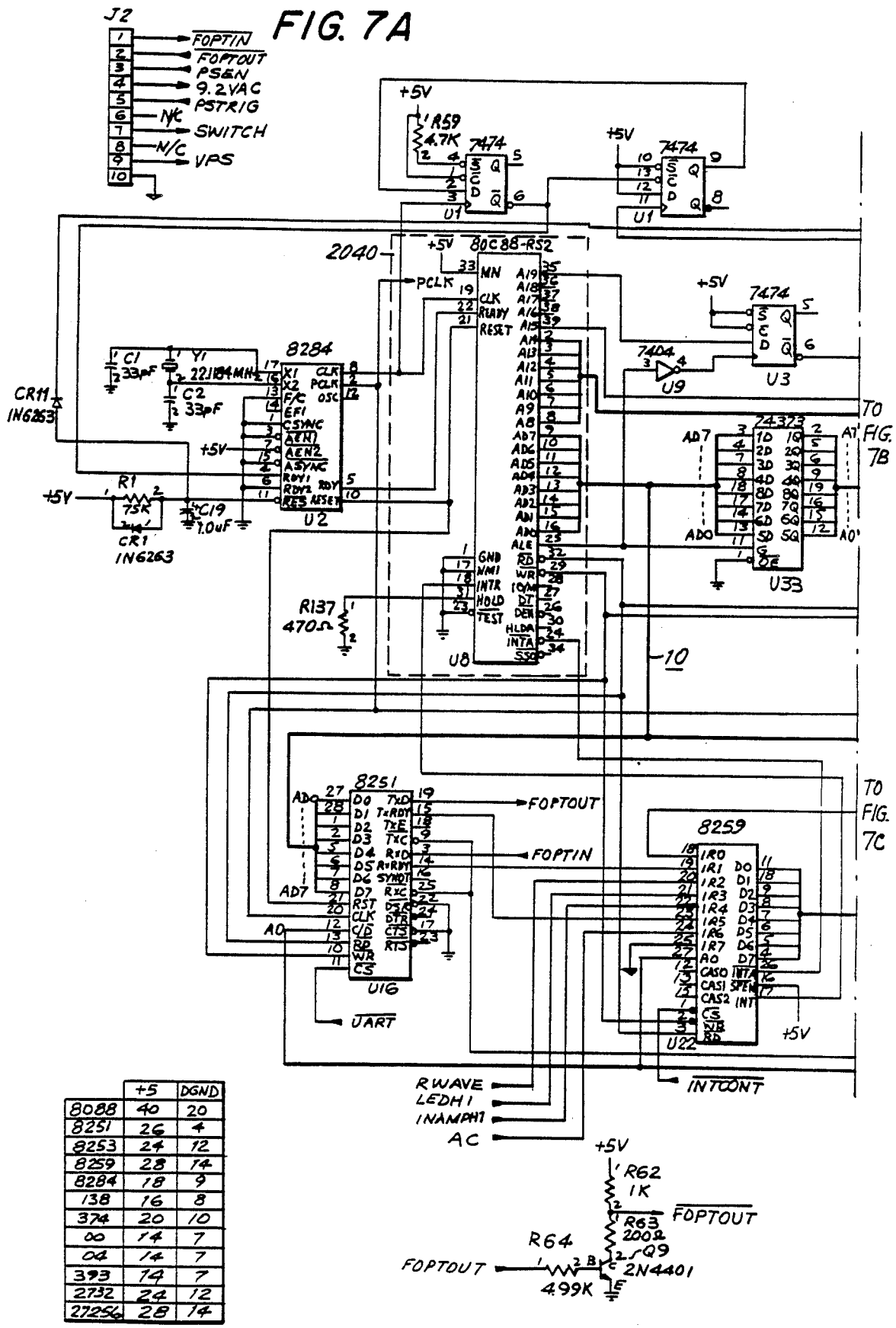
Figure 7C:
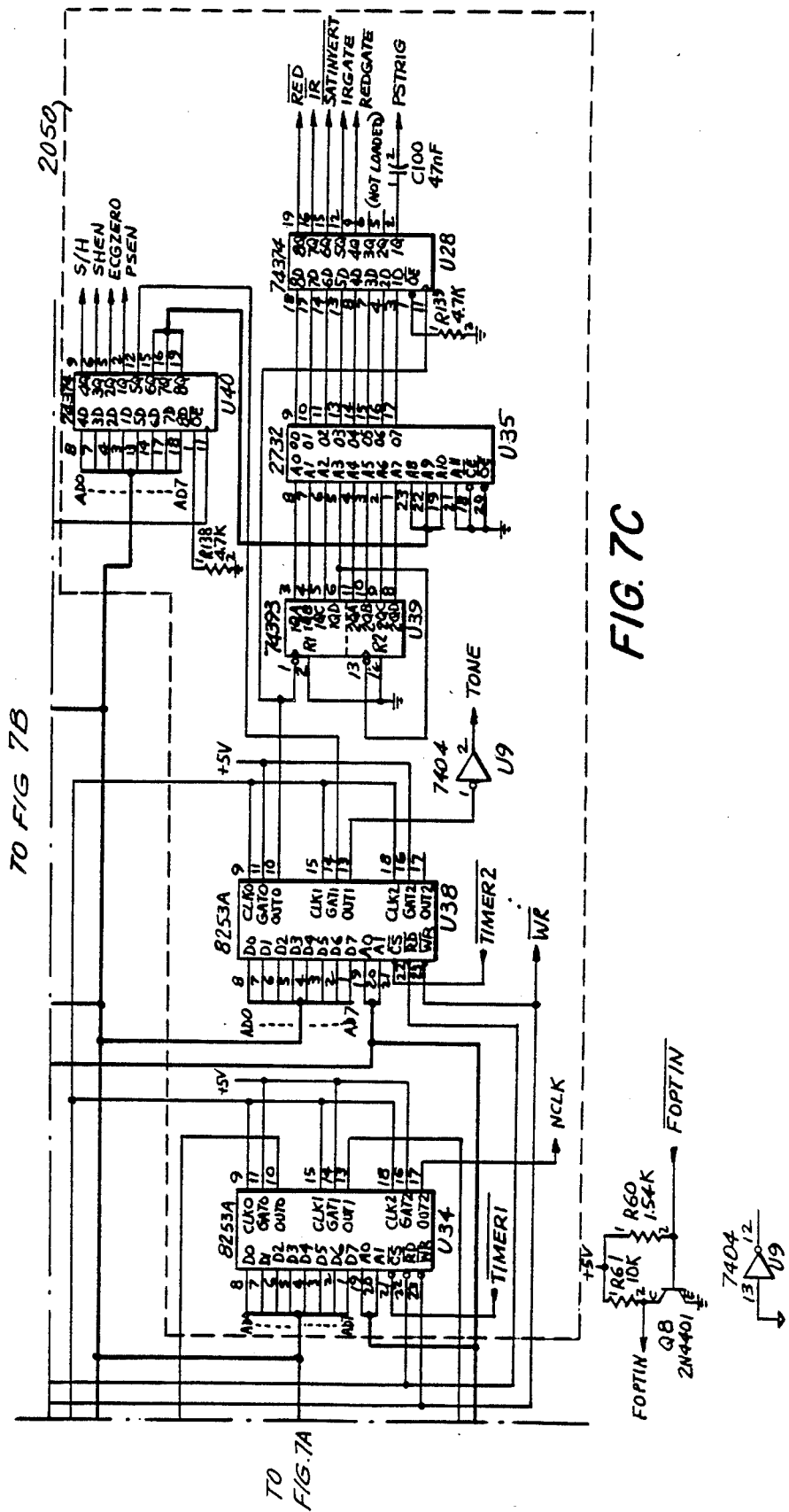

Referring to FIGS. 1 and 7, DSP 2000 controls all aspects of the signal processing operation including the signal input and output and intermediate processing. The apparatus includes 16-bit microprocessor 2040 and its associated support circuitry including data bus 10, random access memory (RAM) 2020, read only memory (ROM) 2030, a conventional LED display device 2010 (not shown in detail), system timing circuit 2050 for providing the necessary clock synchronizing and notch filter frequency signals. In the preferred embodiment, microprocessor 2040 is a model 8088 microprocessor, manufactured by Intel Corporation, Santa Clara, Calif. Alternate microprocessors may be used, such as any of model nos. 8086, 80186, and 80286, also made by Intel Corporation.

Referring to FIGS. 9a, 9b, 9c, 9d, 9e, and 9f and software Appendix A, the flowcharts for the software operation of the preferred embodiment are shown and described. Software appendix A is written in the standard programming language for Intel Model 8088 microprocessor devices.

Similar to the enhanced N-100 oximeter described in U.S. application Ser. No. 742,720, the N-200 oximeter incorporating the present invention is designed to determine the oxygen saturation in one or two modes, an unintegrated mode wherein the oxygen saturation determination is made on the basis of pulses detected in the optical pulse signal that are determined to be optical pulses in accordance with conventional pulse detection techniques, and in an ECG synchronization mode wherein the determination is based on the synchronized additive, composite optical signal information in accordance with the preferred embodiment of the present invention. In an alternate embodiment of the present invention, the determination of saturation in the unintegrated mode may be based on the frequency domain analysis techniques in accordance with this invention with or without the ECG synchronization feature of the time domain analysis techniques.

Figure 9A:
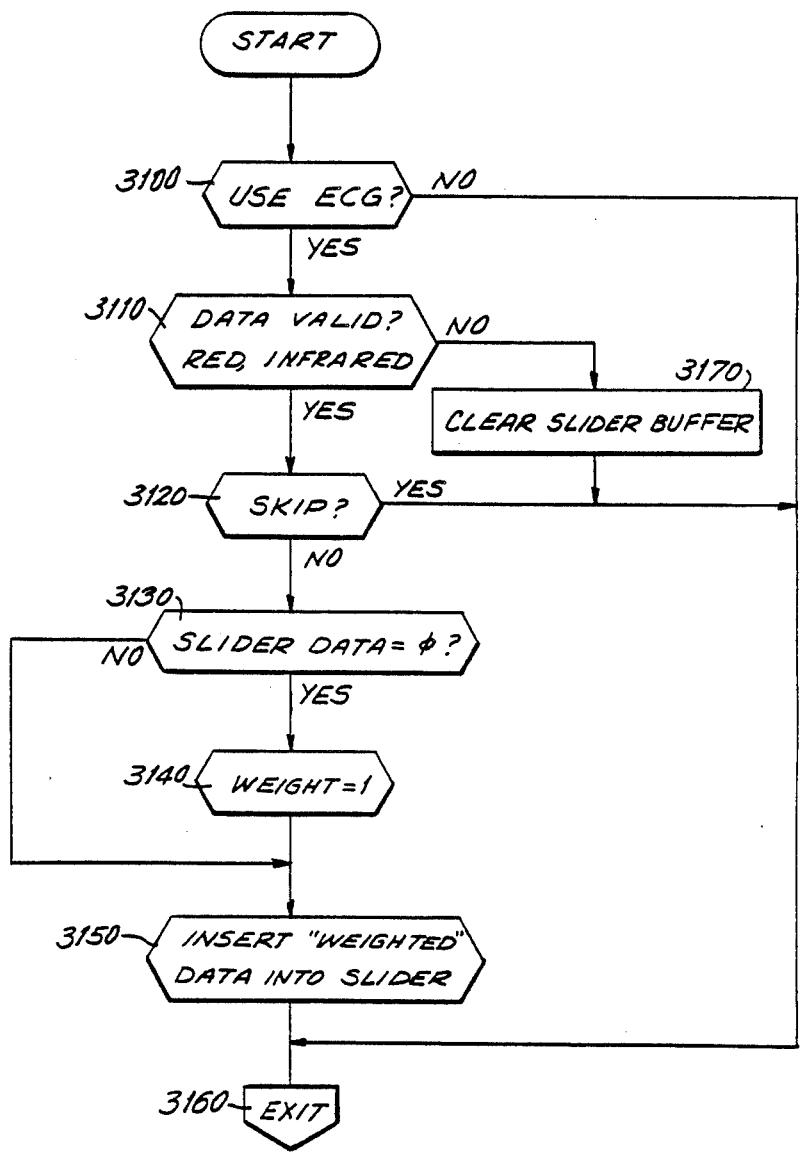
FIGS. 9a, 9b, 9c, 9d, 9e and 9f are flow charts for the time domain ECG and optical signal processing of this invention.
Figure 9B:
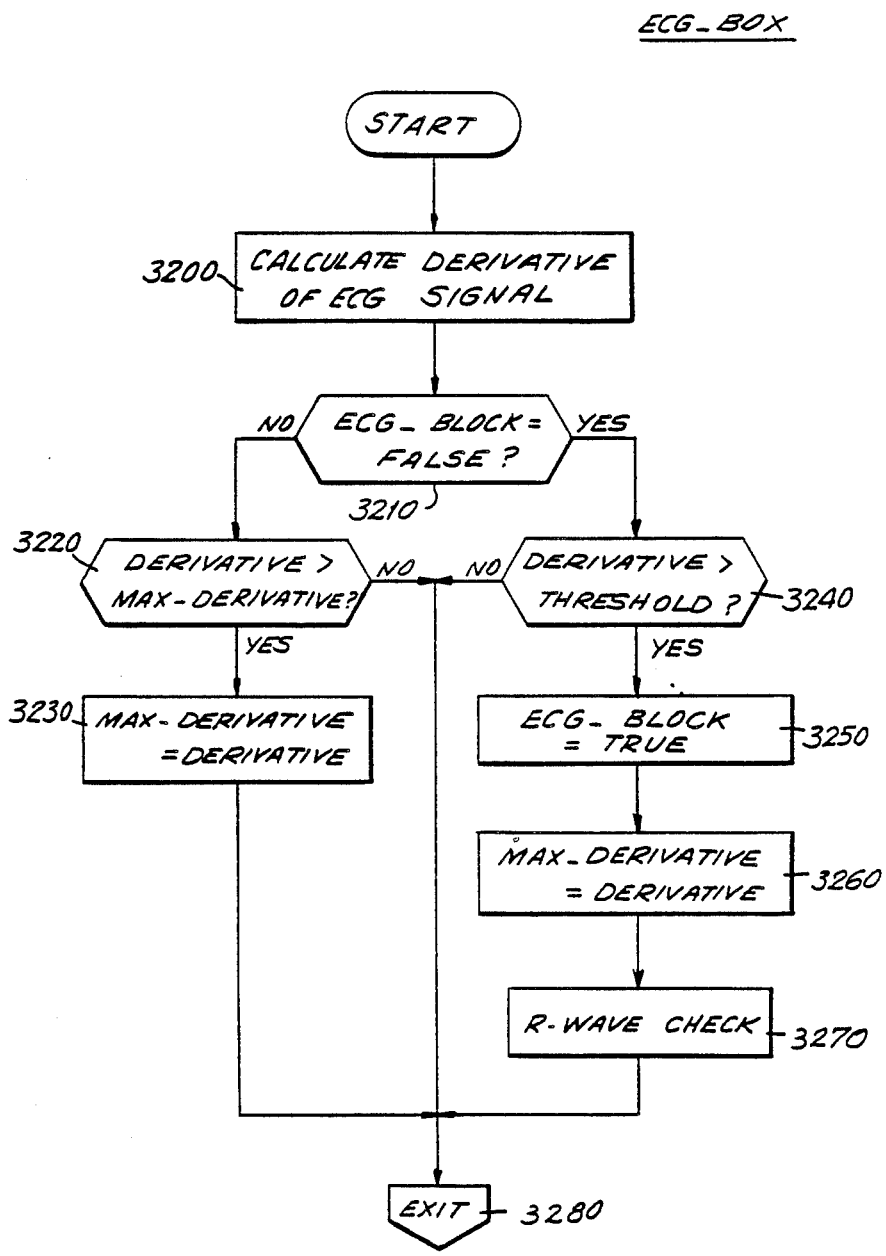
Figure 9C:
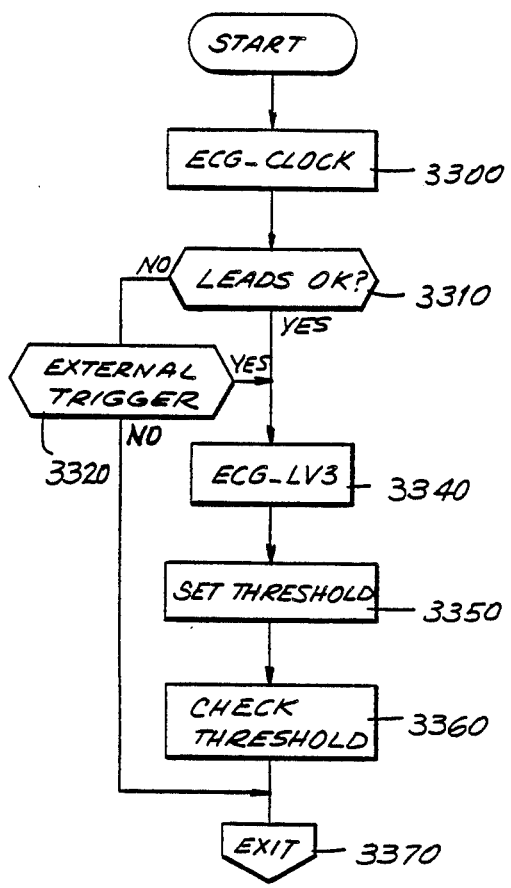
Figure 9E:
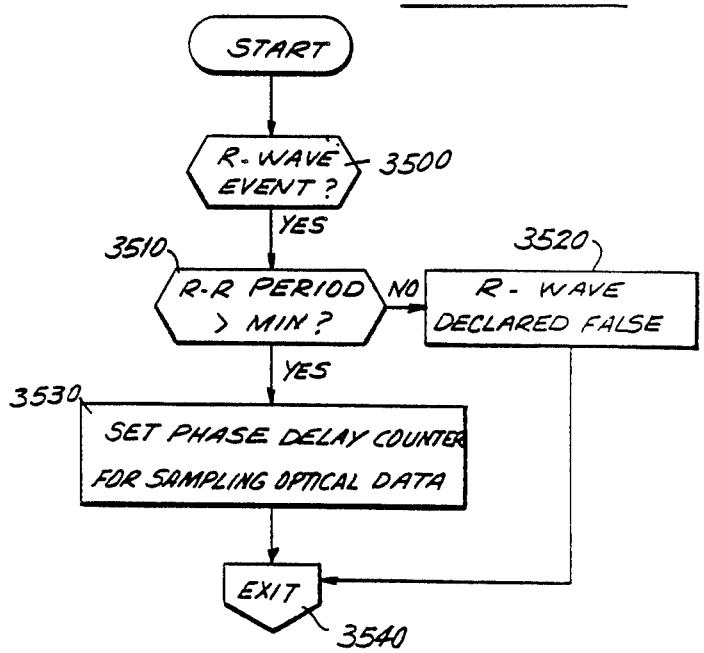
Figure 9D:
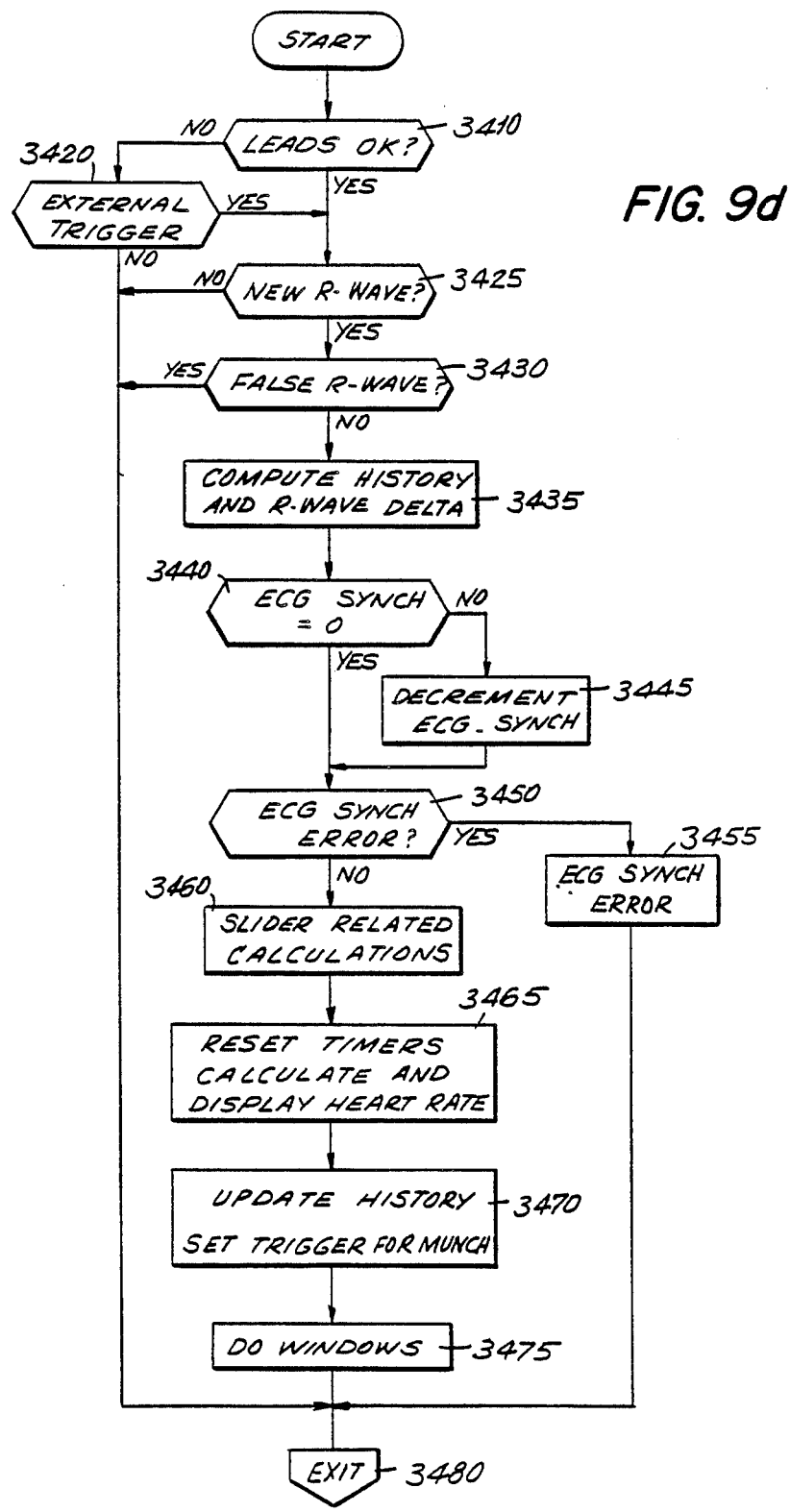
Figure 9F:
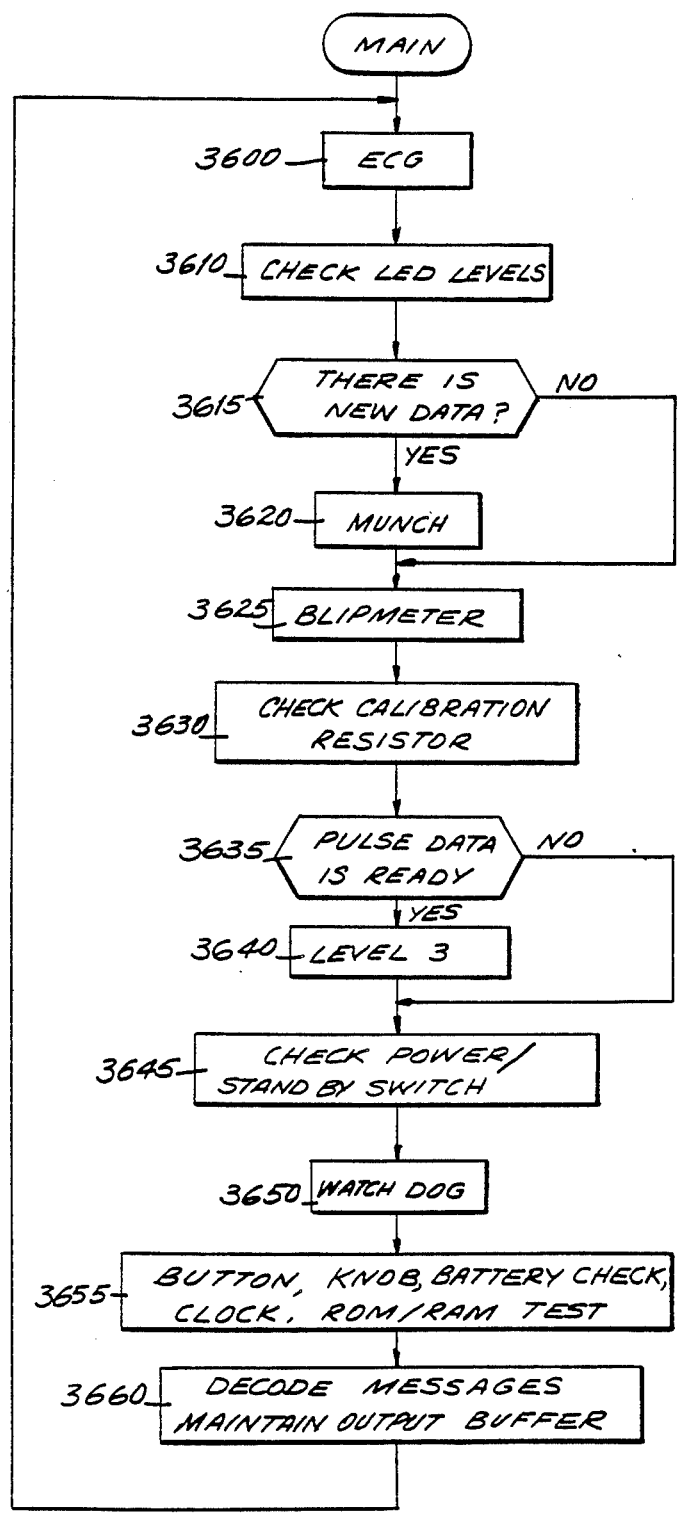

Referring to FIG. 9f, interrupt programs control the collection and digitization of incoming optical and ECG data. As particular events occur, various software flags are raised which transfer operation to various routines that are called from the Main Loop Processing routine. For example, Main Loop Processing calls the ECG routine at 3600, calls a routine that checks the LED levels at 3610 to make sure that there is enough and not too much light being transmitted, looks for the presence of new data at 3615, and if there is new data, calls the MUNCH routine at 3620, looks for processed pulse data at 3635 and passes such data to the Level3 routine that calculates saturation at 3640, and also runs various maintenance routines related to the oximeter functions which are not pertinant to the present invention, e.g., at 3625, 3630, 3645, 3650, 3655, and 3660 and are not discussed herein. The routines pertinent to the present invention are discussed here. Examples of similar and peripheral other routines may be found in the software appendix to application Ser. No. 742,720.

The detected optical signal waveform is sampled at a rate of 57 samples per second. When the digitized red and infrared signals for a given portion of detected optical signals are obtained, they are stored in a buffer called DATBUF and a software flag indicating the presence of data is set at 3615. This set flag calls a routine referred to as MUNCH at 3620, which processes each new digitized optical signal waveform sample. The MUNCH routine is called once per data point and determines pairs of maximum and minimum amplitudes in the detected signal data and presents the pairs to the Level3 routine. The Level3 routine evaluates the pair of maximum and minimum amplitudes determined by MUNCH, preferably utilizing conventional techniques for evaluating whether a detected pulse is acceptable for processing as an arterial pulse and performs the saturation calculation based on accepted pulses. The MUNCH routine first queries whether or not there is ECG synchronization. If there is ECG synchronization, then the MUNCH routine obtains from the SLIDER routine the enhanced pulse data on which the ECG synchronized saturation calculation will be made. If there is not synchronization, MUNCH obtains the sample stored in DATBUF on which the unintegrated saturation calculation will be made.

Referring to FIG. 9a, the SLIDER routine processes each new digitized sample portion of detected optical signal containing the optical pulse to create and maintain the enhanced composite red and infrared optical pulse waveforms, synchronized with the occurrence of successive ECG R-wave events.

The SLIDER routine first inquires whether there is an ECG signal at 3100. If there is not, then the routine aborts to exit at 3160 to main line operation. If there is an ECG signal, then the SLIDER routine continues and checks the validity of the optical signal at 3110. If the digitized sample in the buffer DATBUF for either of the red or infrared channels contains an invalid datapoint, the full content of the slider buffer (SLIDEBUF) is erased and the routine exited. The validity of the data is checked by looking for zeros placed in the buffer. Zeros are placed in the buffer when the signal level of the LEDs changes to permit the 20 Hz filters to settle, or if the signal exceeds the voltage limits of the processing electronics. This prevents processing of data known to be bad.

If the data are determined to be valid, then the SLIDER routine queries whether or not the data should be skipped at 3120. The optical signal sampling and data collection and processing of the sampled data are asynchronous processes. On occasion, the data buffer will have several unprocessed samples of data by the time the ECG R-wave event trigger occurs (described below). The R-wave event resets the slider buffer pointer to the begining of the slider buffer and marks the R-wave data sample in DATBUF. SLIDER will not process a data point if the slider buffer pointer is reset already to the beginning of the slider buffer and if the incoming data point was digitized in DATBUF before the data point marked by the R-wave event. Data in the DATBUF buffer prior to the R-wave event are to be skipped. If the data are to be skipped, SLIDER is exited.

If the data are to be processed, SLIDER calculates the updated value for the composite portion waveform sample as "slider_data" using the following formula:

$$\text{slider\_data} = \frac{(\text{WEIGHT} - 1)}{\text{WEIGHT}} \times \text{slider\_data} + \frac{1}{\text{WEIGHT}} \times \text{new-data}$$

where "WEIGHT" is the aforementioned fractional weighting fraction; "new_data" is the data point taken from the incoming sample in DATBUF, and "slider_data" is the pre-existing data point in the composite waveform in the slider buffer (SLIDEBUF) before the new data point is added and becomes the updated data point after the computation.

The computation is performed for each data point in DATBUF and any corresponding pre-existing data in the slider buffer. The occurrence of an R-wave event indicates the beginning of the heartbeat sample.

Before making the computation, SLIDER checks the slider buffer to see if there is any existing data at 3130. If there are data, then at 3150 SLIDER calculates the new value for the composite optical signal. If, however, the slider buffer is empty, then the WEIGHT value is assigned a numerial value of 1 at 3140, and subsequent new data points will be weighted 100% and the routine continues to calculate a new value for the composite optical signal at 3150 until the occurrence of the next R-wave event corresponding to the following heartbeat and portion of detected optical signal.

The SLIDER routine also performs other housekeeping chores for the processing associated with the slider buffer. First, in the preferred embodiment, the slider buffer is given a specific length and is able to store about three seconds worth of data. If, for whatever reason, the microprocessor does not receive or recognize an R-wave for more than three seconds, the pointer of the slider buffer is set to point to the last location and does not get incremented beyond that location. Subsequently processed samples are each placed in the last location of the buffer until the next accepted R-wave occurs or a time-out condition occurs. Time-out occurs when no further R-wave events are accepted for a predetermined time of, e.g., five seconds. After time out has occurred, MUNCH is notified the ECG synchronization is lost so that saturation calculations will be based only on the optical signals in DATBUF in the unintegrated mode.

Second, SLIDER continuously compares the updated composite waveform in the slider buffer to the previous composite waveform. If there is a large discrepancy, for example, during electromechanical disassociation, SLIDER takes immediate action to disregard the slider buffer data.

Third, to avoid corrupting the integrity of the waveform data in the slider buffer whenever the apparatus hardware or software triggers a change that influences the signal level of the detected optical signal or the optical pulse waveform, the content of the slider buffer is erased.

Referring to FIG. 9b, the ECG_BOX routine processes the ECG signal obtained through patient module 200 and analog ECG front end circuit to detect ECG R-wave events. The ECG signal is digitized every 5 msec and the digitized values are maintained in a circular buffer. The R-wave event is detected by observing the derivative of the ECG signal. The derivative is obtained at 3200 by application of the following algorithm:

$$\text{derivative\_ecg\_data}[n] = \text{abs}[-0.5 * \text{ecg\_data}[n-3] + 0.5 * \text{ecg data}[n-2] + 0.5 * \text{ecg\_data}[n-1] - 0.5 * \text{ecg\_data}[n]]$$

where "ecg_data[n]" is the digitized value for the ECG signal at sample location n and "abs[]" is the absolute value of the bracketed quantity.

The largest magnitude spike in the derivative buffer marks the R-wave. Because the algorithm generates the absolute value of the derivative, the derivative buffer contains two spikes very close to each other, one for the positive-going portion and the other for the negative-going portion of the R-wave. After the first spike is recognized, a timer ecg_block is set at 3250 to cause ECG_BOX to ignore the second spike.

Once the derivative value is obtained, and if the ecg_block timer is not active, then the derivative value is compared to the ECG threshold at 3240. The ECG threshold is a value that is set at about 75% of the previous maximum derivative value. If the derivative is greater than the threshold, ECG_BOX starts the ecg_block timer by setting ecg_block equal to true at 3250, and it replaces the maximum derivative value with the current derivative value at 3260, and calls the R-WAVE CHECKING routine at 3270. After the R-WAVE CHECKING routine is completed (as discussed below), ECG_BOX is exited at 3280.

If the derivative is not greater than the threshold, then ECG_BOX is exited at 3280. Once the ecg_block timer is activated, ECG_BOX will continue to calculate the derivative and compare the derivative to the prior maximum derivative value at 3220. If the calculated derivative is greater, then the maximum derivative value is set equal to the current derivative_ecg_data[n] at 3230 and the routine is exited. Otherwise the routine is exited.

Referring to FIG. 9e, the R-WAVE CHECKING routine receives the detected R-wave event at 3500 and checks the elapsed time since the last R-wave at 3510. If the elapsed time is less than the minimum internal time limit, preferably set at about 200 msec, the R-wave event is marked as a false R-wave event at 3520. If the elapsed time is greater than the minimum limit, then the routine starts a phase-delay timer/counter at 3530. The purpose of the phase-delay counter is to ensure that the optical data is placed into the beginning of the slider buffer after the optical signal minimum from the preceding pulse, but before the signal maximum of the next pulse. The preferred phase-delay period is 40 msec, based on the results of experimentation, and corresponds to the opening of the time window. It may be desirable to have a phase delay period that can be adjusted to accommodate varying optical signal detection conditions for different patients.

The Nellcor N-200 device is equipped with an external ECG input circuit as described above. The main line operating system controlling the operation of the N-200 device receives an interrupt when the external circuit 500 detects an R-wave. On receipt of the interrupt, a message is sent across isolated optical data transmission path 580-590-2590 (FIG. 1) to microprocessor 2040. The microprocessor then indicates to the ECG processing routines that an externally detected R-wave event has occurred, and the R-wave event is passed to the R-WAVE CHECKING routine. The external ECG analog circuit 500 thus performs the same function as the ECG_BOX routine, i.e., determination of an R-wave event followed by the R-WAVE CHECKING routine. The ECG_BOX routine is given priority over external ECG circuit 500 in passing signals to R-WAVE CHECKING.

Referring to FIG. 9c, the ECG routine provides for ECG synchronization, the initialization for slider buffer use, and various other tasks associated with ECG enhancement of the detected optical signal. The ECG routine is entered from the Main Loop Processing system (FIG. 9f, at 3600). Its first task is to maintain the ECG related counters/timers, such as ecg_block and phase-delay, at 3300. Next, at 3310, it checks whether or not the ECG leads from patient module 200 are present, and if not, it checks at 3320 for the presence of an external R-wave event trigger from external ECG circuit 500. If no R-wave event is detected, then the ECG routine is exited at 3370.

At this point in the processing, the main line processing system is receiving R-wave events, either from external circuit 500 or from patient module 200 and ECG_BOX. Regardless of the source of the R-wave event, the subsequent processing of the R-wave event is the same.

When an external R-wave event is detected or the ECG leads are present, the ECG routine calls the ECG_LV3 routine, shown in FIG. 9d. ECG_LV3 runs through a similar patient module 200 lead checking at 3410 or external circuit 500 trigger at 3420 as the ECG routine and if no R-wave event has occurred the routine is exited at 3480. If an R-wave event is detected, it is first checked at 3425 to determine whether or not it is a new R-wave event, and if it is not, the ECG_LV3 routine is exited. If it is a new R-wave event, 3430 uses the false R-wave flag (set by the R-WAVE CHECKING routine) to determine whether or not it was a true or false R-wave event. False R-waves will cause the routine to be exited at this point.

If the R-wave event is determined not to be a false R-wave, then the ECG-LV3 routine builds up a history of R-wave events based on the R-wave to R-wave interval at 3435. The criteria for accepting an R-wave includes the R—R period and the amplitude of the R-wave. For external ECG circuit 500 triggers, the R-wave event is a uniform pulse resulting from a comparison of the R-wave amplitude to a determined threshold signal.

After computing the R—R interval (or R—delta) and history, the ECG_LV3 routine checks to see if the ECG is synchronized at 3440. The ECG is synchronized after receiving the predetermined number, preferably five, acceptable R-wave triggers. For example, the ECG_synch counter is initialized at five. The routine tests the ECG_synch counter 3440 so that if it is greater than zero, the ECG is determined to be not synched, and then the ECG_synch counter is decreased by one at 3455. Thus, when the ECG_synch counter is at zero at 3440, indicating that the required prior five acceptable R-wave events have successively occurred, then it is determined that there is ECG synchronization and the device will proceed through MUNCH to calculate oxygen saturation based on the enhanced composite slider buffer calculations. Whether or not there is ECG synchronization, any R-wave event is checked again at 3450 against the history and R—R interval, if any, to determine whether there is an error in synchronization. If there is an error, the ECG_LV3 routine is exited. If there is no synchronization error, a routine is called at 3460 to compute the maximum length of time after which data in the slider buffer (SLIDEBUF) is disregarded. For example, if there is no prior R—R interval or history, then there will be no error for the first R-wave event. Subsequent true R-wave events will be compared to the prior R—R interval and history and if it appears to be a valid true pulse, then a routine is called to reset slider buffer pointers. However, the saturation calculation will be based upon the slider buffer data only after five R-waves have passed in synch and the synchronization flag is raised. Loss of synchronization resets the ECG_synch counter to five.

The ECG_LV3 routine also calculates the maximum length of the slider buffer based on the heart rate, which length is preferably 3 seconds or 2.5 times the determined R—R interval, whichever is the smaller. The ECG_LV3 routine also maintains the slider pointers and counters, resetting them or clearing them as necessary, resets the ecg timeout and bad R-wave counter, computes the displays heart rate based on the R—R interval at 3465, updates the history buffers and sets the trigger for the MUNCH routine to calculate pulse data for determining oxygen saturation based on the updated slider buffer data at 3470, sets and computes windows for selecting the portion of detected optical signal to be processed for each heartbeat, based on the history and the most recent data at 3475. In the preferred embodiment, the windows are set to open by the R-WAVE CHECKING routine phase-delay counter/timer 40 ms after the R-wave occurs and before the maximum optical pulse wave has occurred at the detection site, and set to close by the MUNCH routine after a maximum and minimum pair has been found.

Upon exiting ECG_LV3, the program returns to the ECG routine and checks the threshold of the derivative buffer of ECG_BOX. If the maximum derivative value is changed substantially, which indicates that the R-wave slope is changing, then the threshold is adjusted.

Referring to FIG. 10 and the software appendix B, the flow chart for the software operation of the frequency domain embodiment of the present invention are shown. Software appendix B is written is the Asyst computer language which is a commercially available language.

The routine begins at 4000 with the acquisition of 512 data points for each of the digitized red and infrared optical signals, which are shown graphically at FIG. 10a. At 4010, the complex data set, $f(t) = Red(t) + jIR(t)$, is formed. At 4020, the "D.C." component is formed by summing all of the data points, and the "D.C." component is then removed from the complex data set by subtraction at 4030, which is graphically shown at FIG. 10b. The resulting data is then decimated in time to 64 samples at 4040, which is illustrated in FIG. 10c, and the time decimated data is then processed by the Hamming Window function at 4050, which result is illustrated in FIG. 10d. Thereafter, the Fourier Transform is taken at 4060. The spectral components of the transform are shown in FIG. 10e. The Fourier Transforms of the red and infrared components are then calculated at 4070 in accordance with the aforementioned equations, and at 4080 the maximum value at the fundamental heart rate and the minimum value at the zero frequency are determined for each of the red and infrared transforms. The saturation ratio R is calculated as:

$$R = \frac{\frac{\text{peak at heartrate for red}}{\text{Re}(\text{"D.C."})}}{\frac{\text{peak at heartrate for infrared}}{\text{Im}(\text{"D.C."})}}$$

The minimum values for the red and infrared waveforms are taken from the respective real and imaginary components of the "D.C." component. Thereafter, the pulse data is declared ready and saturation is calculated in accordance with the foregoing saturation formula.

With each occurrence of the heartbeat, new data is acquired, the 512 data point set is updated and the routine operates to determine the saturation ratio R.

In the preferred embodiment, the blood constituent measured is the oxygen saturation of the blood of a patient. The calculation of the oxygen saturation is made based on the ratio of the pulse seen by the red light compared to the pulse seen by the infrared light in accordance with the following equation:

$$\text{Saturation} = 100\% \times \frac{BR2 - R(BR1)}{R(BO1 - BR1) + BR2 - BO2}$$

wherein
BO1 is the extinction coefficient for oxygenated hemoglobin at light wavelength 1 (Infrared)
BO2 is the extinction coefficient for oxygenated hemoglobin at light wavelength 2 (red)
BR1 is the extinction coefficient for reduced hemoglobin at light wavelength 1
BR2 is the extinction coefficient for reduced hemoglobin at light wavelength 2
light wavelength 1 is infrared light
light wavelength 2 is red light
and R is the ratio of the optical density of wavelength 2 to wavelength 1 and is calculated as:

$$R = \frac{\ln[I_{max2}/I_{min2}]}{\ln[I_{max1}/I_{min1}]}$$

wherein
$I_{max2}$ is the maximum light transmitted at light wavelength 2
$I_{min2}$ is the minimum light transmitted at light wavelength 2
$I_{max1}$ is the maximum light transmitted at light wavelength 1
$I_{min1}$ is the minimum light transmitted at light wavelength 1

The various extinction coefficients are determinable by empirical study as is well known to those of skill in the art. For convenience of calculation, the natural log of the ratios may be calculated by use of the Taylor expansion series for the natural log.

Circuit Tables

| REF # | CHIP | MFR PART # | Manufacturer | DESCRIPTION OF CHIP |
|---|---|---|---|---|
| FIG. 2 | | | | |
| 210 | U2 | LF442 | NATIONAL SEMICONDUCTOR | DUAL LOW POWER OP AMP |
| 220 | U1 | INA101HP | BURR BROWN | INSTRUMENTATION AMP |
| 230 | U2 | LF442 | NATIONAL SEMICONDUCTOR | DUAL LOW POWER OP AMP |
| FIG. 3 | | | | |
| 312 | U27 | LF444 | NATIONAL SEMICONDUCTOR | QUAD JFET OP AMP |
| 312 | U28 | LP365N | NATIONAL SEMICONDUCTOR | QUAD VOLTAGE COMPARATOR |
| 310 | U27 | LF444 | NATIONAL SEMICONDUCTOR | QUAD JFET OP AMP |
| 320 | U27 | LF444 | NATIONAL SEMICONDUCTOR | QUAD JFET OP AMP |
| 330 | U44 | MP7524LN | MICROPOWER | 8-BIT DAC |
| 330 | U32 | LF444 | NATIONAL SEMICONDUCTOR | QUAD JFET OP AMP |
| 330 | U32 | LF444 | NATIONAL SEMICONDUCTOR | QUAD JFET OP AMP |
| 315 | U20 | LP365N | NATIONAL SEMICONDUCTOR | QUAD VOLTAGE COMPARATOR |
| 340 | U32 | LF444 | NATIONAL SEMICONDUCTOR | QUAD JFET OP AMP |

-continued

Circuit Tables

Figure 4:
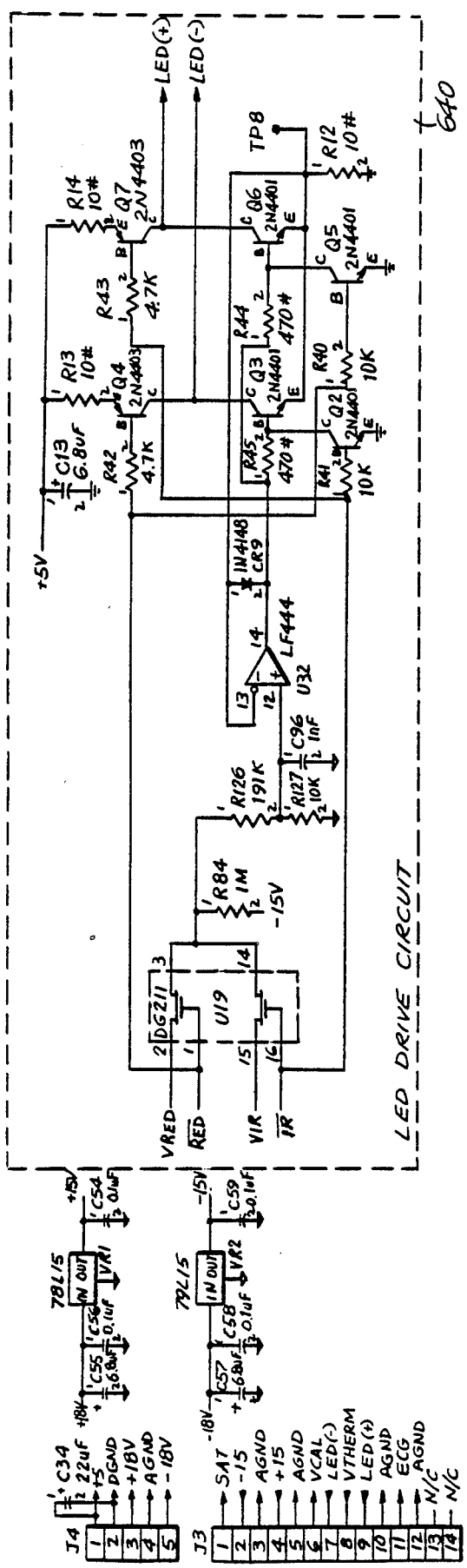
FIG. 4 is a detailed circuit schematic of the LED drive circuit of FIG. 1.

| REF # | CHIP | MFR PART # | Manufacturer | DESCRIPTION OF CHIP |
|---|---|---|---|---|
| 340 | U14 | DG243CJ | SILICONIX INCORPORATED | ANALOG SWITCH |
| 340 | U7 | LF444 | NATIONAL SEMICONDUCTOR | QUAD JFET OP AMP |
| 340 | U13 | LF444 | NATIONAL SEMICONDUCTOR | QUAD JFET OP AMP |
| 350 | U7 | LF444 | NATIONAL SEMICONDUCTOR | QUAD JFET OP AMP |
| 360 | U13 | LF444 | NATIONAL SEMICONDUCTOR | QUAD JFET OP AMP |
| 370 | U7 | LF444 | NATIONAL SEMICONDUCTOR | QUAD JFET OP AMP |
| 380 | U13 | LF444 | NATIONAL SEMICONDUCTOR | QUAD JFET OP AMP |
| 340 | U19 | DG211CJ | SILICONIX INCORPORATED | CMOS ANALOG SWITCH |
| FIG. 4 | | | | |
| 640 | U19 | DG211CJ | SILICONIX INCORPORATED | CMOS ANALOG SWITCH |
| 640 | U32 | LF444 | NATIONAL SEMICONDUCTOR | QUAD JFET OP AMP |
| FIG. 5 | | | | |
| 410 | U12 | LF444 | NATIONAL SEMICONDUCTOR | QUAD JFET OP AMP |
| 420 | U6 | LTC1059CN | LINEAR TECHNOLOGY | SWITCHED CAPACITOR FILTER |
| 430 | U12 | LF444 | NATIONAL SEMICONDUCTOR | QUAD JFET OP AMP |
| 440 | U12 | LF444 | NATIONAL SEMICONDUCTOR | QUAD JFET OP AMP |
| 440 | U19 | DG211CJ | SILICONIX INCORPORATED | CMOS ANALOG SWITCH |
| 450 | U12 | LF444 | NATIONAL SEMICONDUCTOR | QUAD JFET OP AMP |
| 480 | U5 | LF444 | NATIONAL SEMICONDUCTOR | QUAD JFET OP AMP |
| 490 | U4 | LM393N | NATIONAL SEMICONDUCTOR | VOLTAGE COMPARATOR |
| 495 | U10 | 74HC00 | TEXAS INSTRUMENTS | HIGH SPEED CMOS |
| 495 | U3 | 74HC74 | TEXAS INSTRUMENTS | HIGH SPEED CMOS |
| FIG. 6 | | | | |
| 1010 | U24 | DG528CK | SILICONIX INCORPORATED | OCTAL ANALOG SWITCH |
| 1020 | U25 | LF444 | NATIONAL SEMICONDUCTOR | QUAD JFET OP AMP |
| 1030 | U25 | LF444 | NATIONAL SEMICONDUCTOR | QUAD JFET OP AMP |
| 1040 | U38 | AD7524LN | ANALOG DEVICES | DAC |
| 1040 | U42 | 74HC374 | TEXAS INSTRUMENTS | HIGH SPEED CMOS |
| 1040 | U37 | LF442N | NATIONAL SEMICONDUCTOR | LOW POWER OP AMP |
| 1050 | U36 | LF398N | NATIONAL SEMICONDUCTOR | SAMPLE & H0LD OP AMP |
| 1060 | U29 | LM211P | TEXAS INSTRUMENTS | LOW OFFSET VOLTAGE COMPARATOR |
| 1080 | U43 | AD7548KN | ANALOG DEVICES | CMOS 12-BIT DAC |
| 1080 | U31 | LF411ACN | NATIONAL SEMICONDUCTOR | LOW OFFSET OP AMP |
| 1080 | U25 | LF444 | NATIONAL SEMICONDUCTOR | QUAD JFET OP AMP |
| 610 | U18 | DG528CK | SILICONIX INCORPORATED | OCTAL ANALOG SWITCH |
| 620 | U11 | LF444 | NATIONAL SEMICONDUCTOR | QUAD JFET OP AMP |
| 630 | U11 | LF444 | NATIONAL SEMICONDUCTOR | QUAD JFET OP AMP |
| FIG. 7 | | | | |
| | U2 | 82C84A-2 | NEC | CMOS 8 MHZ CLOCK GENERATOR |
| | U1 | 74HC74 | TEXAS INSTRUMENTS | HIGH SPEED CMOS |
| | U1 | 7HC74 | TEXAS INSTRUMENTS | HIGH SPEED CMOS |
| 2040 | U8 | MSM80C88RS-2 | OKI ELECTRIC | CPU 8MHZ, 125ns |
| | U3 | 74HC74 | TEXAS INSTRUMENTS | HIGH SPEED CMOS |
| | U33 | 74HC374 | TEXAS | HIGH SPEED CMOS |

-continued
Circuit Tables

| REF # | CHIP | MFR PART # | Manufacturer | DESCRIPTION OF CHIP |
|---|---|---|---|---|
|  | U9 | 74HC04 | TEXAS INSTRUMENTS | HIGH SPEED CMOS |
|  | U3 | 74HC74 | TEXAS INSTRUMENTS | HIGH SPEED CMOS |
|  | U9 | 74HC04 | TEXAS INSTRUMENTS | HIGH SPEED CMOS |
|  | U19 | 74HC00 | TEXAS INSTRUMENTS | HIGH SPEED CMOS |
|  | U9 | 74HC04 | TEXAS INSTRUMENTS | HIGH SPEED CMOS |
| 2030 | U21 | MBM27C512-25 | FUJITSU LIMITED | CMOS 64K × 8 ROM |
| 2020 | U15 | DS1242 | DALLAS SEMICONDUCTOR | CMOS 32K × 8 RAM |
|  | U23 | 74HC138 | TEXAS INSTRUMENTS | HIGH SPEED CMOS |
|  | U17 | 74HC138 | TEXAS INSTRUMENTS | HIGH SPEED CMOS |
|  | U19 | 74HC00 | TEXAS INSTRUMENTS | HIGH SPEED CMOS |
|  | U19 | 74HC00 | TEXAS INSTRUMENTS | HIGH SPEED CMOS |
|  | U16 | 82C51A | OKI ELECTRIC | CMOS UART |
|  | U22 | MSM82C59A-2RS | OKI ELECTRIC | CMOS INTERRUPT CONTROLLER |
| 2050 | U34 | MSM82C53-2 | OKI ELECTRIC | CMOS TRIPLE TIMER |
| 2050 | U38 | MSM82C53-2 | OKI ELECTRIC | CMOS TRIPE TIMER |
| 2050 | U9 | 74HC04 | TEXAS INSTRUMENTS | HIGH SPEED CMOS |
| 2050 | U39 | 74HC393 | TEXAS INSTRUMENTS | HIGH SPEED CMOS |
| 2050 | U35 | D273A | INTEL CORPORATION | 4096 × 8 ROM |
| 2050 | U40 | 74HC374 | TEXAS INSTRUMENTS | HIGH SPEED CMOS |
| 2050 | U28 | 74HC374 | TEXAS INSTRUMENTS | HIGH SPED CMOS |
| FIG. 8 |  |  |  |  |
| 520 | U3 | LF444 | NATIONAL SEMICONDUCTOR | QUAD JFET OP AMP |
| 530 | U2 | LF444 | NATIONAL SEMICONDUCTOR | QUAD JFET OP AMP |
| 530 | U3 | LF444 | NATIONAL SEMICONDUCTOR | QUAD JFET OP AMP |
| 570 | U7 | LM311N | NATIONAL SEMICONDUCTOR | VOLTAGE COMPARATOR W/STROBE |

Software
Appendix A

```
ECG:
;ECG MAIN "LOOP"
 ecg_00:
        mov     al,ecg_sw       ;check if to do any ECG
        or      al,al
        jnz     short ecg4 call    ecg_clock
        CALL    LEADS_CHK       ;can't do anything if leads off
        JNC     SHORT ECG1
        TEST    ECG_MODE,EXT_TRIG
        JNZ     SHORT ECG1      ;USING EXTERNAL TRIGGER IF SET
        cmp     ecgtmoflg,1
        je      short ecg0
        cmp     ecgsdly,0
        jne     short ecg0
        CALL    ECG_TMO
        mov     ecgtmoflg,1
ecg0:
        RET ECG1:
        CALL    ecg_lv3
        call    set_thresh      ;initial threshold adjustment
        call    chk_thresh      ;check and adjust threshold
ECG3:
        MOV     AX,ecdoidx
        ADD     AX,2
        AND     AX,ECG_B_MSK
        MOV     ecdoidx,AX
        RET
ecg4:
        cmp     ecg_sync,1
        je      short ecg5
        call    ecg_init1
ecg5:
        ret

; SUBTTL  ECG LEVEL 3
```

```
ECG_LV3:
;COMPUTE HEART RATE FROM ECG R_WAVE THIS ROUTINE FIGURES OUT WHETHER EKG
;AND/OR OXIMETER ARE SYNCED. IF EKG ONLY, THEN DO CONFIDENCE CHECKING ON
;PERIOD AND DISPLAY AND ALARM CHECK FOR THE HEART RATE;IF OXIMETER IS SYNCED,
;THEN DETERMINE Heart Rate BY THE R-WAVE PERIOD, IF THE CONFIDENCE IS GOOD.
;
;BEGIN CHECKING R-WAVE
        TEST    ECG_MODE,LEADS_OFF       ;if leads are on
        JZ      SHORT ECGLV31            ;  yes
        TEST    ECG_MODE,EXT_TRIG        ;  or external trigger in use
        JNZ     SHORT ECGLV31            ;  yes, continue
        JMP     LV3_RET                  ;else get out
ECGLV31:
        TEST    ECG_MODE,ECG_FLAG        ;if it's ok to do the rest of ecg_lv3
        JNZ     SHORT ECGLV32            ;  continue
        JMP     LV3_RET                  ;else get out
ECGLV32:
        cmp     fals_rwv,0               ;if false rwave
        je      ecglv32z                 ;  no, continue
                                         ;else
        mov     fals_rwv,0               ;  reset false r_wave counter
        mov     al,ecgsdly               ;  if 0<ecgsdly<4 then ecgsdly++
        cmp     al,0
        je      ecgex
        cmp     al,4
        jae     ecgex
        inc     ecgsdly
ecgex:  jmp     lv3_ret                  ; get out ecglv32z:
        CALL    HST_ECG                  ;COMPUTE HISTORY PARAMETERS -
                                         ;jump to level3's hstcmp routine
;dab ///
        mov     ax, dlyavg1              ;copy average r-max, r-slope
        mov     dlyavg1cpy, ax           ;to visible location
        mov     ax, dlyavg2
        mov     dlyavg2cpy, ax
;dab ///
        mov     ax, ecgmax               ;note interrupt issue: don't raise  ///
        sub     ax, ecgmin               ;flag until you've calculated delta ///
        mov     init_max_min,1           ;request next max_min pair          ///
        mov     ecg_delta, ax            ;                                   ///
ecglv32a:
        cmp     ecgsdly, 0               ;are we synced?
        Je      ecg_is_sync              ; yes, continue
        jmp     ecg_not_sync             ; no, get out
ecg_is_sync:
        cmp     ecg_syndly, 0
        je      ecgsyn0
        dec     ecg_syndly
ecgsyn0:
        XOR     AL,AL                    ;WE'RE SYNC'D
        MOV     ecg_SYNC,AL              ;SHOW ECG'S BEEN USED
        mov     ecgtmoflg,al
        MOV     CL,ECGLOST               ;show on the display
        CALL    CLRLIT2                  ; that ecg is on
        MOV     CL,ECGON                 ; again
        CALL    SETLIT2
        call    ecg_sync_err_ck          ;did sync error occur
        jnc     ecgsyn8                  ; no, continue
        jmp     ecg_sync_err             ; yes, get out
ecgsyn8:
        xor     ax,ax                    ;get ecg count
        xchg    ecgperiod,ax             ; and clear it at the same time
        mov     rrper,ax                 ;update r-r period
        call    calc_slide_tmo           ;calculate what slide_tmo should be ///
        call    do_slider_stuff          ;deal with slider and metermode junk ///

MOV     ECG_TMR,ECGTMO           ;PERIOD IS GOOD...RESET TIMEOUT
        MOV     BADECG,4                 ;RESET BAD ECG TICKET BOOK
        MOV     CX,rravg
        MOV     AX,ECGRATEFACTOR         ;CALC HEART RATE dab - use rravg not rrper ///
        CALL    COMRAT0
        CALL    DSPSR
        CALL    SEND_SAT
        XOR     AL,AC
        CMP     SYNFLG,AL                ;CHECK OXIMETER SYNC FOR ALARM CHECKING
        JNE     SHORT ecgsyn10           ;IF EQUAL, SYNC'D...DO WHOLE THING
        INC     ECGALMCHK                ;set semaphore to tell almchk
        CALL    ALMCHK                   ; ecg is calling it
        DEC     ECGALMCHK                ; then clear the semaphore
        JMP     ecgsyn11
ecgsyn10:
                                         ;ecg not synced
        INC     ECGALMCHK                ;set semaphore again for almchkb
        AND     ALMFLG,1 OR ECGTMOF OR PLSTMOF  ;MASK OFF Heart Rate ALARM
        CALL    ALMCHKB                  ; check if alarm should be on
        DEC     ECGALMCHK                ; then clear the semaphore
ecgsyn11:
        CALL    ECG_HUP                  ;HISTORY UPDATE FOR ECG
        CALL    SETIRIG
        call    clear_window_stuff
        call    do_windows
                                         ; accepted r-wave while synced.
LV3_RET:
lv3_ret2:
        mov     mch_flg, 1               ;reenable munch
        AND     ECG_MODE,NOT(ECG_FLAG)   ;disallow ecg_lv3 to be entered
        RET
```

```
ECG_not_sync:
ecgnsyn0:
        xor     ax,ax                   ;read ecg counter and reset
        xchg    ecgperiod,ax            ; it at the same time
        cmp     first_rwv_seen, 1       ;is this the first rwave seen
                                        ;since power up/ timeout?
        je      ecgnsyn0a               ;yes, ecgperiod is not yet valid
        mov     rrper, ax               ;no, save ecgperiod in r-r period
ecgnsyn0a:
        mov     first_rwv_seen, 0       ;
        call    ecg_nsync_err_ck        ;
        jc      ecg_not_sync_ex         ;an error occurred
        dec     ecgsdly                 ;ecgsdly will now be )= 0
        cmp     synflg, 0               ;synced on sat =) already displaying a pulse ///
        je      ecg_not_sync_ex         ;so skip the next part
        MOV     FRATN,255               ;SET HR FILTER LOW & CALC BASELINE HR
        MOV     CX,RRPER
        MOV     AX,ECGRATEFACTOR
        CALL    COMRAT0                 ;CALC BUT DON'T DISPLAY YET
ecg_not_sync_ex:
        test    ecgnotsyncerr, ecg_amp_err  ;don't update history if failed
        jnz     ecg_not_sync_ex1        ;peak-peak voltage test
        call    ecg_hup                 ;update ecg history
ecg_not_sync_ex1:
        JMP     LV3_RET ecg_sync_err:
        MOV     AL,BADECG
        DEC     AL
        Jns     ecgserr1                ;not yet out of coupons
        xor     ax,ax                   ;get ecg count
        xchg    ecgperiod,ax            ; and clear it at the same time
        mov     rrper,ax                ;update r-r period
        call    ecg_hup                 ;out of coupons, store it and get out
        jmp     short ecgserr2          ;
ecgserr1:
        MOV     BADECG,AL
        mov     ax, rravg               ;clear ecgperiod if it's too large
        add     ax, diflim + 10         ;last word in diflim is the
                                        ;difference limit for r-r period
        cmp     ax, ecgperiod
        jae     ecgserr2                ;rravg + rr diff lim ) ecgperiod - ok
        mov     ecgperiod, 0            ;
ecgserr2:
        jmp     lv3_ret                 ;

ecg_sync_err_ck:
        mov     bl, 0                   ;bl contains error codes
        test    ecg_mode,ext_trig       ;if external trigger do not check
        jnz     ecgserrk1               ;min amplitude
        mov     ax, ecg_delta
        cmp     ax,min_pp               ;check min amplitude requirement
        ja      ecgserrk1               ;fall through if passed
        or      bl, ecg_amp_err
ecgserrk1:
        push    bx
        CALL    ECG_D_CHK               ;CHECK DIF CODES
        pop     bx
        TEST    CURDIF,bit5             ;ECGBIT...CHECK IF FAILED PERIOD
                                        ;IF NZ, FAILED...DON'T CALC HR
        JZ      ECGserrk2               ;OUT OF BOUNDARY JUMP SOLVED
        or      bl, rr_per_err
ecgserrk2:
        mov     ecgsyncerr, bl          ;
        cmp     ecgsyncerr, 0
        je      ecgserrk3               ;jump if ecgsyncerr = 0
        stc                             ;return carry -) bl != 0
ecgserrk3:
        ret ecg_nsync_err_ck:
        mov     bl, 0                   ;bl contains error codes
        test    ecg_mode,ext_trig       ;if external trigger do not check
        jnz     ecgserrk1               ;min amplitude
        mov     ax, ecg_delta
        cmp     ax,min_pp               ;check min amplitude requirement
        ja      ecgnserrk1              ;fall through if passed
        or      bl, ecg_amp_err
ecgnserrk1:
        cmp     ecsdly, 1               ;only call ecg_v_chk just before
                                        ;about to sync
        jne     ecgnserrk2              ;
        push    bx
        CALL    ECG_v_CHK               ;CHECK DIF CODES
        pop     bx
        TEST    CURvar,bit5             ;ECGBIT...CHECK IF FAILED PERIOD
                                        ;IF NZ, FAILED...DON'T CALC HR
        JZ      ECGnserrk2              ;OUT OF BOUNDARY JUMP SOLVED
        or      bl, rr_per_err
ecgnserrk2:
        mov     ecgnotsyncerr, bl       ;
        cmp     ecgnotsyncerr, 0
        je      ecgnserrk3              ;jump if ecgnotsyncerr = 0
        stc                             ;return carry -) bl != 0
ecgnserrk3:
        ret
```

```
do_slider_stuff:
;** note - between here and the next set of stars, al contains slide_mode
;
        mov     al, slide_mode          ;for slider - if passed all checks, ///
        mov     elapse_hb, 0            ;                                    ///
        mov     elapse_sec, 0           ;                                    ///
        mov     bl, dattrig             ;skip the next few samples if
        cmp     dopidx, bl              ;dopidx is lagging where dipidx
        je      doslj0                  ;was when the rwave occurred
        or      al, shld_skip           ;set shld_skip and use_ecg to true. ///
doslj0:
        test    al, skip_next_rwv       ;skip this r wave?                   //
        jz      short doslj1            ;no                                  ///
        and     al, not (skip_next_rwv) ;yes                                 ///
        mov     slide_mode, al
        jmp     short doslj4
doslj1:
        or      al, use_ecg             ;
        test    al, first_time          ;                                    ///
        jz      short doslj2            ;                                    ///
        and     al, not (first_time)    ;                                    ///
        mov     slide_mode, al          ;first time, have clr_newbf clear
        mov     ax, 0                   ;entire newbuf
        jmp     short doslj3            ;
doslj2:
        mov     slide_mode, al          ;not the first time, have clr_newbf
        mov     ax, newiidx             ;reset 1st & 2nd newbuf ptrs
        mov     newiidx2, ax            ;copy newbuf position of ptr1 to ptr2
        mov     newiidx, 0              ;reset ptr1 tp start
        mov     newiidx2_on, 1          ;turn on ptr2
        jmp     short doslj4            ;and done
doslj3:
;**
        call    clr_newbf               ;                                    ///
        mov     newiidx, 0              ;                                    ///
        mov     newiidx2_on, 0          ;turn off newbuf ptr2    axp///
doslj4:
        ret                             ;

RWAVE_CHK:
;R-WAVE "INTERRUPT" -- CALLED BY THE ACTUAL I.S.R. (ABOVE) OR BY 2.5 mS ROUTINE
        PUSH    AX
        mov     al, ecg_sw              ;check if ok to continue
        or      al, al
        jnz     short intr_ret
RWV1:
        test    first_rwv_flg, 0ffh
        jz      rwv12                   ;jump if it is not the first r-wave
        mov     first_rwv_flg, 0        ;this is the first one so reset flag
        inc     find_max_req            ;go and search for max deriv value
        mov     find_cnt, TIME2000      ;set 2 sec timer
        jmp     intr_ret
rwv12:
        inc     block_flg               ;r-wave block is active
        XOR     AX, AX
        CMP     ECG200MS, AL            ;CHECK IF 200 mS TIMER IS ZERO
        JE      rwv14                   ;IF Z, >200 MS SINCE LAST R-WAVE, CONTINUE
                                        ;ELSE, RATE IS TOO FAST AND/OR TRIGGERED ON
                                        ;SOMETHING OTHER THAN AN R-WAVE.
        inc     fals_rwv                ;false R-wave counter
        jmp     short intr_ret
rwv14:
        MOV     ECG200MS, TIME200       ;SET 200 MS COUNTER
        mov     phase_dly, TIME40       ;start 40 msec delay having enough
                                        ;time to put Min in slider buffer
INTR_RET:
        mov     rwv_time_out, TIME5000  ;start 5 sec r-wave watch dog
        POP     AX
        RET CHK_TRIG:
;CALLED FROM 2.5 mS INTERRUPT TO CHECK STATUS OF EXTERNAL TRIGGER FLAG
;
        cmp     front_ecg_tmout, 0
        JNE     SHORT CHKTRIG_XIT       ;IF LEADS ARE ON
        MOV     AL, EXT_ECG_TRIG        ;GET STATUS OF TRIGGER
        OR      AL, AL
        JZ      SHORT CHKTRIG_XIT       ;NOT SET
        XOR     AL, AL
        MOV     EXT_ECG_TRIG, AL
        cmp     ext_ecg_blk, 0          ;check ext. rwave-block counter
        jne     chktrig_xit             ;probably a false trigger so jump
        mov     ext_ecg_blk, time50*2   ;init for 100 msec
        OR      ECG_MODE, EXT_TRIG
        mov     ext_trig_tmr, ext_trig_tmo      ;reset back panel timeout
        CALL    RWAVE_CHK
CHKTRIG_XIT:
        RET ;+------------------------------------------------------------------
;TITLE: ECGATOD
;FUNCTION: store the ecg signal value in the ecg ring buffer. If front
; panel ecg input flag is set, send ecg data to the powerbase.
; Increment the ecgsperiod and five_ms counters. Also sets the ignore
; rwave flag in ecg_mode if the ecg value isn't within allowable limits.
;
;REGS CHANGED:   AX,BX,CX
;CALLS:
;  adcvt, send_ecg, ecgbox, chktmrs
;------------------------------------------------------------------
```

```
ECGATOD:
        inc     ecgperiod               ;
        MOV     BX,OFFSET DGROUP: ECGTBL ;
        CALL    ADCVT                   ;get 12 bit dc voltage in dx
        MOV     BX,ECDIIDX              ;save index into ecg_buf
        push    bx                      ;for later
        CMP     DX,0FFFH                ;railed voltage ?
        jne     atod0                   ; no, continue to adjust voltage offset
        xor     dx,dx                   ; yes, no offset to adjust
        jmp     short atod_1            ; so go on
atod0:
        OR      DX,DX                   ;is dc voltage = 0 ?
        JE      SHORT ATOD_1            ;yes, do nothing
        ADD     DX,GNDV                 ;no, deal with p-gain offset
ATOD_1:
        MOV     OFFSET DGROUP: ECG_BUF [BX],DX ;load dc voltage
                                        ; into the ecg buffer cmp     init_max_min, 1         ;time to initialize ecg max and min ?
        je      atod_1a                 ;yes, go do it
                                        ;no, see if we have new ecg extremes
        cmp     dx, ecgmax              ;if a new dc max is found
        jbe     atod_1b                 ;
        mov     ecgmax, dx              ; update ecgmax
        jmp     atod_1c                 ;
atod_1b:
        cmp     dx, ecgmin              ;else if a new dc min is found
        jae     atod_1c                 ;
        mov     ecgmin, dx              ; update ecgmin
        jmp     atod_1c                 ;
atod_1a:                                ;if we are in a initializing mode
        mov     ecgmax, dx              ; load the new max
        mov     ecgmin, dx              ; and min
        mov     init_max_min,0          ; & clear the request to initialize
atod_1c:
        INC     BX                      ;point ecdiidx
        INC     BX                      ; to the next element
        AND     BX,ECG_B_MSK            ; in the ecg_buf
        MOV     ECDIIDX,BX              ; ring buffer
        INC     FIVE_MS                 ;count one more time running this routine
        mov     ax,ecgzv                ;get the absolute ecg signal
        add     ax,gndv                 ; i.e. Vecg = ecg noise gate + ground voltage
        sub     ax,dx                   ; delta is Vecg - Vecgzero
        jns     atod11                  ;
        neg     ax                      ;
atod11:
        cmp     ax,41                   ;is the ecg signal less than 100 mV
        jb      atod12                  ;yes, then it's inside noise range
        mov     front_ecg_tmout,TM10SEC ;no, re-trig front panel ecg timeout
        jmp     short atod13            ; and go send out the data
atod12:                                 ;ecg signal inside noise
        cmp     front_ecg_tmout,0       ;any front panel ecg input ?
        je      atod_15                 ;no, then nothing to send out
atod13: MOV     AX,DX                   ;send ecg data
        CALL    SEND_ECG                ;TO POWER BASE
atod_15:
        pop     bx                      ;retrieve index of value just converted
                                        ;that pointed to ecg_buf
        MOV     dx, OFFSET DGROUP: ECG_BUF [BX] ;if ecg value
        cmp     dx, max_ecg_lev         ; is not within
        jae     short atod_15a          ; the max and min
        cmp     dx, min_ecg_lev         ; of the allowable
        jbe     short atod_15a          ; ecg levels
        jmp     short atod_15b          ;
atod_15a:
        or      ecg_mode, ignore_rwv            ; next rwave
        mov     ignore_rwv_tmr, Ignore_rwv_time ; for a limited time
atod_15b:
        call    ecgbox                  ;make entry into parallel buffer ///
        call    chktmrs                 ;
        RET ECG_INIT:
        mov     ext_ecg_blk,0           ;init extern. rwave block counter
        MOV     ECGSDLY,4
ecgin0a:
        MOV     ECGPGN,1
        MOV     ECGOFV,0
        MOV     ECGCTR,2                ;sampling intrv=5 ms.
        MOV     ECGFQ,2
        AND     SH_PAT_SAV,ECGDSABL
        MOV     DECTAV,DELTA_MIN
        mov     front_ecg_tmout,TM15SEC ;init front panel timeout
                                        ;counter with 15 sec
ecg_init1:
        MOV     ecg_SYNC,1
;+---------------------------------------------------------------
;TITLE: ECG_TMO
;FUNCTION: ecg time out
ECG_TMO:
ECG_TMO_2:
        CMP     ecg_SYNC,1
        JE      SHORT TMO_3
        TEST    ECG_MODE,TMO_FLG
        JZ      SHORT TMO_4
        JMP     TMO_1
TMO_4:
        OR      ECG_MODE,TMO_FLG
TMO_3:
        mov     bl,ecgsdly
        cmp     ecgsdly,0
        jne     short tmo_3a
        mov     ecg1secalarm,1
```

```
tmo_3a:
        MOV     ECGSDLY,4
tmo_3a0:
        MOV     WINDOFAC,3                      ;START OUT AT 12.5%
        MOV     MCH_FLG,1                       ;ENABLE MUNCH ON TIMEOUT
        mov     ecg_syndly, 4                   ;dab ///
;since chktmrs will increment wintmr1 and 2 as long as winflg1 and 2 are
;zero, and since you don't want wintmr1 or 2 to begin counting
;until you're synced on ecg, initialize these variables to something
;non zero. dab ///
        mov     winflg1, 2                      ;
        mov     winflg2, 2                      ;
        mov     wintmr1, 0                      ;
        mov     wintmr2, 0                      ;
        call    clrpdbfrs                       ;
        call    clr_rr_hist                     ;
        mov     first_rwv_seen, 1               ;for ecg_lv3 dab ///
        cmp     plstmr,40                       ;check pulse timeout counter
        jbe     tmo_33
        mov     plstmr,40
tmo_33:
        MOV     AL,ECG_MODE
        AND     AL,NOT (EXT_TRIG)
        OR      AL,MODE_1                       ;SET IDLE MODE
        MOV     ECG_MODE,AL
        XOR     AX,AX
        MOV     ECGPERIOD,AX
        MOV     RRPER,AX
        mov     ecg_tmr,al
        ...
        OR      AL,AL
        JNZ     SHORT TMO_1
        CMP     SYNFLG,0
        JE      SHORT TMO_0
        XOR     AX,AX
        MOV     FRATE,AL
tmo_33a:
        MOV     RATE,AL
        MOV     VRATE,AX
        call    send_sat                ;update analog output    //anb
TMO_0:
        CALL    DSPSR
        OR      ALMFLG,ECGTMOF
        AND     ALMFLG,1 OR ECGTMOF OR PLSTMOF
        INC     ECGALMCHK
        CALL    ALMCHKB
        DEC     ECGALMCHK
        MOV     CL,LOWRATE OR HIRATE
        CALL    CLRLIT2
        CMP     ALICTR,0
        JE      SHORT TMO_1
        MOV     ALMDLY,1
TMO_1:
        mov     al, slide_mode          ;for slider - if use_ecg, ///
        test    al, use_ecg             ;use_ecg (= false, and    ///
        jz      short tmo_1a            ;clear munch's parameters ///
        and     al, not(use_ecg)        ;                         ///
        mov     slide_mode, al          ;                         ///
        mov     perctr, 0               ;just for fun, reset perctr ///
        mov     al, 0                   ;
        MOV     BX,OFFSET MCHMOD        ;RESET MUNCH'S PARAMETERS ///
        MOV     CX,11                   ;                         ///
tmo_1b:
        MOV     BYTE PTR [BX],AL        ;                         ///
        INC     BX                      ;                         ///
        LOOP    tmo_1b                  ;                         ///
tmo_1a:
        call    rwv_lost
        ret rwv_lost:
        mov     runsum, 0               ;for ecgbox ///
        mov     ecgboxcnt, 4            ; ditto     ///
        mov     ax,thresh_min
        mov     max_thresh,ax           ;set threshold for min. temp.
        mov     max_deriv,ax            ;
        mov     first_rwv_flg,1         ;wait for first r-wave
        mov     init_max_min, 1         ;next call to ecgatod should
                                        ; initialize ecgmax, ecgmin
        mov     least_rwv_lv3, 255      ;the next call to ecg_lv3 should
        RET                             ; update this value LEADS_CHK:
;CHECK FOR ECG LEADS OFF...SET CARRY IF LEADS ARE OFF
        XOR     AX,AX
        TEST    STATUS,LEADS_BIT
        MOV     CLR_LEADS,AL            ;CLEAR LEADS BIT FOR NEXT TIME
        JZ      SHORT LCL_1             ;IF Z,LEADS ARE OK
        OR      ECG_MODE,LEADS_OFF      ;SET LEADS OFF FLAG
        OR      COSTA,ECGOFF
        AND     SH_PAT_SAV,ECGDSABL     ;DISABLE ECG INPUT TO COMPARATOR
        STC
        RET
LCL_1:
LCL_2:
```

```
        AND     COSTA,NOT ECGOFF
        OR      SH_PAT_SAV,NOT ECGDSABL
        CLC
        RET

; Checking and adjusting threshold for ecgboxcar modul
chk_thresh:
        test    ecg_block,0ffffh        ;wait til 50 ms is over
        jnz     ct_ret
        test    block_flg,1             ;adjust just one time after every r-wave
        jz      ct_ret
        dec     block_flg               ;clear block active flag
        mov     ax,old_deriv            ;take 75% of old max
        mov     bx,ax
        mov     cl,2
        shr     bx,cl
        sub     ax,bx
        mov     bx,max_deriv            ;and 25% of new max
        shr     bx,cl
        add     ax,bx                   ;new average max value
        mov     old_deriv,ax
        mov     bx,ax                   ;and take 75% of this value
        shr     bx,cl
        sub     ax,bx                   ;new threshold
        jmp     ct21                    ;jump; ignore the rest
ct21:
        cmp     ax,thresh_min           ;if threshold < min
        ja      ct3
        mov     ax,thresh_min           ;set min value
ct3:
        mov     max_thresh,ax           ;set threshold
ct_ret:
        ret set_thresh:
        test    find_max_req,0ffh
        jz      st1                     ;return if no max deriv search mode
        test    find_cnt,0ffffh
        jnz     st_ret                  ;return if inside 2 sec time interval
        mov     find_max_req,0          ;reset flag
        mov     ax,max_deriv            ;calculate 75% of max deriv value
        mov     old_deriv,ax            ;save average max_deriv
        mov     bx,ax
        mov     cl,2
        shr     bx,cl
        sub     ax,bx
        mov     max_thresh,ax           ;new threshold value
        inc     set_flg                 ;check if any r-wave in the next 2 sec
        mov     set_flag_cnt,TIME2000*5
        jmp     min_chk
st1:
        test    set_flg,0ffh            ;inside the next 2 sec interval
        jz      st_ret                  ;jump if no
        test    set_flag_cnt,0ffffh
        jnz     st_ret                  ;jump if < 2 sec
        mov     set_flg,0               ;reset flag
        cmp     ecgsdly,0
        je      st_ret                  ;jump ecg is synced mov     ax,max_thresh
        mov     bx,ax
        shr     bx,1
        shr     bx,1
        shr     bx,1
        sub     ax,bx
        mov     max_thresh,ax           ;load min value
        inc     set_flg                 ;look for max again
        mov     find_cnt,TIME2000*5
min_chk:
        mov     ax,thresh_min           ;check threshold value against min_thresh
        cmp     ax,max_thresh
        jbe     st_ret
        mov     max_thresh,ax           ;load minimum threshold value
st_ret:
        ret ;calc_slide_tmo calculates how long an interval may elapse since
;the last good R wave before the slider buffer should be cleared.
;It uses 2 and 1/2 times the average R-R period. ///
calc_slide_tmo:
        mov     ax, rravg               ;
        mov     bx, ax                  ;
        shl     ax, 1                   ;2 * rravg
        jc      calc1                   ;overflow
        shr     bx, 1                   ;1/2 * rravg
        add     ax, bx                  ;
        jc      calc1                   ;overflow
        jmp     calc2                   ;
calc1:
        mov     ax, 0ffffh              ;set to maximum
calc2:
        mov     slide_tmo, ax           ;
        ret                             ;

;clr_rr_hist clears the r-r history buffer   dab ///
clr_rr_hist:
        mov     cx, 8                   ;clear 8 words from es:di
        mov     di, offset ds:rrper
        push    ds
        pop     es
        xor     ax, ax
        cld
        rep     stosw
        ret
```

```
;Ecg boxcar filter.
ecgbox:
        mov     dx, bx                          ;save ecgdiidx
        mov     di, offset ds:ecg_buf           ;0 data?
        cmp     word ptr [bx+di],0              ;
        jne     ecgb0                           ;no
        MOV     runsum, 0                       ;yes, initialize the sum, set countdown
        mov     ecgboxcnt, 4                    ;
        mov     cx, 0                           ;
        jmp     ecgb1                           ;initialization complete, leave
ecgb0:
        sub     bx, 8                           ;have bx index ecg_buf[ecgiidx-4]
        and     bx, ecgmask                     ;
        MOV     AX,runsum                       ;
        cmp     ecgboxcnt, 0                    ;safe to subtract oldest value?
        jne     ecgb0b                          ;no
        SUB     AX,WORD PTR [BX + DI]           ;yes
ecgb0b:
        mov     bx, dx                          ;retrieve ecgdiidx
        add     ax,WORD PTR [BX + DI]           ;add in newest value
        MOV     runsum,AX                       ;AX contains runsum
        cmp     ecgboxcnt, 0                    ;sums valid yet?
        je      ecgb2                           ;yes
        dec     ecgboxcnt                       ;no
        cmp     ecgboxcnt, 0                    ;sums valid yet to compute entry?
        je      ecgb2                           ;yes
        mov     cx, 0                           ;
        jmp     short ecgb1                     ;
ecgb2:
        SHR     AX,1                            ;get 1/2 running sum
        and     bx, ecgmask                     ;bx indexes ecgbuf[ecgiidx-1]
        mov     cx, word ptr [bx + di]          ;cx contains ecgbuf[ecgdiidx-1]
        sub     bx, 2                           ;
        and     bx, ecgmask                     ;bx indexes ecgbuf[ecgdiidx-2]
        add     cx,WORD PTR [BX + DI]           ;cx contains sum of middle two points
;following code determines whether midsum > 1/2 running sum
;cx to point to larger value, ax to smaller.
;Purpose is to compute |midsum - 1/2 running sum|.
;On entry ax contains 1/2 running sum.
        cmp     cx, ax                          ;
        jae     ecgb1a                          ;
        xchg    cx, ax                          ;
ecgb1a:
        sub     cx, ax                          ;
ecgb1:
        mov     bx, dx                          ;retrieve ecgdiidx
        mov     di, offset ds:ecgboxbuf         ;
        mov     word ptr [bx + di], cx          ;enter answer
        cmp     ecg_block, 0                    ;should be finding maximum?
        je      ecgb1b                          ;no
        cmp     cx, max_deriv                   ;data > max_deriv?
        jbe     ecgb12                          ;no, exit
        mov     max_deriv, cx                   ;yes
        jmp     ecgb12                          ;now exit
ecgb1b:
        cmp     cx, max_thresh                  ;data > max_thresh?
        jbe     short ecgb12                    ;no
        cmp     ecg200ms, 0                     ;safe to block? ///
        jne     short ecgb1c                    ;no            ///
        mov     ecg_block,TIME100               ;yes, set block_out timer
ecgb1c:
        test    ecg_mode, ignore_rwv            ;should ignore rwave because signal railed?
        jz      short ecgb1d                    ;no
        jmp     short ecgb12                    ;yes
ecgb1d:
        cmp     first_rwv_flg, 1                ;first rwave seen?
        je      short ecgb1ca                   ;yes, don't update max_deriv
        mov     max_deriv, cx                   ;
ecgb1ca:
        call    rwave_chk                       ;
ecgb12:
        ret                                     ;

slider:
        push    bx                              ;
        mov     al, slide_mode                  ;
        test    al, use_ecg                     ;are we using ecg?
        jnz     slide0                          ;yes
        jmp     no_ecg                          ;no
slide0:                                         ;using ecg
        xor     al,al                           ;anb
        cmp     fmode,2                         ;if mode2 (beat-beat)
        je      slide1                          ;   this_weight = 0
        mov     al, weight                      ;else this_weight = weight
slide1:
        mov     this_weight, al                 ;
        lea     bx, datbuf                      ;check if ir = red = 0
        mov     al, dopidx                      ;
        xor     ah, ah                          ;
        add     bx, ax                          ;
        mov     cx, [bx]                        ;   cx <- datbuf[dopidx]   (IR)
        mov     ax, [bx+2]                      ;   ax <- datbuf[dopidx+2] (Red)
        or      cx, ax                          ;ir = red = 0?
        jnz     short slide4                    ;no
        mov     al, slide_mode                  ;ir = red = 0
        and     al, not (use_ecg)               ;  reset using ecg flag to no
        or      al, skip_next_rwv               ;  & skip next r wave interrupt
        cmp     metermode, 4                    ;change metermode 4
        jne     short slide2                    ;
        mov     metermode, 3                    ;  to 3
        jmp     short slide3                    ;
```

```
slide2:
        cmp     metermode, 6            ;
        jne     short slide3            ;change metermode 6
        mov     metermode, 5            ;  to 5
slide3:
        mov     ax, 0                   ;
        call    clr_newbf               ;clear entire newbuf
        mov     newIidx2_on,0           ;& turn off 2nd newbuf ptr
        jmp     slidx                   ;& we're done
slide4:                                 ;ir and red have data not equal to 0
        mov     al, dopidx              ;has dopidx caught up to dattrig?
        cmp     al, dattrig             ;  i.e. to where the ecg occurred
        mov     al, slide_mode          ;
        jnz     short slide5            ;no
        and     al, not (shld_skip)     ;yes, then don't skip putting data
        mov     slide_mode, al          ;  into the slider
        mov     mchmod,0                ;anb per dab insistence !!!
        jmp     short slide7            ;
slide5: test    al, shld_skip           ;should we skip putting data into
                                        ;  slider buffer?
        jz      short slide7            ;not skipping
        mov     al,newiidx2_on          ;yes skipping
        or      al,al                   ;  is slider's ptr2 active?
        jnz     slide6                  ;  yes,
        jmp     slidx                   ;  not on, leave routine
slide6:                                 ;skip mode - we advance slider's ptr2 alone
        lea     bx,datbuf               ;
        mov     al,dopidx               ;
        xor     ah,ah                   ;
        add     bx,ax                   ;
        mov     ax,[bx]                 ;get ir data from datbuf
        push    bx                      ;save datbuf pointer
        lea     bx,newbuf               ;
        add     bx,newiidx2             ;
        mov     cx,[bx]                 ;get ir data at slider's 2nd pointer
        push    bx                      ;  and save ptr2
        call    new_avg                 ;average the two ir values and
                                        ;  return new weighted ave in ax
        pop     bx                      ;restore slider's 2nd ptr
        mov     [bx],ax                 ;  and store new ir average
                                        ;now get weighted average for the red
        inc     bx                      ;retrieve the red
        inc     bx                      ;  value from
        mov     cx,[bx]                 ;  slider's 2nd pointer
        pop     dx                      ;
        push    bx                      ;save slider's 2nd pointer
        mov     bx,dx                   ;put datbuf pointer in bx
        inc     bx                      ;retrieve the red
        inc     bx                      ;  value from
        mov     ax,[bx]                 ;  datbuf
        call    new_avg                 ;average the two red values
        pop     bx                      ;and store the weighted ave
        mov     [bx],ax                 ;  at slider's 2nd pointer
        jmp     slidx                   ;and we're done
slide7:                                 ;not in skip mode - both slider ptrs advanced
        lea     bx, newbuf              ;find slider's 1st pointer
        mov     ax, newiidx             ;
        add     bx, ax                  ;
        push    bx                      ;save it for later
        mov     cx, [bx]                ;get data it points to
        or      cx, cx                  ;Is it zero?
        jnz     short slide8            ;no, leave weight alone
        xor     al, al                  ;yes,
slide8:
        lea     bx, datbuf              ;point to data in datbuf
        mov     al, dopidx              ;
        xor     ah, ah                  ;
        add     bx, ax                  ;
        pop     cx                      ;restore slider's 1st ptr
        lea     dx, newbuf              ;get slider's 2nd pointer
        mov     ax,newiidx2             ;
        add     dx,ax                   ;
        call    put_newbf               ;add new data to slider
                                        ;bx points to datbuf[dopidx],
                                        ;cx points to newbuf[newiidx],
                                        ;dx points to newbuf[newiidx2]
        jmp     short slidx             ;we're done
no_ecg:
        mov     al, slide_mode          ;
        test    al, first_time          ;
        jnz     short slidx             ;first_time flag already set
        mov     ax, elapse_sec          ;get number of seconds since time out
        cmp     ax, slide_tmo           ;
        jae     short set_flg           ;eight seconds or more have elapsed, set flag
        mov     al, elapse_hb           ;get number of heart beats since time out
        cmp     al, 5                   ;
        jae     short set_flg           ;5 or more heart beats since time out
        jmp     short slidx             ;everything's ok
set_flg:
        mov     al, slide_mode          ;
        or      al, first_time          ;set the first_time
        mov     slide_mode, al          ;
slidx:
        pop     bx                      ;
        ret                             ;

;put_newbf moves entries from datbuf to newbuf using the following
;formula:
;newbuf[newiidx] <- ((this_weight-1)/this_weight)newbuf[newiidx] + (
;                    1/this_weight)datbuf[dopidx]
;
```

```
;This procedure assumes bx points to datbuf[dopidx], cx points to
;newbuf[newiidx]. Remember, both IR and red values must be placed.
;dx points to newbuf[newiidx2]
put_newbf:
        push    dx                      ;save newbuf[newiidx2]   axp///
        push    bx                      ;
        push    cx                      ;
        mov     ax, [bx]                ;ax = datbuf[dopidx] IR
        pop     bx                      ;
        push    bx                      ;
        mov     cx, [bx]                ;cx = newbuf[newiidx] IR
        call    new_avg                 ;
        pop     bx                      ;
        mov     [bx], ax                ;
        inc     bx                      ;
        inc     bx                      ;
        push    bx                      ;
        mov     cx, [bx]                ;cx = newbuf[newiidx] red
        pop     dx                      ;
        pop     bx                      ;
        push    dx                      ;
        inc     bx                      ;
        inc     bx                      ;
        mov     ax, [bx]                ;ax = datbuf[dopidx] red
        call    new_avg                 ;
        pop     bx                      ;
        mov     [bx], ax                ;
;axp///+
        mov     dl,newiidx2 on          ;bx = newiidx for the red data
        or      dl,dl                   ;is 2nd newbuf pointer active?
        pop     dx                      ;(meanwhile,get 2nd newbuf pointer to ir)
        je      short putnew0           ;no, newiidx2 inactive
        dec     bx                      ;yes,copy ir,red from 1st to 2nd newbuf ptr
        dec     bx                      ;  back up to 1st ir
        mov     cx,[bx]                 ;  & save contents
        mov     bx,dx                   ;  point to 2nd ir
        mov     [bx],cx                 ;  copy into 2nd ir
        inc     bx                      ;  advance to 2nd red
        inc     bx                      ;
        mov     [bx],ax                 ;  and copy into 2nd red
putnew0:
        ret                             ;

;new_avg - if weight is 0, return datbuf[dopidx] in ax.
;          else, return (weight-1)/weight newbuf[newiidx] + 1/weight datbuf[dopidx] in ax.
;Routine assumes ax = datbuf[dopidx], cx = newbuf[either newiidx or newiidx2]
;Improvement - round division returns rather than truncating
new_avg:
        cmp     cx,0                    ;zero in newbuf?
        je      short newx              ;yes, then return 100% boxcar
        mov     bh, 0                   ;
        mov     bl, this_weight         ;
        or      bx, bx                  ;
        jz      short newx              ;
        mov     dx, 0                   ;
        div     bx                      ;dxax/bx = ax rem dx = datbuf[dopidx]/weight
        push    ax                      ;save result
        mov     ax, cx                  ;
        mov     dx, 0                   ;
        div     bx                      ;dxax/bx = ax rem dx = newbuf[newiidx]/weight
        dec     bx                      ;get weight - 1
        mul     bx                      ;ax * bx = dxax = (weight-1)(newbuf[newiidx]/weight)
        or      dx, dx                  ;result too big?
        jz      new1                    ;no
        pop     ax                      ;yes, clear stack
        mov     ax, 0ffffh              ;and return
        jmp     newx                    ;
new1:
        mov     bx, ax                  ;save result
        pop     ax                      ;
        add     ax, bx                  ;result too big?
        jnc     newx                    ;no
        mov     ax, 0ffffh              ;yes, return
newx:
        ret                             ;

;clr_newbf - routine to clear newbuf. Assume ax contains the index
;into newbuf from which to clear it; i.e., clear newbuf from where
;ax points to til the end.
clr_newbf:
        lea     bx, newbuf              ;
        add     bx, ax                  ;bx points to address from which to clear
        mov     cx, newlen              ;
        sub     cx, ax                  ;cx contains number of bytes to clear
        or      cx, cx                  ;
        jz      short clr2              ;zero is a problem
        js      short clr2              ;so is a negative number
        cmp     cx, 688                 ;
        ja      clr2                    ;so is too large a number
        shr     cx, 1                   ;need to know how many words to clear
        mov     di, bx                  ;
        push    ds                      ;
        pop     es                      ;
        xor     ax, ax                  ;loop counter is fine
        cld                             ;
        rep     stosw                   ;
clr2:
        ret                             ;
```

FOURIER OXIMETER ASYST LISTING

Software
Appendix B

```
0 0 D/A.TEMPLATE CHNL0

1 2 A/D.TEMPLATE CHNLS.23
1 2 A/D.TEMPLATE CHNLS.CAL

14 STRING FILE.NAME

INTEGER DIM[ 512 , 2 ] ARRAY RAW.DAT.1
        DIM[ 512 , 2 ] ARRAY RAW.DAT.2
        DIM[ 1 ] ARRAY ISAT
        DIM[ 2048 , 8 ] ARRAY DAT.BUF

SCALAR PTR  SCALAR CTR  SCALAR HOW.LONG  SCALAR PTR.MAX
   SCALAR PTR.MIN  SCALAR RCAL SCALAR MIN1 SCALAR MIN2

COMPLEX
    DIM[ 128 ] ARRAY SHORT.DAT
    DIM[ 128 ] ARRAY SCONJ.DAT
    DIM[ 512 ] ARRAY FOR.DAT
    SCALAR FOR.DC

REAL
    DIM[ 512 ] ARRAY HAMMING.DAT
    DIM[ 1024 ] ARRAY SAT.DAT
    SCALAR RED.MAX SCALAR IR.MAX  SCALAR RNEW
    SCALAR SAT SCALAR BO1 SCALAR BO2 SCALAR BR1 SCALAR BR2 SCALAR SLOPE
    SCALAR INTERCEPT  SCALAR QUAL

: set.up
    HAMMING.DAT [ ]RAMP
    HAMMING.DAT 2. * PI * 512. / COS -.46 * .54 + HAMMING.DAT :=
    0 MIN1 := 0 MIN2 := 4095 ISAT :=
    1 set.#.optima
    5 set.#.points
;

: SET.TEMPLATE
    CHNLS.23
    RAW.DAT.1 RAW.DAT.2 CYCLIC DOUBLE.TEMPLATE.BUFFERS
    .6 CONVERSION.DELAY
    CHNL0 ISAT CYCLIC TEMPLATE.BUFFER
;

: WAIT.FOR.USER
    SCREEN.CLEAR
    10 10 GOTO.XY
    INTEN.ON
    ." SET LOCATION 24 TO 0 ... THEN: "
    ." STRIKE ANY KEY TO BEGIN. "  CR
    INTEN.OFF
    PCKEY ?DROP DROP
```

```
: OPEN.DATA.FILE
    NORMAL.DISPLAY
    ." HOW LONG A DATA SET IN MINUTES ? " #INPUT 7 * HOW.LONG :=
    CR
    ." ENTER THE FILE NAME XXXXXXXX.DAT " "INPUT FILE.NAME ":=
    CR ." PLEASE WAIT WHILE THE DATA FILE IS CREATED... "
    FILE.TEMPLATE
        COMPLEX DIM[ 512 ] SUBFILE
        HOW.LONG TIMES
    END
    FILE.NAME DEFER> FILE.CREATE
;

: START.ACQ
    DAS.INIT
    CLEAR.TASKS
    CHNL0 1 TASK ARRAY>D/A.OUT
    CHNLS.23 2 TASK A/D.IN>ARRAY
    17 TASK.PERIOD
    PRIME.TASKS
    TRIGGER.TASKS
;

: STOP.ACQ
    STOP.TASKS
    CLEAR.TASKS
    NORMAL.DISPLAY
;

: FIND.BETAS              \ GET BETAS FOR SAT CALC
    RCAL                  \ PLACE RCAL ON THE STACK

CASE
\ RCAL     B01      BR1      B02      BR2      SLOPE       INTERCEPT

OF     10563    27960    5069     51763    -15743      9237      ENDOF

ENDCASE

INTERCEPT :=
    SLOPE :=
    BR2 :=
    B02 :=
    BR1 :=
    B01 :=
;

: SHORT.FLIP
        128 2 DO
        130 I - PTR :=
        SHORT.DAT [ I ] SCONJ.DAT [ PTR ] :=
        LOOP
        SHORT.DAT [ 1 ] SCONJ.DAT [ 1 ] :=
        SCONJ.DAT CONJ SCONJ.DAT :=
```

```
\ ***** COMPUTE SATURATION
    QUAL .2 > IF
    BR2 RNEW BR1 * - B01 BR1 - RNEW * B02 - BR2 + / 100. *
    SAT :=
    SAT 70. <  if
    RNEW 4. / SLOPE * INTERCEPT + 4. * 256. /
    SAT :=
    else
    THEN
    SAT 102. > IF 102. SAT := ELSE THEN
    SAT 0. < IF 0. SAT := ELSE THEN
    SAT SAT.DAT [ CTR ] :=
    SAT 100. > IF 100. SAT := ELSE THEN.
    SAT 40.95 * FIX ISAT :=
    CR ." SAT = " CR SAT . CR  CTR .
    1 CTR + CTR :=
    .25 .51 VUPORT.ORIG
    .75 .50 VUPORT.SIZE
    SHORT.DAT ZMAG SUB[ 1 , 40 ] Y.AUTO.PLOT PTR.MIN 5 + CR .
    STACK.CLEAR
    ELSE
    THEN
;

: SHORT.PROCESS
home screen.clear
    FOR.DAT [ ]SUM 512. / DUP FOR.DC := FOR.DAT SWAP - FOR.DAT :=
    FOR.DC ZREAL 200. > IF
    FOR.DAT ZREAL [ ]MAX FOR.DAT ZREAL [ ]min - for.dc zreal  /
    dup .2 < IF
    0. > if
    FOR.DAT HAMMING.DAT * FOR.DAT :=
    FOR.DAT SUB[ 1 , 128 , 4 ] FOR.DAT SUB[ 2 , 128 , 4 ]
    FOR.DAT SUB[ 3 , 128 , 4 ] FOR.DAT SUB[ 4 , 128 , 4 ] + + + SHORT.DAT :=
    SHORT.DAT FFT SHORT.DAT :=
    SHORT.FLIP
    SHORT.DAT SCONJ.DAT + ZMAG
    SUB[ 4 , 30 ] DUP LOCAL.MAXIMA DROP 1 - PTR.MIN :=
    SUB[ PTR.MIN , 3 ] [ ]SUM IR.MAX :=
    SHORT.DAT SCONJ.DAT - ZMAG
    SUB[ 4 , 30 ] SUB[ PTR.MIN , 3 ] [ ]SUM RED.MAX :=
    RED.MAX FOR.DC ZIMAG / dup 256. / . cr
    IR.MAX FOR.DC ZREAL / dup 256. / . cr DUP QUAL := /
    ." R= " ? cr RNEW :=
    sat.comp
    THEN
    THEN
    ELSE ." TOO SMALL "
    THEN
    STACK.CLEAR
  : GET.IT
  HOW.LONG 1 + 1 DO
      BEGIN
      ?BUFFER.SWITCH
      UNTIL
      ?BUFFER.A/B
```

```
    IF
    RAW.DAT.1 XSECT[ ! , 1 ] MIN1 -
    .25 .01 VUPORT.ORIG
    .75 .50 VUPORT.SIZE
    DUP Y.AUTO.PLOT
    RAW.DAT.1 XSECT[ ! , 2 ] MIN2 -
    ELSE
    RAW.DAT.2 XSECT[ ! , 1 ] MIN1 -
    .25 .01 VUPORT.ORIG
    .75 .50 VUPORT.SIZE
    NO.LABELS
    DUP Y.AUTO.PLOT
    RAW.DAT.2 XSECT[ ! , 2 ] MIN2 -
    THEN
    Z=X+IY FOR.DAT :=
    FOR.DAT CTR SUBFILE ARRAY>FILE
    SHORT.PROCESS
LOOP
;

: IDLE.IT
    1 CTR :=
    BEGIN
    BEGIN
    ?BUFFER.SWITCH
    UNTIL
    ?BUFFER.A/B
    IF
    RAW.DAT.1 XSECT[ ! , 1 ] MIN1 -
    .25 .01 VUPORT.ORIG
    .75 .50 VUPORT.SIZE
    DUP Y.AUTO.PLOT
    RAW.DAT.1 XSECT[ ! , 2 ] MIN2 -
    ELSE
    RAW.DAT.2 XSECT[ ! , 1 ] MIN1 -
    .25 .01 VUPORT.ORIG
    .75 .50 VUPORT.SIZE
    DUP Y.AUTO.PLOT
    RAW.DAT.2 XSECT[ ! , 2 ] MIN2 -
    THEN
    Z=X+IY FOR.DAT :=
    SHORT.PROCESS
    ?KEY
    UNTIL
    PCKEY DROP
;

: SHOW.IT
STOP.ACQ
NORMAL.DISPLAY
SCREEN.CLEAR
home ." 1 STARTS A DISPLAY ONLY OXIMETER."
CR CR ." 2 DOES OXIMETRY AND STORES DATA FILES."
CR CR ." 3 CHECKS OFFSET CALIBRATION."
CR CR ." 4 READS RED AND IR VOLTAGES. "
CR CR ." 5 REPLAYS RECORDED DATA FILES "
```

```
CR CR ." 6 RETURNS TO DOS. "
CR CR ." 7 CLOSES DATA FILES ON ERRORS. "
cr cr ." 8 PRINT INSTRUCTIONS ON SCREEN. "
cr cr ." ENTER A SELECTION."
;
   SET.TEMPLATE
   1 CTR :=
   OPEN.DATA.FILE CR
   FILE.NAME DEFER> FILE.OPEN
   ." ENTER RCAL VALUE CODE ( 63 - 84 ) " #INPUT RCAL :=
   FIND.BETAS
   START.ACQ
   GRAPHICS.DISPLAY
   GRID.OFF
   GET.IT
   STOP.ACQ
   FILE.CLOSE
   NORMAL.DISPLAY
   SHOW.IT
   CR
;

: IDLE
   SET.TEMPLATE
   1 CTR :=
   ." ENTER RCAL VALUE CODE ( 63 - 84 ) " #INPUT RCAL :=
   FIND.BETAS
   START.ACQ
   GRAPHICS.DISPLAY
   GRID.OFF
   IDLE.IT
   STOP.ACQ
   NORMAL.DISPLAY
   SHOW.IT
   CR
;

: CAL.CHECK
   SET.TEMPLATE
   NORMAL.DISPLAY
   SCREEN.CLEAR
   WAIT.FOR.USER
   START.ACQ
   BEGIN
   ?BUFFER.SWITCH
   UNTIL
   STOP.ACQ
   RAW.DAT.1 XSECT[ ! , 1 ] []MIN DUP MIN1 := FLOAT 409.5 /
   ." IR zero is "    . cr
   RAW.DAT.1 XSECT[ ! , 2 ] []MIN DUP MIN2 := FLOAT 409.5 /
   ." Red zero is "   .
   3000 MSEC.DELAY
   SHOW.IT
;
```

```
: READ.VOLTS
    cr
    CHNLS.CAL
    A/D.INIT
    A/D.IN 409.5 / ." red volts = " . 409.5 / ." IR volts = " .
;

CHNL0 D/A.INIT
    1 CTR :=
    NORMAL.DISPLAY DIR *.DAT
    CR ." ENTER THE FILE TO REPLAY " "INPUT FILE.NAME ":=
    CR FILE.NAME DEFER> ?FILE
    CR ." ENTER RCAL VALUE " #INPUT RCAL :=
    FIND.BETAS
    CR ." WHICH FILE TO BEGIN REPLAY ? " #INPUT
    DUP 1 + CR ." HOW MANY FILES TO REPLAY " #INPUT + SWAP
    graphics.display DO
    I SUBFILE FOR.DAT FILE>ARRAY
    .25 .01 VUPORT.ORIG
    .75 .50 VUPORT.SIZE
    for.dat zreal y.auto.plot
    SHORT.PROCESS
    ISAT [ 1 ] D/A.OUT
    2000 msec.delay
    LOOP
    FILE.CLOSE
    SHOW.IT
;

: main.loop
  set.up
  show.it
  begin
      BEGIN
      #input
      ?dup not if
      cr ." Invalid number, re-enter: "
      then
      UNTIL
          case
          1 of idle endof
          2 of doit endof
          3 of cal.check endof
          4 of read.volts endof
          5 of replay.dat endof
          6 of bye endof
          7 of file.close endof
          8 of print.inst endof
          endcase
  again
  ONERR:

key drop
    MYSELF
;
```

```
banner: my.banner
CR
."                           NELLCOR PULSE OXIMETER"
CR CR CR
."                            FOR EXPERIMENTAL USE ONLY"
CR CR CR
."                               COPYRIGHT 1988"
CR CR
."                             PROPRIETARY INFORMATION"
CR CR .
."                              ALL RIGHTS RESERVED"
CR CR
."                         Written by: R. T. Stone, Ph.D."
;BANNER
```

We claim:

1. A method for calculating the amount of a blood constituent from the blood flow characteristics of a patient comprising:
   detecting an absorption signal corresponding to the absorption of light measured at two or more wavelengths in the patient's tissue including periodic changes in amplitude caused by periodic arterial pulses in the blood flow characteristics related to the patient's heartbeat and aperiodic changes in amplitude unrelated to the patient's heartbeat, and, for each of the measured wavelengths;
   obtaining a time-measure of the absorption signal including periodic information and aperiodic information;
   processing the time-measure collectively to determine a composite waveform having a relative maximum and minimum amplitude corresponding to a composite periodic waveform of the periodic information in the time-measure so that the aperiodic information present in the time-measure is attenuated and filtered from the composite; and thereafter
   calculating the amount of blood constituent from the relative maximum and minimum amplitude of the composite periodic waveforms of the detected wavelengths.

2. The method of claim 1 wherein obtaining a time-measure of the absorption signal further comprises updating the time-measure with the occurrence of new heartbeats so that the time-measure and the determined composite periodic waveform include periodic information related to the new heartbeats.

3. The method of claim 2 wherein the step of obtaining a time-measure of the absorption signal is updated with each occurrence of a heartbeat and the composite periodic information is updated by processing the updated time-measure.

4. The method of claim 3 wherein obtaining a time-measure of the absorption signal further comprises obtaining a plurality of selected portions of the detected absorption signal including the periodic information related to a corresponding plurality of heartbeats.

5. The method of claim 4 wherein obtaining a time-measure and processing the time-measure collectively further comprise:
   identifying the occurrence of the patient's heartbeat;
   correlating the occurrence of the heartbeat with the occurrence of the periodic information in the absorption signal associated with that heartbeat;
   synchronizing the occurrence of successive heartbeats;
   adding the periodic information in successive selected portions of the detected absorption signal phase, based on the synchronized occurrence of t. successive heartbeats and the determined corre: tion of the occurrence of the heartbeat and its ass ciated periodic information, thereby forming t composite periodic information.

6. The method of claim 5 wherein adding the perioc information further comprises:
   obtaining a first selected portion;
   obtaining a second selected portion corresponding a following heartbeat;
   applying a first weighting function to the first : lected portion, thereby forming a first weight portion;
   applying a second weighting function to the seco: selected portion, thereby forming a seco: weighted portion;
   adding the first and second weighted portions : gether to form the composite periodic informati waveform; and thereafter
   obtaining the composite periodic information as t first selected portion and a newly acquired select portion corresponding to the occurrence of a f( lowing heartbeat as the second selected portion.
   weighting the first and second portions by the fi: and second weighting functions; and
   adding the weighted first and second portions i gether, thereby providing an updated compos periodic information.

7. The method of claim 6 wherein the first and seco: weighting functions are selected to favor the seco: selected portion in the composite periodic informati waveform.

8. The method of claim 6 wherein the first and seco: weighting functions are fractional multiplyers that su to one.

9. The method of claim 5 wherein adding the perioc information further comprises:
   selecting a predetermined number of selected pc tions corresponding to a predetermined number successive heartbeats;
   obtaining a plurality of weighting functions;
   applying one of the plurality of weighting functio to each of the predetermined number of select portions so that each selected portion is weighte and
   adding the weighted portions together in synchror thereby forming the composite periodic inform tion waveform.

10. The method of claim 9 wherein the weighting functions are selected to favor the most recently acquired selected portion more than any other portion in the predetermined number of portions.

11. The method of claim 9 wherein the weighting functions are fractional multipliers that sum to one.

12. The method of claim 9 wherein the predetermined number of selected portions corresponds to the predetermined number of the most recent selected portions and updating the composite periodic information waveform further comprises:

replacing selected portions corresponding to heartbeats older than the predetermined number with selected portions corresponding to newly occurring heartbeats; and distributing the plurality of weighting functions so that the same weighting function is applied to the same selected portion relative to the most recent selected portion.

13. The method of claim 3 wherein obtaining a time-measure of the absorption signal further comprises obtaining a predetermined time-measure including a predetermined number of periodic information corresponding to the predetermined number of heartbeats.

14. The method of claim 13 wherein processing the collected time-measure further comprises Fourier transforming the collected time-measure into the frequency domain having spectral components corresponding to the frequency components of the collected time-measure, whereby the difference in the relative maximum and minimum amplitude and the average background intensity amplitude correspond to the amplitude at the spectral line for the predetermined number of heartbeats in the collected time-measure and the zero frequency spectral component respectively.

15. The method of claim 14 wherein processing the collected time-measure further comprises identifying the amplitude at the spectral component corresponding to the predetermined number of heartbeats by detecting a significant spectral component amplitude at the frequency corresponding to an integral multiple of the predetermined number of heartbeats.

16. The method of claim 14 wherein processing the collected time-measure further comprises identifying the amplitude at the spectral component corresponding to the predetermined number of heartbeats by detecting the patient's heartrate and correlating the detected heartrate for the time-measure to the spectral components of the transformed time-measure.

17. The method of claim 3 wherein the absorption signal further comprises two wavelengths, and wherein collecting the time-measure further comprises converting the absorption signals for each of the wavelengths into digital data;

collecting a first predetermined number of digitized data points for each of the wavelengths of the absorption signal;

forming a complex data set wherein one of the wavelengths data corresponds to the real component and the other of the wavelengths data correspond to the imaginary component;

determining the background absorption signal corresponding to the zero frequency component from the complex data set and subtracting the determined background absorption component from the complex data set, thereby forming a modified data set;

decimating the modified data set in time into a second predetermined number of samples;

processing the second predetermined number of samples using a function selected from among the group comprising Hamming windows and similar artifact reduction window functions, thereby forming a processed data set;

Fourier transforming the processed data set into the frequency domain;

determining the spectral components of the first and second wavelengths at the fundamental frequency for the first pretermined number of heartbeats in the time sample from the transform; and determining the relative maximum and minimum amplitudes for the first and second wavelengths using the amplitude of the zero frequency and fundamental frequency spectral components.

18. The method of claim 8 wherein the first weighting function is 5/6 and the second weighting function is 1/6.

19. The method of claim 13 further comprising determining the time of the occurrence of a heartbeat from the patient's ECG signal, and wherein obtaining a time-measure further comprises sampling the time-measure of the absorption signal to obtain a second predetermined number of samples per heartbeat, based on the determined time of occurrence of the heartbeats for each of the predetermined number of heartbeats in the time-measure.

20. An apparatus for calculating the amount of a blood constituent from a photoelectrically detected absorption signal corresponding to the absorption of light measured at two or more wavelengths in a patient's tissue, including periodic changes in amplitude caused by periodic arterial pulses in the blood flow characteristics that are related to the patient's heartbeat, and including aperiodic changes in amplitude unrelated to the patient's heartbeat, comprising:

means for receiving the photoelectrically detected absorption signals of each of the measured wavelengths;

means for obtaining a time-measure of the detected absorption signals including periodic information and aperiodic information;

means for processing the obtained time-measures collectively to determine a composite waveform having a relative maximum and minimum amplitude corresponding to a composite periodic waveform of the periodic information in the time-measure so that the aperiodic information present in the time-measure is attenuated and filtered from the composite; and means for calculating the amount of blood constituent from the relative maximum and minimum amplitude of the composite periodic waveforms of the detected wavelengths.

21. The apparatus of claim 20 wherein the means for obtaining a time-measure of the detected absorption signal further comprises means for updating the time-measure with the occurrence of new heartbeats so that the time-measure and the determined composite periodic waveform include periodic information related to the new heartbeats.

22. The apparatus of claim 21 wherein the means for updating the time-measure further comprises means for updating the time-measure with each occurrence of a heartbeat.

23. The apparatus of claim 22 wherein the means for obtaining a time-measure of the absorption signal further comprises means for obtaining a plurality of selected portions of the detected absorption signal including the periodic information related to a corresponding plurality of heartbeats.

24. The apparatus of claim 23 wherein the means for obtaining a time-measure and the means for processing the time-measure collectively further comprise:
- means for detecting the occurrence of the patient's heartbeat;
- means for correlating the detected occurrence of the heartbeat with the occurrence of the periodic information in the absorption signal associated with that heartbeat;
- means for synchronizing the occurrence of successive detected heartbeats; and
- means for adding the periodic information in successive selected portions of the detected absorption signal in phase, based on the synchronized occurrence of the detected successive heartbeats and the determined correlation of the occurrence of the heartbeat and its associated periodic information, thereby forming the composite periodic information.

25. The apparatus of claim 24 wherein the means for adding the periodic information further comprises:
- means for obtaining a first selected portion corresponding to a detected heartbeat;
- means for obtaining a second selected portion corresponding to a following heartbeat;
- first weighting means for applying a first weighting function to the first selected portion, thereby forming a first weighted portion;
- second weighting means for applying a second weighting function to the second selected portion, thereby forming a second weighted portion;
- means for adding the first and second weighted portion together, thereby forming the composite periodic information waveform; and
- means for obtaining the determined composite periodic information waveform as the first selected portion and a newly acquired selected portion of the detected absorption signal corresponding to the occurrence of a following heartbeat as the second selected portion so that the first and second weighting functions may be applied respectively to the composite and newly acquired portions and the weighted portions added together to form an updated composite information waveform.

26. The apparatus of claim 25 wherein the first and second weighting functions are selected to favor the second selected portion in the composite periodic information waveform.

27. The apparatus of claim 25 wherein the first and second weighting functions are fractional multiplyers that sum to one.

28. The apparatus of claim 27 wherein the first weighting function is 5/6 and the second weighting function is 1/6.

29. The method of claim 24 wherein the means for adding the periodic information further comprises:
- means for selecting a predetermined number of selected portions corresponding to a predetermined number of successive heartbeats;
- means for obtaining a plurality of weighting functions;
- means for applying one of the plurality of weighting functions to each of the predetermined number of selected portions so that each selected portion is weighted; and
- means for adding the weighted portions together in synchrony, thereby forming the composite periodic information waveform.

30. The apparatus of claim 29 wherein the weighting functions are selected to provide the most recently acquired selected portion with a greater weight than any other portion in the collected predetermined number of portions.

31. The apparatus of claim 29 wherein the weighting functions are fractional multipliers that sum to one.

32. The apparatus of claim 29 wherein the predetermined number of selected portions corresponds to the predetermined number of the most recent selected portions and the means for updating the composite periodic information waveform further comprises:
- processing means for replacing selected portions corresponding to heartbeats older than the predetermined number with selected portions corresponding to newly occurring heartbeats; and
- weighting means for distributing the plurality of weighting functions so that the same weighting function is applied to the same selected portion relative to the most recent selected portion.

33. The apparatus of claim 22 wherein the means for obtaining a time-measure of the detected absorption signal further comprises means for obtaining a predetermined time-measure including the periodic information corresponding to a predetermined number of heartbeats.

34. The apparatus of claim 33 wherein the means for processing the collected time-measure further comprises means for Fourier transforming the collected time-measure into a frequency domain waveform having spectral components corresponding to the frequency components of the collected time-measure, whereby the difference in the relative maximum amplitude corresponds to the amplitude at the spectral line for the predetermined number of heartbeats in the collected time-measure and the average background intensity amplitude corresponds to the amplitude at the zero frequency spectral component.

35. The apparatus of claim 34 wherein the means for processing the collected time-measure further comprises means for detecting the amplitude at the spectral component corresponding to the predetermined number of heartbeats by detecting a significant spectral component amplitude at a frequency that is about an integral multiple of the predetermined number of heartbeats.

36. The apparatus of claim 34 further comprising means for detecting the heartrate of the patient, wherein the means for processing the collected time-measure further comprises means for detecting the amplitude at the spectral component corresponding to the predetermined number of heartbeats and the detected heartrate.

37. The apparatus of claim 22 wherein the absorption signal further comprises two wavelengths, and wherein the means for collecting the time-measure further comprises means for converting the analog absorption signals for each of the wavelengths into digital data;
- means for collecting a first predetermined number of digitized data points for each of the wavelengths of the absorption signal;

first processor means for forming a complex data set wherein one of the wavelength data corresponds to the real component and the other of the wavelength data corresponds to the imaginary component;

second processor means for determining the background absorption signal corresponding to the zero frequency component from the complex data set and subtracting the determined background absorption component from the complex data set, thereby forming a modified data set;

means for decimating the modified data set in time into a second predetermined number of samples;

third processing means for processing the second predetermined number of samples using Hamming Window functions, thereby forming a processed data set;

means for Fourier transforming the processed data set into the frequency domain;

means for determining the spectral components of the first and second wavelengths at the fundamental frequency for the first predetermined number of heartbeats in the time sample from the transform; and means for determining the relative maximum and minimum amplitudes for the first and second wavelengths using the amplitude of the zero frequency and fundamental frequency spectral components.

* * * * *